US007015216B2

(12) United States Patent
Konradi et al.

(10) Patent No.: US 7,015,216 B2
(45) Date of Patent: Mar. 21, 2006

(54) HETEROARYL-β-ALANINE DERIVATIVES AS ALPHA 4 INTEGRIN INHIBITORS

(75) Inventors: Andrei W. Konradi, San Francisco, CA (US); Michael A. Pleiss, Sunnyvale, CA (US); Eugene D. Thorsett, Half Moon Bay, CA (US); Susan Ashwell, Plainsboro, NJ (US); Gregory S. Welmaker, Jackson, NJ (US); Anthony Kreft, Langhorne, PA (US); Dimitrios Sarantakis, Newtown, PA (US); Darren B. Dressen, San Francisco, CA (US); Francine S. Grant, San Carlos, CA (US); Christopher Semko, Fremont, CA (US); Ying-Zi Xu, Palo Alto, CA (US)

(73) Assignees: Elan Pharmaceuticals, Inc., South San Francisco, CA (US); Wyeth, Madison, NJ (US)

( * ) Notice: Subject to any disclaimer, the term of this patent is extended or adjusted under 35 U.S.C. 154(b) by 403 days.

(21) Appl. No.: 09/910,431

(22) Filed: Jul. 19, 2001

(65) Prior Publication Data

US 2002/0086882 A1 Jul. 4, 2002

Related U.S. Application Data

(60) Provisional application No. 60/220,128, filed on Jul. 21, 2000.

(51) Int. Cl.
```
C07D 213/02    (2006.01)
C07D 213/30    (2006.01)
C07D 403/06    (2006.01)
A61K 31/44     (2006.01)
A61P 19/02     (2006.01)
```
(52) U.S. Cl. ............... 514/222.5; 514/343; 514/345; 514/350; 514/357; 514/252.02; 514/252.11; 514/269; 544/8; 544/238; 544/322; 544/405
(58) Field of Classification Search ............... 544/211, 544/180, 182, 238, 322, 405, 8; 514/241, 514/242, 252.02, 252.11, 256, 269, 343, 345, 514/350, 357, 222.5; 546/268.1, 290, 300, 546/304, 314, 329, 339
See application file for complete search history.

(56) References Cited

FOREIGN PATENT DOCUMENTS

| WO | 97/36859 | 10/1997 |
|---|---|---|
| WO | 99/37618 | 7/1999 |
| WO | 99/43642 | 9/1999 |
| WO | 00/18759 | 4/2000 |
| WO | 00/20396 | 4/2000 |

OTHER PUBLICATIONS

West, Anthony R., Solid State Chemistry and its Applications, Wiley, New York, 1988, pp. 358 & 365.*
Abraham, W.M., et al., *J. Clin. Invest.*, 93, p. 776, (1994).
Berlin, C., et al., *Cell*, 74, p. 185, (1993).
Binns, R.M., et al., *J. Immunology*, 157, p. 4094, (1996).
Briskin, M.J., et al., *J. Immunol.*, 156, p. 719, (1996).
Cardarelli, P.M., et al., *J. Biol. Chem.*, 269, p. 18668, (1994).
Berger, E., et al., *PNAS*, 88, p. 8072, (1991).
Holzmann, B. et al., *EMBO J.*, 8, p. 1735, (1989).
Humphrieis, M. J., et al., *Ciba Foundation Symposium*, 189, p. 177, (1995).
Issekutz, T.B., *J. Immunology*, p. 3394, (1992).
Li, Z., et al., *Am. J. Physiol*, 263, L723, (1992).
Marlin, S., D., et al., *J. Exp. Med.*, 164, p. 855, (1986).
Osborne, L., *Cell*, 62, p. 3, (1990).
Podolsky, D.K., *J. Clin. Invest.*, 92, p. 373, (1993).
Shroff, H.N., *Bioorganic. Med. Chem. Lett.*, 6, p. 2495, (1996).
Sonnenberg, A., *Current Topics in Microbiology and Immunology*, 184, p. 7, (1993).
Springer, T.A., *Nature*, 346, p. 425, (1990).
Springer, T.A., *Cell*, 76, p. 301, (1994).
Vanderslice, P., *J. Immunol.*, 158, p. 1710, (1997).
Yang, X-D, et al., *PNAS*, 91, p. 12640, (1994).
Yednock, T.A., et al., *Nature*, 356, p. 63, (1992).

* cited by examiner

Primary Examiner—Venkararaman Balasubramanian
(74) Attorney, Agent, or Firm—Foley & Lardner LLP

(57) ABSTRACT

Disclosed are a series of heteroaryl-β-alanine derivatives, compositions containing them, processes for their preparation and their use in medicine.

10 Claims, No Drawings

HETEROARYL-β-ALANINE DERIVATIVES AS ALPHA 4 INTEGRIN INHIBITORS

CROSS REFERENCE TO RELATED APPLICATIONS

This application claims the benefit of U.S. Ser. No. 60/220,128, filed Jul. 21, 2000, which is incorporated by reference in its entirety.

This invention relates to a series of heteroaryl-β-alanine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed α4β1 consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognized [Sonnenberg, A. ibid.]

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al (Am. J. Physiol. 263, L723, (1992); Binns; R. M. et al J. Immunol. 157, 4094, (1996)]. A number of monoclonal antibodies which block adhesion molecule function are currently being investigated for their therapeutic potential in human disease.

One particular integrin subgroup of interest involves the α4 chain which can pair with two different beta chains β1 and β7 [Sonnenberg, A. ibid]. The α4β1 pairing occurs on many circulating leukocytes (for example lymphocytes, monocytes and eosinophils) although it is absent or only present at low levels on circulating neutrophils. α4β1 binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between α4β1 and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of α4 and β7 has been termed LPAM-1 [Holzmann, B and Weissman, I. EMBO J. 8, 1735, (1989)] and like α4β1, binds to VCAM-1 and fibronectin. In addition, α4β7 binds to an adhesion molecule believed to be involved in the homing of leukocytes to mucosal tissue termed MAdCAM-1 [Berlin, C. et al, Cell, 74, 185, (1993)]. The interaction between α4β7 and MAdCAM-1 may also be important at sites of inflammation outside of mucosal tissue [Yang, X-D. et al, PNAS, 91, 12604 (1994)].

Regions of the peptide sequence recognised by α4β1 and α4β7 when they bind to their ligands have been identified. α4β1 seems to recognise LDV, IDA or REDV peptide sequences in fibronectin and a QIDSP sequence in VCAM-1 [Humphries, M. J. et al, ibid] whilst α4β7 recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vandlerslice, P. J. Immunol. 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of α4 integrins. Members of the group are able to inhibit α4 integrins such as α4β1 and/or α4β7 at concentrations at which they generally have no or minimal inhibitory action on α integrins of other subgroups. The compounds are thus of use in medicine, for example in the prophylaxis and treatment of immune or inflammatory disorders as described hereinafter.

Thus according to one aspect of the invention we provide a compound of formula (1)

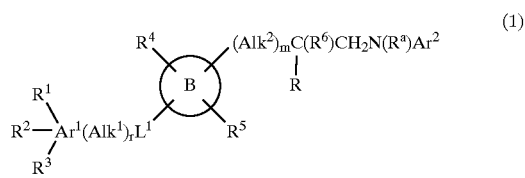

wherein $Ar^1$ is an aromatic or heteroaromatic group;

$R^1$, $R^2$, $R^3$, $R^4$ and $R^5$ which may be the same or different is each an atom or group $-L^2(Alk^3)_tL^3(R^7)_u$ in which $L^2$ and $L^3$ which may be the same or different is each a covalent bond or a linker atom or group, t is zero or the integer 1, u is an integer 1, 2 or 3, $Alk^3$ is an aliphatic or heteroaliphatic chain and $R^7$ is a hydrogen or halogen atom or a group selected from alkyl, $-OR^8$, where $R^8$ is a hydrogen atom or an optionally substituted alkyl group, $-SR^8$, $-NR^8R^9$, where $R^9$ is as just defined for $R^8$ and may be the same or different, $-NO_2$, $-CN$, $-CO_2R^8$, $-SO_3H$, $-SOR^8$, $-SO_2R^8$, $-OCO_2R^8$, $-CONR^8R^9$, $-OCONR^8R^9$, $-CSNR^8R^9$, $-COR^8$, $-OCOR^8$, $-N(R^8)COR^9$, $-N(R^8)CSR^9$, $-SO_2N(R^8)(R^9)$, $-N(R^8)SO_2R^9$, $-N(R^8)CON(R^9)(R^{10})$, where $R^{10}$ is a hydrogen atom or an optionally substituted alkyl group, $-N(R^8)CSN(R^9)(R^{10})$ or $-N(R^8)SO_2N(R^9)(R^{10})$;

$Alk^1$ is an optionally substituted aliphatic or heteroaliphatic chain;

$L^1$ is a covalent bond or a linker atom or group;

$Alk^2$ is a straight or branched alkylene chain;

m is zero or an integer 1;

$R^6$ is a hydrogen atom or a methyl group;

r is zero or the integer 1;

R is a carboxylic acid ($-CO_2H$) or a derivative thereof;

$R^a$ is a hydrogen atom or a methyl group;

$Ar^2$ is an optionally substituted aromatic or heteroaromatic group;

B is a nitrogen containing heteroaryl group;

and the salts, solvates, hydrates and N-Oxides thereof.

Another class of compounds within the scope of this invention include compounds of formula (II)

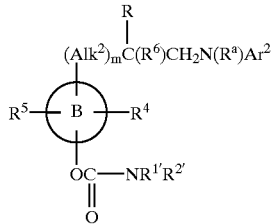

II wherein R, $R^a$, $R^4$, $R^5$, $R^6$, $Alk^2$, B, m and Ar are as defined above and $R^{1'}$ and $R^{2'}$ are independently selected from the group consisting of hydrogen, alkyl, substituted alkyl, alkenyl, substituted alkenyl, aryl, cycloalkyl, substituted cycloalkyl, heterocyclic, heteroaryl or and $R^{1'}$ and $R^{2'}$, together with the nitrogen atom to which they are attached, are joined to form an optionally substituted heterocyclic ring; and the salts, solvates, hydrates and N-oxides thereof.

In one preferred embodiment, and $R^{1'}$ and $R^{2'}$ are independently selected from the group consisting of hydrogen, alkyl, substituted alkyl, alkenyl, substituted alkenyl, cycloalkyl, substituted cycloalkyl, or and $R^{1'}$ and $R^{2'}$, together with the nitrogen atom to which they are attached, are joined to form an optionally substituted heterocyclic ring provided that said substituted alkyl, substituted alkenyl and substituted cycloalkyl do not carry an aryl, substituted aryl, heteroaryl or substituted heteroaryl group.

Preferably, in the compounds of this invention, $Ar^2$ is selected from the group consisting of moieties of formula IIIa, IIIc, IIId, IIIe or IIIf:

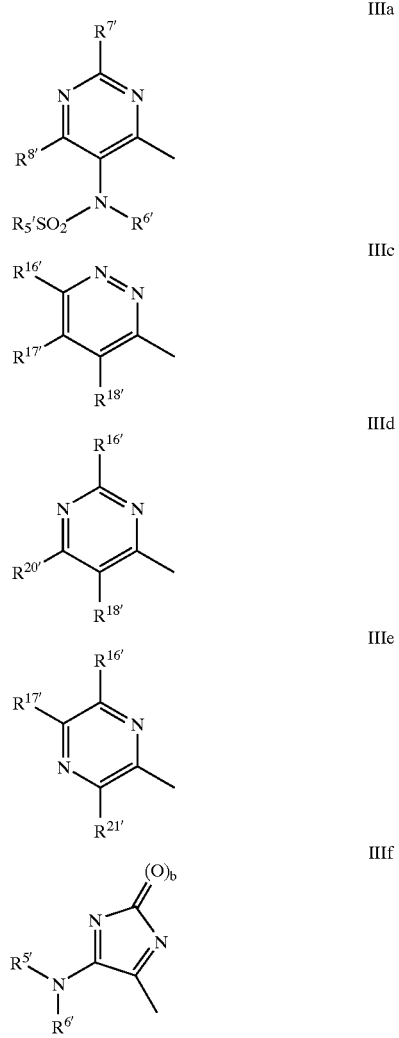

where $R^{5'}$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^{6'}$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and $-SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

$R^{7'}$ and $R^{8'}$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

$R^{16'}$ and $R^{17'}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and $R^{18'}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

$R^{20'}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

$R^{21'}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2;

and enantiomers, diastereomers and pharmaceutically acceptable salts thereof.

It will be appreciated that compounds of formula (1) may have one or more chiral centers, and exist as enantiomers or diastereomers. The invention is to be understood to extend to all such enantiomers, diastereomers and mixtures thereof, including racemates. Formula (1) and (II) and the formulae hereinafter are intended to represent all individual isomers and mixtures thereof, unless stated or shown otherwise.

In the compounds of formula (1), derivatives of the carboxylic acid group R include carboxylic acid esters and amides. Particular esters and amides include —CO$_2$Alk$^5$ groups and —CONR$^8$R$^9$ groups as described herein.

In general, the substituents $R^1$, $R^2$ and $R^3$ in compounds of the invention may be positioned on any available carbon atom, or, when present, nitrogen atom in the aromatic or heteroaromatic group represented by Ar$^1$.

When Alk$^1$ is present in compounds of formula (1) as an optionally substituted aliphatic chain it may be an optionally substituted $C_{1-10}$ aliphatic chain. Particular examples include optionally substituted straight or branched chain $C_{1-6}$ alkyl, $C_{2-6}$ alkenyl, or $C_{2-6}$ alkynyl chains.

Heteroaliphatic chains represented by Alk$^1$ include the aliphatic chains just described but with each chain additionally containing one, two, three or four heteroatoms or heteroatom-containing groups. Particular heteroatoms or groups include atoms or groups L$^4$ where L$^4$ is as defined above for L$^1$ when L$^1$ is a linker atom or group. Each L$^4$ atom or group may interrupt the aliphatic chain, or may be positioned at its terminal carbon atom to connect the chain to an adjoining atom or group.

Particular examples of aliphatic chains represented by Alk$^1$ include optionally substituted —CH$_2$—, —CH$_2$CH$_2$—, —CH(CH$_3$)—, —C(CH$_3$)$_2$—, —(CH$_2$)$_2$CH$_2$—, —CH(CH$_3$)CH$_2$CH$_2$—, —CH$_2$CH(CH$_3$)CH$_2$—, —C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups L$^4$ to form an optionally substituted heteroaliphatic chain. Particular examples include optionally substituted -L$^4$CH$_2$—, —CH$_2$L$^4$CH$_2$—, -L$^4$(CH$_2$)$_2$—, —CH$_2$L$^4$(CH$_2$)$_2$—, (CH$_2$)$_2$L$^4$CH$_2$—, -L$^4$(CH$_2$)$_3$— and —(CH$_2$)$_2$L$^4$(CH$_2$)$_2$— chains. The optional substituents which may be present on aliphatic or heteroaliphatic chains represented by Alk$^1$ include one, two, three or more substituents where each substituent may be the same or different and is selected from halogen atoms, e.g. fluorine, chlorine, bromine or iodine atoms, or $C_{1-6}$ alkoxy, e.g. methoxy or ethoxy, thiol, $C_{1-6}$ alkylthio e.g. methylthio or ethylthio, amino or substituted amino groups. Substituted amino groups include —NHR$^{12}$ and —N(R$^{12}$)$_2$ groups where $R^{12}$ is an optionally substituted straight or branched alkyl group as defined below for $R^{11}$. Where two $R^{12}$ groups are present these may be the same or different. Particular examples of substituted chains represented by Alk$^1$ include those specific chains just described substituted by one, two, or three halogen atoms such as fluorine atoms, for example chains of the type —CH(CF$_3$)—, —C(CF$_3$)$_2$— —CH$_2$CH(CF$_3$)—, —CH$_2$C(CF$_3$)$_2$—, —CH(CF$_3$)— and —C(CF$_3$)$_2$CH$_2$.

Alk$^2$ in the compounds of the invention may be for example a straight or branched $C_{1-3}$ alkylene chain. Particular examples include —CH$_2$—, —CH(CH$_3$)—and —(CH$_2$)$_2$—, When in the compounds of formula (1) $L^1$, $L^2$ and/or $L^3$ is present as a linker atom or group it may be any divalent linking atom or group. Particular examples include —O— or —S— atoms or —C(O)—, —C(O)O—, —OC(O)—, —C(S)—, —S(O)—, —S(O)$_2$—, —N(R$^{11}$)—, where $R^{11}$ is a hydrogen atom or an optionally substituted alkyl group, —CON(R$^{11}$)—, —OC(O)N(R$^{11}$)—, —CSN(R$^{11}$)—, —N(R$^{11}$)CO—, —N(R$^{11}$)C(O)O—, —N(R$^{11}$)CS—, —S(O)$_2$N(R$^{11}$)—, —N(R$^{11}$)S(O)$_2$—, —N(R$^{11}$)CON(R$^{11}$)—, —N(R$^{11}$)CSN(R$^{11}$)—, or —N(R$^{11}$)$_{SO2}$N(R$^{11}$)— groups. Where the linker group contains two $R^{11}$ substituents, these may be the same or different.

When $R^7$, $R^8$, $R^9$, $R^{10}$ and/or $R^{11}$ in the compounds of formula (1) is an alkyl group it may be a straight or branched $C_{1-6}$alkyl group, e.g. a $C_{1-3}$ alkyl group such as a methyl or ethyl group. Optional substituents which may be present on such groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When Alk$^3$ is present in compounds of formula (1) as an aliphatic or heteroaliphatic chain it may be for example any of the above-mentioned $C_{1-10}$ aliphatic or heteroaliphatic chains described for Alk$^1$.

Halogen atoms represented by $R^7$ in compounds of the invention include fluorine, chlorine, bromine, or iodine atoms.

Examples of the substituents represented by $R^1$, $R^2$, $R^3$, $R^4$ and $R^5$ in compounds of formula (1) include atoms or groups -L$^2$Alk$^3$L$^3$R$^7$, -L$^2$Alk$^3$R$^7$, -L$^2$R$^7$, -Alk$^3$R$^7$ and —R$^7$ wherein L$^2$, Alk$^3$, L$^3$ and R$^7$ are as defined above. Particular examples of such substituents include -L$^2$CH$_2$L$^3$R$^7$, -L$^2$CH(CH$_3$)L$^3$R$^7$, -L$^2$CH(CH$_2$)$_2$L$^3$R$^7$, -L$^2$CH$_2$R$^7$, -L$^2$CH(CH$_3$)R$^7$, -L$^2$(CH$_2$)2R$^7$, —CH$_2$, R$^7$, —CH(CH$_3$)R$^7$ and —(CH$^2$)2R$^7$ groups.

Thus each of $R^1$, $R^2$, $R^3$, $R^4$ and $R^5$ in compounds of the invention may be for example a hydrogen atom, a halogen atom, e.g. a fluorine, chlorine, bromine or iodine atom, or a $C_{1-6}$alkyl, e.g. methyl, ethyl, n-propyl, i-propyl, n-butyl or t-butyl, $C_{1-6}$alkylamino, e.g. methylamino or ethylamino, $C_{1-6}$hydroxyalkyl, e.g. hydroxymethyl or hydroxyethyl, carboxyC$_{1-6}$alkyl, e.g. carboxyethyl, $C_{1-6}$alkylthio e.g. methylthio or ethylthio, carboxyC$_{1-6}$alkylthio, e.g. carboxymethylthio, 2-carboxyethylthio or 3-carboxypropylthio, $C_{1-6}$alkoxy, e.g. methoxy or ethoxy, $C_{6-12}$ arylC$_{1-6}$alkyloxy e.g. benzyloxy, hydroxyC$_{1-6}$alkoxy, e.g. 2-hydroxyethoxy, haloC$_{1-6}$alkyl, e.g. trifluoromethyl, haloC$_{1-6}$alkoxy, e.g. trifluoromethoxy, $C_{1-6}$alkylamino, e.g. methylamino or ethylamino, amino (—NH$_2$), aminoC$_{1-6}$ alkyl, e.g. aminomethyl or aminoethyl, C$_{1-6}$dialkylamino, e.g. dimethylamino or diethylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, diisopropylaminoethoxy, or dimethylaminopropoxy, nitro, cyano, amidino, hydroxyl (—OH), formyl(HC(O)—), carboxyl (—CO$_2$H), —CO$_2$Alk$^5$, where Alk$^5$ is as defined below, C$_{1-6}$ alkanoyl e.g. acetyl, thiol (—SH), thioC$_{1-6}$alkyl, e.g. thiomethyl or thioethyl, thioC$_{1-6}$alkyl(C$_{6-12}$aryl e.g. thiobenzyl, sulphonyl (—SO$_3$H), C$_{1-6}$alkylsulphinyl e.g. methylsulphinyl, C$^{1-6}$ alkylsulphonyl, e.g. methylsulphonyl, aminosulphonyl (—SO$_2$NH$_2$), C$_{1-6}$ alkylaminosulphonyl, e.g. methylaminosulphonyl or ethylaminosulphonyl, C$_{1-6}$dialkylaminosulphonyl, e.g. dimethylaminosulphonyl or diethylanminosulphonyl, phenylaminosulphonyl, carboxamido (—CONH$_2$), C$_{1-6}$ alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$dialkylaminoC$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. ethylaminothiocarbonylmethyl-amino, C$_{1-6}$alkylsulphonylamino, e.g. methylsulphonylamino or ethylsulphonylamino, C$_{1-6}$ dialkylsulphonylamino, e.g. dimethylsulphonyl amino or diethylsubphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, C$_{1-6}$alkanoylamino, e.g. Acetylamino, aminoC$_{1-6}$alkanoylamino e.g. Aminoacetylamino, C$_{1-6}$dialkylaminoC$_{1-6}$alkanoylamino, e.g. dimethylaminoacetylamino, C$_{1-6}$alkanoylaminoC$_{1-6}$ alkyl, e.g. Acetylaminomethyl, C$_{1-6}$alkanoylaminoC$_{1-6}$ alkylamino, e.g. Acetamidoethylamino, C$_{1-6}$alkoxycarbonylamino, e.g. methoxycarbonylamino, ethoxycarbonylamino or t-butoxycarbonylamino group.

Aromatic groups represented by the group Ar$^1$ and/or Ar$^2$ in compounds of the invention include for example monocyclic or bicyclic fused ring C$_{6-12}$ aromatic groups, such as phenyl, 1- or 2-naphthyl, 1- or 2-tetrahydronaphthyl, indanyl or indenyl groups. Aromatic groups represented by the group Ar$^2$ may be optionally substituted by one, two, three or more R$^{13}$ atoms or groups as defined below. Heteroaromatic groups represented by the group Ar$^1$ and/or Ar$^2$ in the compounds of formula (1) include for example C$_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—C$_{1-6}$alkylimidazolyl oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, (2,3-dihydro)benzofuryl, benzothienyl, benzotriazolyl, indolyl, isoindolyl, benzimidazolyl, imidazo(1,2-a)pyridyl, benzothiazolyl, benzoxazolyl, benzopyranyl, (3,4-dihydro)benzopyranyl, quinazolinyl, quinoxalinyl, naphthyridinyl, pyrido(3,4-b)pyridyl, pyrido (3,2-b)pyridyl, pyrido(4,3-b)-pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by Ar$^2$ include one, two, three or more substituents, each selected from an atom or group R$^{13}$ in which R$^{13}$ is —R$^{13a}$ or -Alk$^4$(R$^{13a}$)m,
  wherein R$^{13a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{14}$, —CSR$^{14}$, —SO$_3$H, —SO$_2$R$^{14}$—SO$_2$NH$_2$, —SO$_2$NHR$^{14}$SO$_2$N(R$^{14}$)$_2$, —CONH$_2$, —CSNH$_2$, —CONHR$^{14}$, —CSNHR$^{14}$, —CON(R$^{14}$)$_2$, —CSN(R$^{14}$)$_2$, —N(R$^{12}$)SO$_2$R$^{14}$, —N(SO$_2$R$^{14}$)$_2$, —NH$_2$(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CON(R$^{14}$)$_2$, —N(R$^{11}$)CSN(R$^{14}$)$_2$, —N(R$^{11}$)CSR$^{14}$, —N(R$^{11}$)C(O)OR$^{14}$, —SO$_2$NHet$^1$, —CONHet$^1$, —CSNHet$^1$, —N(R$^{11}$)SO$_2$NHet$^1$, —N(R$^{11}$)CONHet$^1$, —N(R$^{11}$)CSNHet$^1$, —Het$^2$, —SO$_2$N(R$^{11}$)Het$^2$, —CON(R$^{11}$)Het$^2$, —CSN(R$^{11}$)Het$^2$, —N(R$^{11}$)CON(R$^{11}$)Het$^2$, —N(R$^{11}$)CSN(R$^{11}$)Het$^2$, aryl or heteroaryl group;
wherein
R$^{14}$ is an aryl or heteroaryl group,
—NHet$^1$ is an optionally substituted C$_{5-7}$cyclicamino group optionally containing one or more other —O— or —S— atoms or —N(R$^{11}$)—, —C(O)— or —C(S)- groups,
Het$^2$ is an optionally substituted monocyclic C$_{5-7}$carbocyclic group optionally containing one or more —O— or —S— atoms or —N(R$^{11}$)—, —C(O)— or —C(S)- groups,
Alk$^4$ is a straight or branched C$_{1-6}$alkylene, C$_{2-6}$alkenylene or C$_{2-6}$alkynylene chain, optionally interrupted by one, two or three —O— or —S— atoms or —S(O)$_n$, where n is an integer 1 or 2, or —N(R$^{15}$)— groups, where R$^{15}$ is a hydrogen atom or C$_{1-6}$alkyl, e.g. methyl or ethyl group; and m is zero or an integer 1, 2 or 3. It will be appreciated that when two R$^{11}$ or R$^{14}$ groups are present in one of the above substituents, the R$^{11}$ or R$^{14}$ groups may be the same or different.

When in the group -Alk$^4$(R$^{13a}$)$_m$ m is an integer 1, 2 or 3, it is to be understood that the substituent or substituents R$^{13a}$ may be present on any suitable carbon atom in -Alk$^4$. Where more than one R$^{13a}$ substituent is present these may be the same or different and may be present on the same or different atom in -Alk$^4$. Clearly, when m is zero and no substituent R$^{13a}$ is present the alkylene, alkenylene or alkynylene chain represented by Alk$^4$ becomes an alkyl alkenyl or alkynyl group.

When $R^{13a}$ is a substituted amino group it may be for example a group —NHR$^{14}$, where R$^{14}$ is as defined above, or a group —N(R$^{14}$)$_2$ wherein each R$^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —OR$^{14}$ or a —SR$^{14}$ or —SC(=NH)NH$_2$ group respectively.

Esterified carboxyl groups represented by the group $R^{13a}$ include groups of formula —CO$_2$Alk$^5$ wherein Alk$^5$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$ alkyl group such as an optionally substituted phenyloxymethyl, phenyloxyethyl, 1-naphthyl-oxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^5$ group include R$^{13a}$ substituents described above.

When Alk$^4$ is present in or as a substituent it may be for example a methylene, ethylene, n-propylene, i-propylene, n-butylene, i-butylene, s-butylene, t-butylene, ethenylene, 2-propenylene, 2-butenylene, 3 butenylene, ethynylene, 2-propynylene, 2-butynylene or 3-butynylene chain, optionally interrupted by one, two, or three —O— or —S—, atoms or —S(O)—, —S(O)$_2$— or —N(R$^{12}$)-groups.

Aryl or heteroaryl groups represented by the groups R$^{13a}$ or R$^{14}$ include mono- or bicyclic optionally substituted C$_{6-12}$ aromatic or C$_{1-9}$ heteroaromatic groups as described above for the group Ar$_2$. The aromatic and heteroaromatic groups may be attached to the remainder of the compound of formula (1) by any carbon or hetero e.g. nitrogen atom as appropriate.

When —NHet$^1$ or -Het$^2$ forms part of a substituent R$^{13}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or -Het$^2$ include those R$^7$ substituents described above.

Particularly useful atoms or groups which can be substituents on Ar$^2$ include fluorine, chlorine, bromine or iodine atoms, or C$_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, or thienyl, morpholinyl, thiomorpholinyl, piperazinyl, pyrrolidinyl, piperidinyl, C$_{1-6}$alkylamino, e.g. methylamino or ethylamino, C$_{1-6}$hydroxyalkyl, e.g. hydroxymethyl or hydroxyethyl, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxy-propylthio, C$_{1-6}$alkoxy, e.g. methoxy or ethoxy, hydroxyC$_{1-6}$alkoxy, e.g. 2-hydroxyethoxy, optionally substituted phenoxy, pyridyloxy, thiazolyoxy, phenylthio or pyridylthio, C$_{5-7}$cycloalkoxy, e.g. cyclopentyloxy, haloC$_{1-6}$alkyl, e.g. trifluoromethyl, haloC$_{1-6}$alkoxy, e.g. trifluoromethoxy, C$_{1-6}$alkylamino, e.g. methylamino or ethylamino or propylamino, optionally substituted C$_{6-12}$arylC$_{1-6}$alkylamino, e.g. benzylamino, fluorobenzylamino or hydroxyphenylethylamino, amino (—NH$_2$), amino C$_{1-6}$alkyl, e.g. aminomethyl or aminoethyl, C$_{1-6}$dialkylamino, e.g. dimethylamino or diethylamino, aminoC$_{1-6}$alklamino e.g. aminomethylamino, aminoethylamino or aminopropylamino, Het$^1$NC$_{1-6}$alkylamino e.g. morpholinopropylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, diisopropylaminoethoxy, or dimethylaminopropoxy, hydroxyC$_{1-6}$alkylamino, e.g. hydroxyethylamino, hydroxypropylamino or hydroxybutylamino, imido, such as phthalimido or naphthalimido, e.g. 1,8-naphthalimido, vitro, cyano, amidino, hydroxyl (—OH), formyl [HC(O)—], carboxyl (—CO$_2$H), —CO$_2$Alk$^5$, where Alk$^5$ is as defined above, C$_{1-6}$alkanoyl e.g. acetyl, propyryl or butyryl, optionally substituted benzoyl, thiol (—SH), thioC$_{1-6}$alkyl, e.g. Thiomethyl or thioethyl, —SC(=NH)NH$_2$, sulphonyl (—SO$_3$H), C$_{1-6}$alkyl-sulphinyl, e.g. methylsulphinyl, ethylsulphinyl or propylsulphinyl, C$_{1-6}$alkylsulphonyl, e.g. methylsulphonyl, ethylsulphonyl, propylsulphonyl, hexylsulphonyl or isobutylsulphonyl, aminosulphonyl (—SO$_2$NH$_2$), C$_{1-6}$alkylaminosulphonyl, e.g. methylaminosulphonyl, ethylaminosulphonyl or propylaminocsulphonyl, C$_{1-6}$dialkylaminosulphonyl, e.g. dimethylamino-sulphonyl or diethylaminosulphonyl, optionally substituted phenylaminosulphonyl, carboxamido (—CONH$_2$), C$_{1-6}$alkylaminocarbonyl, e.g. methylaminocarbonyl, ethylaminocarbonyl or propylaminocarbonyl, C$_{1-6}$dialkylaminocarbonyl, e.g. dimethylaminocarbonyl, diethylaminocarbonyl or dipropylaminocarbonyl, aminoC$_{1-6}$alkylaminocarbonyl, e.g. Aminoethylaminocarbonyl, C$_{1-6}$dialkylaminoC$_{1-6}$alkylaminocarbonyl, e.g. diethylaminoethylaminocarbonyl, aminocarbonylamino, C$_{1-6}$alkylaminocarbonyl-amino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocarbonylC$_{1-6}$alkylamino, e.g. methylaminocarbonylmethylamino, aminothiocarbonylamino, C$_{1-6}$alkyl-aminothiocarbonylamino, e.g. methylaminothiocarbonylamino or ethylaminothiocarbonylamino, C$_{1-6}$ dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, —CONHC(=NH)NH$_2$, C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, optionally substituted phenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonyl-amino or diethylaminosulphonylamino, optionally substituted morpholine-sulphonylamino or morpholinesulphonylC$_{1-6}$alkyl-amino, optionally substituted phenylaminosulphonylamino, C$_{1-6}$alkanoylamino, e.g. Acetylamino, aminoC$_{1-6}$alkanoylamino e.g. Aminoacetylamino, C$_{1-6}$dialkylaminoC$_{1-6}$alkanoylamino, e.g. dimethylaminoacetylamino, C$_{1-6}$ alkanoylaminoC$_{1-6}$alkyl, e.g. Acetylaminomethyl, C$_{1-6}$alkanoylaminoC$_{1-6}$ alkylamino, e.g. Acetamidoethylamino, C$_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylaminoC$_{1-6}$-alkyl e.g. benzyloxy carbonylaminoethyl, thiobenzyl, pyridylmethylthio or thiazolylmethylthio groups.

Where desired, two $R^{13}$ substituents may be linked together to form a cyclic group such as a cyclic ether, e.g. a $C_{1-6}$alkylenedioxy group such as methylenedioxy or ethylenedioxy.

It will be appreciated that where two or more $R^{13}$ substituents are present, these need not necessarily be the same atoms and/or groups. In general, the substituent(s) may be present at any available ring position in the aromatic or heteroaromatic group represented by $Ar^2$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. P-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds according to the invention the group $Ar^1$ is preferably a phenyl or monocyclic heteroaromatic group. Particularly useful groups of this type are five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups.

A particularly useful group of compounds according to the invention has the formula (2):

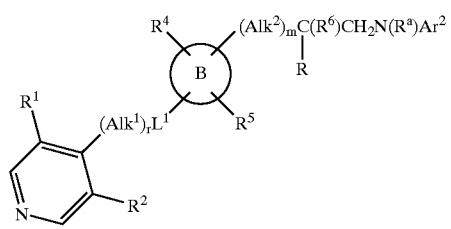

(2)

wherein $R^1$ and $R^2$, which may be the same or different is each an atom or group $-L^2(Alk^3)_tL^3(R^7)_u$ in which $L^2$, $Alk^3$, t, $L^3$, $R^7$ and u are as defined for formula (1) provided that $R^1$ and $R^2$ are not both hydrogen atoms; $Alk^1$, $Alk^2$, m, r, $L^1$, $R^4$, $R^5$, $R^6$, $R^a$, $Ar^2$, B and R are as defined for formula (1); and the salts, solvates, hydrates and N-oxides thereof.

$R^1$ and $R^2$ in compounds of formula (2) and in general in compounds of formula (1) is each preferably as particularly described above for compounds of formula (1), other than a hydrogen atom. Particularly useful $R^1$ and $R^2$ substituents include halogen atoms, especially fluorine or chlorine atoms, or methyl, halomethyl, especially —$CF_3$, —$CHF_2$ or —$CH_2F$, methoxy or halomethoxy, especially —$OCF_3$, —$OCHF_2$ or —$OCH_2F$ groups.

$R^3$ in compounds of the invention is in particular a hydrogen atom.

R in the compounds of formulae (1) and (2) is preferably a —$CO_2H$ group.

When present, the aliphatic chain represented by $Alk^1$ in compounds of formulae (1) and (2) is preferably a —$CH_2$— chain.

In general in compounds of formulae (1) and (2) $-(Alk^1)_rL^1$ is preferably —$CH_2O$— or —$CON(R^{11})$—. A particularly useful group is —CONH—.

In compounds of formulae (1) and (2) m is preferably 1 and $Alk^2$ is preferably —$CH_2$—.

$R^4$ and $R^5$ in the compounds of formulae (1) and (2) may be the same or different and is each preferably a hydrogen or halogen atom or an alkyl, alkoxy, hydroxy, nitro, cyano or —$NR^8R^9$ group.

$R^6$ and $R^a$ in the compounds of formulae (1) and (2) is each preferably a hydrogen atom.

Particularly useful classes of compounds according to the invention are those wherein $Ar^2$ is an optionally substituted monocyclic aromatic or heteroaromatic group. One especially useful aromatic group when represented by $Ar^2$ is phenyl. Especially useful heteroaromatic groups represented by $Ar^2$ include optionally substituted monocyclic nitrogen-containing heteroaromatic groups, particularly optionally substituted pyridyl, pyrimidinyl, pyridazinyl and triazinyl groups. Where the group is a triazinyl group it is preferably a 1,3,5 triazine.

Optional substituents which may be present on preferred $Ar^2$ aromatic or heteroaromatic groups include for example one or two substituents selected from those $R^{13}$ substituents described above.

Other atoms or groups which can be substituents on $Ar^2$ include a halogen atom, especially fluorine or chlorine, morpholinyl, thiomorpholinyl, optionally substituted piperidinyl, especially piperidinyl or 4-carboxypiperidinyl, pyrrolidinyl, optionally substituted piperazinyl, especially t-butyloxycarbonylpiperazinyl, thio$C_{1-6}$alkyl, especially thiomethyl, thioethyl or thiopropyl, optionally substituted thiobenzyl, especially thiobenzyl, halo$C_{1-6}$alkyl, especially trifluoromethyl, $C_{1-6}$alkyloxy, especially methoxy, ethoxy or propoxy, optionally substituted benzyloxy, especially benzyloxy, halo$C_{1-6}$alkoxy, especially trifluoromethoxy and difluoromethoxy, $C_{1-6}$alkylamino, especially methylamino, ethylamino or propylamino, $C_{1-6}$dialkylamino, especially dimethylamino or diethylamino, optionally substituted $C_{6-12}$aryl$C_{1-6}$alkylamino, especially benzylamino, 4-substituted benzyl, especially 4-fluorobenzylamino or 4-hydroxyphenylethylamino, aminoalkylamino, especially 3-aminopropylamino, $Het^1NC_{1-6}$alkylamino, especially 3-morpholinopropylamino, optionally substituted phenoxy, especially phenoxy, hydroxy$C_{1-6}$alkylamino, especially 2-hydroxyethylamino, 3-hydroxypropylamino and 3-hydroxybutylamino, nitro, carboxyl, —$CO_2Alk^5$, where $R^5$ is as defined above, especially carboxymethyl and carboxyethyl, carboxamido, $C_{1-6}$alkylaminocarbonyl, especially methylaminocarbonyl, ethylaminocarbonyl and propylaminocarbonyl, $C_{1-6}$dialkylaminocarbonyl, especially dimethylaminocarbonyl, diethylaminocarbonyl or dipropylaminocarbonyl, $C_{1-6}$alkanoyl, especially acetyl, propyryl or butyryl, optionally substituted benzoyl, especially benzoyl, $C_{1-6}$alkylsulphinyl, especially methylsulphinyl, ethylsulphinyl or propylsulphinyl, $C_{1-6}$alkylsulphonyl, especially methylsulphonyl, ethylsulphonyl, propylsulphonyl, hexylsulphonyl or isobutylsulphonyl, $C_{1-6}$alkylaminosulphonyl, especially ethylaminosulfonyl or propylaminosulphonyl, $C_{1-6}$dialkylaminosulphonyl, especially diethylaminosulphonyl, $C_{1-6}$alkylaininocarbonyl, especially methylaminocarbonyl, ethylaminocarbonyl or propylaminocarbonyl, $C_{1-6}$dialkylaminocarbonyl, especially dimethylaminocarbonyl or diethylaminocarbonyl.

Particularly useful $Alk^4$ groups when present in compounds of the invention include —$CH_2$—, —$CH_2CH_2$—, —$(CH_2)_2CH_2$— —$CH(CH_3)CH_2$— and —$(CH_2)_3CH_2$— groups.

As used herein, the following terms have the following meanings unless more limited definitions are used:

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —NRS$(O)_2$ -aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —$SO_2$-alkyl, —$SO_2$-substituted alkyl, —$SO_2$-alkenyl, —$SO_2$-substituted alkenyl, —$SO_2$ cycloalkyl, $SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Alkenoxy" refers to the group "alkenyl-O—".

"Substituted alkenoxy" refers to the group "substituted alkenyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl , cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonyl" refers to the groups alkyl-$SO_2O$—, substituted alkyl-$SO_2O$—, alkenyl-$SO_2O$—, substituted alkenyl-$SO_2O$—, alkynyl-$SO_2O$—, substituted alkynyl-SO, O—, aryl-$SO_2O$—, substituted aryl-$SO_2O$—, cycloalkyl-$SO_2O$—, substituted cycloalkyl-$SO_2O$—, heteroaryl-$SO_2O$—, substituted heteroaryl-$SO_2$—, heterocyclic-$SO_2O$—, and substituted heterocyclic-$SO_2O$— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, amino carbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-hetero-cyclic, —SO$_2$-substituted heterocyclic and —SO$_2$NRR where R is hydrogen or alkyl.

"Alkynyl" refers to alkynyl group preferably having from 2 to 10 carbon atoms and more preferably 3 to 6 carbon atoms and having at least 1 and preferably from 1–2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-hetero-cyclic, —SO$_2$-substituted heterocyclic and —SO$_2$NRR where R is hydrogen or alkyl.

"Amidino" refers to the group H$_2$NC(=NH)— and the term "alkylamidino" refers to compounds having 1 to 3 alkyl groups (e.g., alkylHNC(=NH)—).

"Thioamidino" refers to the group RSC(=NH)— where R is hydrogen or alkyl.

"Amino" refers to the group —NH$_2$.

"Substituted amino" refers to the group —NRR, where each R group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R groups are not hydrogen; or the R groups can be joined together with the nitrogen atom to form a heterocyclic or substituted heterocyclic ring.

"Aminoacyl" refers to the groups —NRC(O)alkyl, —NRC(O)substituted alkyl, —NRC(O)cycloalkyl, —NRC (O)substituted cycloalkyl, —NRC(O)alkenyl, —NRC(O) substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the groups —NRSO$_2$alkyl, —NRSO$_2$ substituted alkyl, —NRSO$_2$cycloalkyl, —NRSO$_2$ substituted cycloalkyl, —NRSO$_2$alkenyl, —NRSO$_2$ substituted alkenyl, —NRSO$_2$alkynyl, —NRSO$_2$ substituted alkynyl, —NRSO$_2$aryl, —NRSO$_2$ substituted aryl, —NRSO$_2$heteroaryl, —NRSO$_2$ substituted heteroaryl, —NRSO$_2$heterocyclic, and —NRSO$_2$ substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the groups —NRSO$_2$O-alkyl, —NRSO$_2$O-substituted alkyl, —NRSO$_2$O-alkenyl, —NRSO$_2$O-substituted alkenyl, —NRSO$_2$O-alkynyl, —NRSO$_2$O-substituted alkynyl, —NRSO$_2$O-cycloalkyl, —NRSO$_2$O-substituted cycloalkyl, —NRSO$_2$O-aryl, —NRSO$_2$O-substituted aryl, —NRSO$_2$O-heteroaryl, —NRSO$_2$O-substituted heteroaryl, —NRSO$_2$O-heterocyclic, and —NRSO$_2$O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonylamino" refers to the groups —OSO$_2$NH$_2$, —OSO$_2$NRR, —OSO$_2$NR-alkyl, —OSO$_2$NR-substituted alkyl, —OSO$_2$NR-alkenyl, —OSO$_2$NR-substituted alkenyl, —OSO$_2$NR-alkynyl, —OSO$_2$NR-substituted alkynyl, —OSO$_2$NR-cycloalkyl, —OSO$_2$NR-substituted cycloalkyl, —OSO$_2$NR-aryl, —OSO$_2$NR-substituted aryl, —OSO$_2$NR-heteroaryl, —OSO$_2$NR-substituted heteroaryl, —OSO$_2$NR-heterocyclic, and —OSO$_2$NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amino carbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amino sulfonylamino" refers to the groups —NRSO$_2$NRR, —NRSO$_2$NR-alkyl, —NRSO$_2$NR-substituted alkyl, —NRSO$_2$NR-alkenyl, —NRSO$_2$NR-substituted alkenyl, —NRSO$_2$NR-alkynyl, —NRSO$_2$NR-substituted alkynyl, —NRSO$_2$NR-aryl, —NRSO$_2$NR-substituted aryl, —NRSO$_2$NR-cycloalkyl, —NRSO$_2$NR-substituted cycloalkyl, —NRSO$_2$NR-heteroaryl, and —NRSO$_2$NR-substituted heteroaryl, —NRSO$_2$NR-heterocyclic, and —NRSO$_2$NR-substituted heterocyclic, where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, amino carbonyloxy, amino carbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$ -alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$ heterocyclic, —OS(O)$_2$-substituted heterocyclic, —OS(O)$_2$—NRR where R is hydrogen or alkyl, —NRS(O)$_2$-alkyl, —NRS(O)$_2$ -substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O), —NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, oxycarbonylamino, oxythiocarbonylamino, —S(O)$_2$ -alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$ aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to a cycloalkyl and cycloalkenyl groups, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO,-heteroaryl, —SO$_2$-substituted heteroaryl, —SO$_2$,-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Cycloalkenoxy" refers to —O-cycloalkenyl groups.

"Substituted cycloalkenoxy" refers to —O-substituted cycloalkenyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted ,aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from oxygen, nitrogen and sulfur within the ring or oxides thereof. Such heteroaryl groups can have a single ring (e.g., pyridyl or furyl) or multiple condensed rings (e.g., indolizinyl or benzothienyl). Additionally, the heteroatoms of the heteroaryl group may be oxidized, i.e., to form pyridine N-oxides or 1,1-dioxo-1,2,5-thiadiazoles and the like. Preferred heteroaryls include pyridyl, pyrrolyl, indolyl, furyl, pyridazinyl, pyrimidinyl, pyrazinyl, 1-oxo-1,2,5-thiadiazolyl and 1,1-dioxo-1,2,5-thiadiazolyl. The term "heteroaryl having two nitrogen atoms in the heteroaryl ring" refers to a heteroaryl group having two, and only two, nitrogen atoms in the heteroaryl ring and optionally containing 1 or 2 other heteroatoms in the heteroaryl ring, such as oxygen or sulfur.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-hetero arylamino, mono- and di-substituted heteroarylamino, mono- and di-heterocyclic amino, mono- and di-substituted heterocyclic amino, unsymmetric di-substituted amines having different substituents, selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$-NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono-and di-arylamino, mono- and di-substituted arylamino, mono- and different-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl.

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Nitrogen containing heteroaryl" refers to a heteroary ring as defined above that contains at least one nitrogen atom in the ring. Such heteroaryl groups can have a single ring (e.g., pyridyl) or multiple condensed rings (e.g., indolizinyl). Additionally, the heteroatoms of the heteroaryl group may be oxidized, i.e., to form pyridine N-oxides or 1,1-dioxo-1,2,5-thiadiazoles and the like. Preferred nitrogen containing heteroaryls include pyridyl, pyrrolyl, indolyl, pyridazinyl, pyrimidinyl, pyrazinyl, 1-oxo-1,2,5-thiadiazolyl and 1,1-dioxo-1,2,5-thiadiazolyl. The term "heteroaryl having two nitrogen atoms in the heteroaryl ring" refers to a heteroaryl group having two, and only two, nitrogen atoms in the heteroaryl ring and optionally containing 1 or 2 other heteroatoms in the heteroaryl ring, such as oxygen or sulfur.

The term "nitrogen containing heteroaryl" also includes heteroaryl groups as defined above which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)₂-alkyl, —S(O)₂-substituted alkyl, —S(O)₂-cycloalkyl, —S(O)₂-substituted cycloalkyl, —S(O)₂-alkenyl, —S(O)₂-substituted alkenyl, —S(O)₂-aryl, —S(O)₂-substituted aryl, —S(O)₂-heteroaryl, —S(O)₂-substituted heteroaryl, —S(O)₂-heterocyclic, —S(O)₂-substituted heterocyclic, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamido, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO₂NRR where R is hydrogen or alkyl.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The compounds of this invention can be prepared in the manner described below using procedures known in the art and disclosed, for example, in U.S. patent application Ser. No. 09/489,377 and WO 00/18759 both of which are incorporated herein by reference in its entirety.

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichloro fluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1-R^6$, $Ar^1$, $L^1$, $Alk^1$, $Alk^2$, m, r, g, $Ar^2$, $R^a$ and R when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

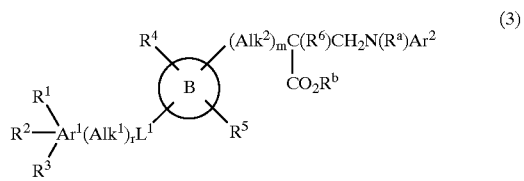

where $R^b$ is an alkyl group, for example a $C_{1-6}$alkyl group as described above.

The hydrolysis may be performed using either an acid or a base depending on the nature of $R^b$, for example an organic acid such as trifluoroacetic acid or an inorganic base such as lithium or potassium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (3) may be prepared by coupling an amine of formula (4)

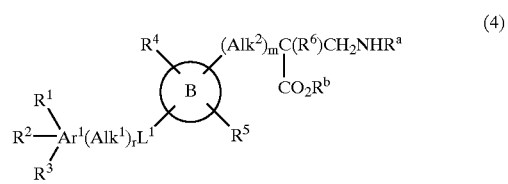

or a salt thereof with a reagent $Ar^2X^1$ where $X^1$ is a leaving group. Particular leaving groups represented by $X^1$ include for example halogen atoms such as fluorine, chlorine or bromine atoms or sulphonyloxy groups such as a methylsulphonyloxy group.

The coupling reaction may be performed using standard conditions for reactions of this type. Thus for example the reaction may be carried out in a solvent, for example an alcohol, e.g. methanol or ethanol, at a temperature from around ambient to the reflex temperature, optionally in the presence of a base, e.g. an organic base such as an amine, e.g. triethylamine or N,N-diisopropylethylamine, or a cyclic amine, such as N-methylmorpholine or pyridine.

In a further example compounds of formula (4) [$R^a$, $R^6$ are H,] can be converted into compounds of formula (5) by treatment with nitrous acid, or isoamyl nitrite in the presence of an acid source, for example acetic acid, in a halogenated hydrocarbon e.g. dichloromethane or chloroform at a temperature from ambient temperature to 60° C.

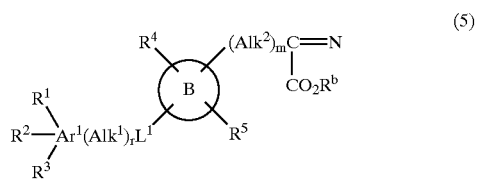

Esters of formula (3) can be obtained from diazo compounds of formula (5) by reaction with amines of formula $Ar^2R^aNH$ optionally in the presence of a catalyst, for example a rhodium (II) catalyst, for example rhodium (II)

acetate dimer, a copper (II) catalyst, for example copper (II) acetate or a palladium (II) catalyst, for example palladium (II) acetate in an organic solvent, e.g. toluene, at a temperature from around ambient to the reflex temperature.

Where desired, compounds of formula (4) may be linked to a suitable solid support, for example via their carboxylate group ($R^b$ is H), and subsequently converted to compounds of formula (1) linked to the solid support via the methods just described. Displacement from the resin by any convenient method for example by cleavage using an acid such as trifluoroacetic acid, then gives the desired compound of formula (1).

Particular examples of such solid-phase syntheses are given in the Examples herein.

The amines of formula (4) may be obtained from simpler, known compounds by one or more standard synthetic methods employing C—C bond formation substitution, 1,4-addition, oxidation, reduction or cleavage reactions. Particular C—C bond forming reactions include the Horner-Emmons and Wittig reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds. Additionally, although a number of the intermediates $Ar^2X^1$ for use in the coupling reaction described above are known, others can be derived therefrom using these standard synthetic methods.

Thus compounds of the invention and intermediates thereto may be prepared by alkylation, arylation or heteroarylation. For example, compounds containing a -$L^1H$, -$L^2H$, or -$L^3H$ group (where $L^1$, $L^2$ and $L^3$ is each a linker atom or group) may be treated with an alkylating agent:

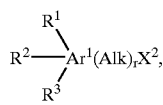

$(R^7)_n L^3 Alk^3_r X^2$ or $R^{7a}X^2$ respectively in which $X^2$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. P-toluenesulphonyloxy group, and $R^{7a}$ is an alkyl group.

The reaction may be carried out in the presence of a base such as a Carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as (tetrahydrofuran).

In another example, compounds containing a -$L^1H$, -$L^2H$ or -$L^3H$ group as defined above may be functionalised by acylation or thioacylation, for example by reaction with one of the alkylating agents just described but in which $X^2$ is replaced by a —C(O)$X^3$, C(S)$X^3$, —N($R^8$)CO$X^3$ or —N($R^8$)C(S)$X^3$ group in which $X^3$ is a leaving atom or group as described for $X^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation or thioacylation may be carried out under the same conditions with an acid or thioacid (for example one of the alkylating agents described above in which $X^2$ is replaced by a —CO$_2$H or —COSH group) in the presence of a condensing agent, for example a diimide such as 1-(3-dimethylaminopropyl)-3-ethylcarbodiimide or N,N-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $X^2$ is replaced by a —S(O)Hal or —SO$_2$Hal group, in which Hal is a halogen atom such as chlorine atom, in the presence of a base, for example an inorganic base such as sodium hydride in a solvent such as an amide, e.g. a substituted amide such as dimethylformamide at for example ambient temperature.

In another example, compounds containing a -$L^1H$, -$L^2H$ or -$L^3H$ group as defined above may be coupled with one of the alkylation agents just described but in which $X^2$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —CO$_2R^8$ or —CO$_2Alk^5$ in the compounds may be converted to the corresponding acid (—CO$_2$H) by acid- or base-catalysed hydrolysis depending on the nature of the groups $R^8$ or $Alk^5$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —OR$^8$ or —OR$^{14}$ groups, where $R^8$ or $R^{14}$ each represents an alkyl group such as methyl group, in compounds of formula (1) may be cleaved to the corresponding alcohol —OH by reaction with boron tribromide in a solvent such as a halogenated hydrocarbon, e.g. dichloromethane at a low temperature, e.g. around -78° C.

Alcohol [—OH] groups may also be obtained by hydrogenation of a corresponding —OCH$_2R^{14}$ group, where $R^{14}$ is an aryl group, using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester (—CO$_2Alk^5$ or CO$_2R^8$) or aldehyde (—CHO) by reduction, using for example a complex metal hydride such as lithium aluminium hydride or sodium borohydride in a solvent such as methanol.

In another example, alcohol —OH groups in the compounds may be converted to a corresponding —OR$^8$ group by coupling with a reagent $R^8$OH in a solvent such as tetrahydrofuran in the presence of a phosphine, e.g. triphenylphosphine and, an activator such as diethyl-, diisopropyl-, or dimethylazodicarboxylate.

Aminosulphonylamino (—NHSO$_2$NH$_2$) groups in the compounds may be obtained, in another example, by reaction of a corresponding amine (—NH$_2$) with sulphamide in the presence of an organic base such as pyridine at an elevated temperature, e.g. the reflux temperature.

In a further example amine (—NH$_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine (—$NH_2$) groups in compounds of formula (1) may be obtained by hydrolysis from a corresponding imide by reaction with hydrazine in a solvent such as an alcohol, e.g. ethanol at ambient temperature.

In another example, a nitro (—$NO_2$) group may be reduced to an amine (—$NH_2$), for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C. in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a linker group $L^1$, $L^2$ or $L^3$ may be oxidised to the corresponding sulphoxide or sulphone using an oxidizing agent such as a peroxy acid, e.g. 3-chloroperoxybenzoic acid, in an inert solvent such as a halogenated hydrocarbon, e.g. dichloromethane, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produce d from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallization and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystallization and other conventional separation procedures may also be used with intermediates or final products where it is desired to obtain a particular geometric isomer of the invention.

The following examples illustrate synthetic methods which could be used in the methods of this invention by merely replacing a nitrogen containing heteroaryl reagent with the phenyl reagents used therein. All temperatures are in ° C. The following abbreviations are used:

MeOH - methanol;
DCM - dichloromethane;
DIPEA - N,N-diisopropylethylamine;
LDA - lithium N,N-diisopropylamide;
mCPBA - 3-chloroperoxybenzoic acid
All NMR's were obtained at 300 mHz.
BOC - butoxycarbonyl;
AcOH - acetic acid;
DMF - dimethylformamide;

INTERMEDIATE 1

3,5-Dichloropyridine-4-carboxylic acid

A solution of 3,5-dichloropyridine (5.00 g, 33.8 mmol) in THF (25 ml) was added to a solution of LDA [generated from nBuLi (2.5M solution hexanes, 14.9 ml, 37.2 mmol) and diisopropylamine (4.10 g, 5.7 ml, 40.6 mmol)] in THF (25 ml) at −78° then $CO_2$ gas was bubbled through to give a clear brown solution that slowly gave a precipitate, warmed to room temperature over 2 h, then quenched with water (20 ml) and partitioned between diethylether (100 ml) and 1M NaOH (100 ml). The aqueous layer was separated and acidified to pH1 with concentrated hydrochloric acid and then extracted with 10% MeOH in DCM (100 ml×3). The combined organic layers were dried ($MgSO_4$) and the solvent removed in vacuo to give a brown solid that was recrystallized from ethanol and dried under vacuum to give the title compound as pinkish crystals (2.63 g, 41%): δH (DMSO $d_6$) 8.72 (2H, s).

INTERMEDIATE 2

(S)-Ethyl-3-[4-(3,5-dichloropyrid-4-ylcarboxamido)phenyl]-2-(t-butoxycarbonylamino)propionate A slurry of Intermediate 1 (51.2 g, 0.267 mol) in DCM (195 ml) and thionyl chloride (195 ml, 2.67 mol) was treated with DMF (5 drops) and heated to reflux for 4 h. The reaction was concentrated in vacuo and azeotroped with toluene (2×50 ml) to give the acid chloride derivative of intermediate 1 as a yellow solid which was used without further purification. A solution of (S)-ethyl-3-(4-aminophenyl)-2-(t-butoxycarbonylamino)propionate (130.8 g, 0.425 mol) in DCM (800 ml) was cooled to 0° and treated with NMM (56.0 ml, 0.51 mol), stirred 5 minutes and then a solution of the acid chloride (98.3 g, 0.468 mol) in DCM (200 ml) was added dropwise keeping the reaction temperature below 5°. The reaction was stirred for 1 h, quenched with $NaHCO_3$ solution (500 ml), the organic layer separated, washed with $NaHCO_3$ solution (500 ml), 10% citric acid solution (500 ml) and $NaHCO_3$ solution (500 ml), dried ($MgSO_4$) and concentrated in vacuo to give a yellow solid which was recrystallised (EtOAc/Hexane) to give the title compound (140 g, 69%): δH (DMSO $d_6$) 8.80 (2H, s), 7.55 (2H, d, J 8.5 Hz), 7.23 (2H, d, J 8.5 Hz), 4.00 (3H, m), 3.40 (2H, br. s), 2.90 (1H, m), 2.80 (1H, m), 1.30 (9H, s), 1.25 (3H, t); m/z ($EI^+$, 70V) 504.

INTERMEDIATE 3

(S)-Ethyl-3-[4-(3,5-dichloropyrid-4-ylcarboxamido) phenyl]-2-aminopropionate hydrochloride A solution of Intermediate 2 (70.0 g, 0.146 mol) in EtOAc (500 ml) and 1,4-dioxan (50 ml) was treated with a solution of HCl in EtOAc (500 ml, 3M), and stirred at room temperature for 4 h. The reaction was concentrated in vacuo to give a yellow solid which was triturated with $Et_2O$ then recrystallised (EtOAc/hexane) to give the title compound (59.3 g, 92%): δH (DMSO $d_6$) 11.10 (1H, s), 8.70 (2H, s), 7.55 (2H, d, J 8.4 Hz), 7.25 (2H, d, J 8.4 Hz), 4.10 (3H, m), 3.10 (2H, m), 1.10 (3H, m); m/z (EI$^+$, 70V) 382.

INTERMEDIATE 4

(S)-Methyl-3-[4-(3,5-dichloropyrid-4-ylcarboxamido)phenyl]-2-aminopropionate hydrochloride The title compound was prepared in a similar manner to Intermediate 3 starting from (S)-methyl-3-(4-aminophenyl)-2-(t-butoxycarbonylamino)propionate and Intermediate 1: δH (DMSO $d_6$) 11.08 (1H, s), 8.77 (2H, s), 8.73 (3H, br. m), 7.63 (2H, d, J 8.5 Hz), 7.25 (2H, d, J 8.5 Hz), 4.24 (1H, m), 3.70 (3H, s), 3.16 (2H, m); m/z (EI$^+$, 70V) 368 and 370.

INTERMEDIATE 5

3,5-Dichloro-4-hydroxymethylpyridine

A solution of 3,5-dichloropyridine-4-carboxaldehyde (1.34 g, 7.6 mmol) in MeOH (10 ml) was treated with $NaBH_4$ (0.29 g, 7.6 mmol) and stirred at room temperature for 2 h. The reaction was quenched with water (5 ml) and concentrated in vacuo. The residue was partitioned between EtOAc (20 ml) and 10% HCl (10 ml). The aqueous layer was extracted with EtOAc and the combined organic extracts washed with 10% $NaHCO_3$ solution, dried ($MgSO_4$) and concentrated in vacuo to give the title compound as a white solid (1.05 g, 78%): δH (CDCl$_3$) 8.52 (2H, s), 4.94 (2H, br. s), 2.28 (1H, br. s).

INTERMEDIATE 6

3,5-Dichloro-4-bromomethylpyridine

A solution of Intermediate 5 (0.50 g, 2.80 mmol) in DCM (10 ml) was treated with thionyl bromide (3,51 g, 1.32 ml, 16.9 mmol) and heated to reflux for 3 h. The reaction was quenched with 10% $NaHCO_3$ solution (10 ml) and extracted with DCM (25 ml). The organic layer was dried ($MgSO_4$) and concentrated in vacuo to give the title compound as a yellow oil that solidified on standing (0.65 g, 96%) and was used without further purification: δH (CDCL$_3$) 8.50 (2H, s), 4.63 (2H, s); m/z (EI$^+$, 60V) 242.

INTERMEDIATE 7

(S)-Ethyl [O-(3,5-dichloropyrid-4-yl)methyl]-L-tyrosine hydrochloride

The title compound was obtained by reaction of N-Boc-L-tyrosine ethyl ester with Intermediate 6 in the presence of sodium hydride, followed by Boc deprotection, using methods well known to a person skilled in the art: δH (DMSO $d_6$) 8.79–8.60 (3H, m), 7.20 (2H, d, J 8.6 Hz), 7.00 (2H, d, J 8.6 Hz), 5.21 (2H, s), 4.34–4.20 (1H, m), 3.67 (3H, s); m/z (EI$^+$, 70V) 355 and 357.

INTERMEDIATE 8

S-Ethyl 3-(4-nitrophenyl)-2-(6-chloropyrimidin-4-ylamino)propionate

A solution of 4-vitro-L-phenylalanine ethyl ester (3.22 g, 13.53 mmol), DIPEA (2.35 ml, 1.75 g, 13.56 mmol) and 4,6-dichloropyrimidine (2.02 g, 13,55 mmol) in absolute ethanol (16 ml) was stirred at 70° for 18H under $N_2$. The volatiles were removed in vacuo and the residue partitioned between EtOAc (70 ml) and water (40 ml). The phases were separated and the aqueous phase re-extracted with EtOAc (2×30 ml). The combined organic extracts were washed with brine (10 ml), dried ($Na_2SO_4$) and evaporated in vacuo to afford a dark oil. Chromatography (silica, 2% MeOH/DCM) afforded the title compound as an orange oil which slowly solidified (4.03 g, 85%); δH (CDCl$_3$,) 8.39 (1H, s), 8.13 (1H, d, J 8.7 Hz), 7.28 (2H, d, J 8.7 Hz), 6.43 (1H, s), 5.55 (1H, br d, J 7.0 Hz), 5.10–5.00 (1H, br m), 4.21 (2H, q, 17.1 Hz), 3.27 (1H, dd, J 13.8, 6.0 Hz), 3.27 (1H, dd, J 13.8, 5.7 Hz) and 1.26 (3 H, t, J 7.1 Hz); m/z (EI$^+$, 100V) 351.

INTERMEDIATE 9

S-Ethyl 3-(4-aminophenyl)-2-(6-chloropyrimidin-4-ylamino)propionate

A mixture of Intermediate 8 (1 g, 2.85 mmol) and 10% palladium on activated carbon (100 mg) in absolute ethanol (40 ml) was stirred under a hydrogen atmosphere (balloon) at room temperature for 1.5 h. After degassing and $N_2$ flushing, the catalyst was removed by filtration through a Celite® pad and washed with DCM. The filtrate was evaporated in vacuo and the obtained yellow oil subjected to chromatography (silica: 3% MeOH/DCM). The title compound was isolated as a yellow oil (0.42 g, 46%) δH (CDCl$_3$) 8.33 (1H, s), 6.86 (2H, d, J 8.4 Hz), 6.56 (2H, d, J 8.4 Hz), 6.30 (1H, s), 5.27 (1H, br s), 4.84 (1H, br s), 4.19 (2H, q, J 7.1 Hz), 3.64 (2H, br s), 3.10 (1H, dd, J)14.0, 5.6 Hz), 3.01 (1H, dd, J 14.0, 6.1 Hz) and 1.26 (3H, t, J 7.1 Hz); m/z (EI$^+$, 100V) 321.

INTERMEDIATE 10

S-Ethyl 3-[4-dichloropyrid-4-ylcarboxamidol-phenyl]-2-(4-methoxy-6-chloro-1,3,5-triazin-2-ylamino)propionate Intermediate 3 (0.5 g, 1.19 mmol) in dry acetonitrile (5 ml) under nitrogen was added to 2,4 dichloro-6-methoxy-1,3,5-triazine (0.26 g, 1.43 mmol). The mixture was cooled to −30° and DIPEA (0.46 ml) was added slowly over 10 min. The reaction was allowed to warm to 5° over 2 h and then ethyl acetate and aqueous sodium bicarbonate were added and the mixture shaken and separated. The organic layer was washed with water, dried ($MgSO_4$) and the solvent removed in vacuo. The product was purified by flash chromatography (silica; EtOAC/Hexane 1:1) to afford the title compound as a white solid (0.53 g, 85%): δH (DMSO $d_6$) 10.55 (1H, s), 8.70 (2H, s), 8.51–8.40 (1H, m), 7.50 (2H, d, J 8.4 Hz), 7.29 (2H, d, J 8.4 Hz), 4.60 (1H, m), 4.12 (2H, d, J 8.4 Hz), 3.87 (3H, s), 3.23–3.15 (2H, m), 1.16 (3H, t, J 7.2 Hz); m/z (EI$^+$, 70V) 527.

INTERMEDIATE 11

S-Ethyl 3-(4-hydroxyphenyl)-2-[(4,6-dimethoxy-1,3, 5-triazin-2-yl)amino]propionate A mixture of L-tyrosine ethyl ester hydrochloride (0.50 g, 2.0 mmol) and DIPEA (0.74 ml, 4.4 mmol) in $CH_3CN$ (8 ml) was stirred at room temperature for 15 minutes and then 2-chloro-4,6-dimethoxy-1,3,5-triazine (0.43 g, 2.2 mmol) was added, and the reaction stirred overnight then concentrated in vacuo. The residue was partitioned between EtOAc (50 ml) and $NaHCO_3$ solution (50 ml). The organic layer was washed with 10% citric acid solution (50 ml), $NaHCO_3$ solution (50 ml) and water (50 ml), dried ($MgSO_4$) and concentrated in vacuo to give the title compound as a colourless gum (0.48 g, 68%): δH (DMSO $d_6$) 6.90 (2H, d), 6.65 (2H, d), 5.90 (1H, m), 4.90 (1H, m), 4.10 (2H, m), 3.95 (3H, s), 3.90 (3H, s), 3.10 (2H, m), 1.20 (3H, t, J 7.1 Hz); m/z ($EI^+$, 70V) 349.

INTERMEDIATE 12

2,3-Bis(propylsulphonyl)pyrazine

Propanethiol (1.99 ml, 22 mmol) was added to a suspension of sodium hydride (60% in mineral oil, 880 mg, 22 mmol) in THF (50 ml). After 10 min, a solution of 2,3-dichloropyrazine (1.49 g, 10 mmol) in THF (50 ml) was added and the mixture stirred at room temperature overnight. The reaction was quenched with water and the solvent removed in vacuo. The residue was dissolved in EtOAc, washed with water, 10% NaOH solution and brine, dried ($Na_2SO_4$) and evaporated in vacuo to give a pale yellow oil (2.7 g). This was dissolved in DCM (100 ml) at 0°, and mCPBA (57–86%, ~40 mmol, 12.1 g) was added in portions. The mixture was stirred at room temperature overnight, then treated with $Na_2SO_3$ (aq). The organic phase was washed with $NaHCO_3$ (aq), dried ($Na_2SO_4$) and evaporated in vacuo to give the title compound as a white solid (3.18 g): δH ($CDCl_3$) 8.94 (2H, s), 3.68–3.63 (4H, m), 2.10–1.88 (4H, m), 1.10 (6H, t, J 7.4 Hz); m/z ($EI^+$, 70V) 293.

INTERMEDIATE 13

4,6-Bis(propylsulphonyl)pyrimidine

The title compound was prepared by the method of Intermediate 12 from 4,6-dichloropyrimidine: δH (DMSO $d_6$) 9.77 (1H, d, J 1.3 Hz), 8.40 (1H, d, J 1.3 Hz), 3.61–3,56 (4H, m), 1.75–1.65 (4H, m), 0.97 (6H, t, J 7.5 Hz); m/z ($EI^{+'}$, 70V) 293.

INTERMEDIATE 14

2-Chloro-3-phenoxyguinoxaline

A solution of phenol (564 mg, 6 mmol) in THF (5 ml) was added to a suspension of sodium hydride (60% in mineral oil, 240 mg, 6 mmol) in THF (10 ml). After 10 min 2,3-dichloroquinoxaline (995 mg, 5 mmol) was added. The mixture was stirred for 3 days. The solvent was removed in vacuo, the residue was dissolved in EtOAc, washed with NaOH (1M), dried ($Na_2SO_4$) and evaporated in vacuo to give a yellow solid. Recrystallisation from diisopropylether gave the title compound as off-white needles: δH (DMSO $d_6$) 8:01–7.98 (1H, m), 7.77–7.67 (3H, m), 7.53–7.48 (2H, m), 7.37–7.30 (3H, 10 m); m/z ($EI^+$, 70V) 257.

INTERMEDIATE 15

Ethyl 2-(diethoxyphosphoryl)-3-(4-nitrophenyl)propionate

Ethyl 2-(diethoxyphosphoryl)acetate (5.0 ml, 25.2 mmol) was added to a suspension of sodium hydride (60% in mineral oil, 1.10 g, 27.6 mmol) in THF (40 ml) at 0°. After 30 min at room temperature, a solution of 4-nitrobenzylbromide (5.42 g, 25.2 mmol) in THF (40 ml) was added over 30 min. The reaction mixture was stirred for 2 h at room temperature, quenched with water and partitioned between $Et_2O$ and water. The aqueous phase was extracted with $Et_2O$ and the combined organic layers washed with brine, dried ($MgSO_4$) and evaporated in vacuo. Column chromatography (silica; MeOH/DCM, 1:49) gave the title compound as a pale yellow oil (2.0 g): δH ($CDCl_3$) 8.13 (2H, d, J 8. δHz), 7.37 (2H, d, J 8. δHz), 4.23–4.06 (6H, m), 3.37–3.20 (3H, m), 1.35 (6H, t, J 7.1 Hz), 1.16 (3H, t, ,) 7.1 Hz): m/z ($EI^+$, 70V) 360.

INTERMEDIATE 16

Ethyl 3-(4-aminophenyl)-2-(diethoxyphosphoryl)propionate

A mixture of Intermediate 15 (4.5 g, 12.0 mmol) and tin(II) chloride dihydrate (15 g) in ethanol was stirred overnight. The solvent was removed in vacuo. DCM (100 ml) and 1M NaOH (100 ml) was added and the white precipitate removed by filtration. The organic phase of the filtrate was separated and evaporated in vacuo. The residue was acidified to pH1 with dil. HCl and extracted with diethyl ether. The aqueous phase was basified to pH10 with $Na_2CO_3$ and extracted with EtOAc. The EtOAc extracts were dried ($MgSO_4$) and evaporated in vacuo. Column chromatography (silica; MeOH/DCM 5:95) gave the title compound as a yellow oil (2.19 g): δH ($CDCl_3$) 6.98 (2H, d, J 8.2 Hz), 6.59 (2H, d, J, 8.5 Hz), 4.22–4.04 (6H, m), 3.25–3.02 (3H, m), 1.34 (6H, m), 1.16 (3H, t, J 7.1 Hz): m/z ($EI^+$, 70V) 330.

INTERMEDIATE 17

Ethyl 3-[4-(3,5-Dichloropyrid-4-ylcarboxamido)phenyl]-2 (diethoxyphosphoryl)propionate A solution of 3,5-dichloropyrid-4-ylcarbonyl chloride (1.41 g, 6.7 mmol) in THF (10 ml) was added to a solution of Intermediate 16 (2.19 g, 6.7 mmol) and NMM (0.88 ml, 8.0 mmol) in THF (40 ml). The mixture was stirred at room temperature overnight then partitioned between EtOAc and water. The aqueous layer was extracted with EtOAc and the combined organic layers washed with 10% aqueous HCl and $NaHCO_3$ (aq), dried ($MgSO_4$) and evaporated in vacuo. Column chromatography (silica; MeOH/DCM 5:95) gave the title compound as a yellow oil (2.61 g): δH ($CDCl_3$) 8.55 (2H, s), 8.08 (1H, br. s), 7.55 (2H, d, J 8.5 Hz), 7.21 (2H, d, J 8.5 Hz), 4.19–4.08 (6H, m), 3.25–3.10 (3H, m), 1.35 (3H, t, J 7.1 Hz), 1.34 (3H, t, J 7.1 Hz), 1.18 (3H, t, J 7.1 Hz).

INTERMEDIATE 18

Ethyl 2-[4-(3,5-dichloropyrid-4-ylcarboxamido)benzyl]acrylate

A mixture of Intermediate 17 (1.74 3.6 mmol), potassium carbonate (1.48 g, 10.7 mmol) and aqueous paraformaldehyde (37% wt, 10 ml) was heated at reflux for 4 h. The mixture was partitioned between EtOAc and water. The aqueous phase was extracted with EtOAc and the combined organic layers washed with brine, dried ($MgSO_4$) and evaporated in vacuo. Column chromatography (silica; EtOAc/Hexane 50:50) gave the title compound as a white solid (1.09 g): δH ($CDCl_3$) 8.52 (1H, br. s), 8.44 (2H, br. s), 7.49 (2H, d, J 8.5 Hz), 7.18 (2H, d, J 8.5 Hz), 6.22 (1H, br, s), 5.49 (1H, br. s), 4.15 (2H, q, J 7.2 Hz), 3.60 (2H, br. s), 1.27 (3H, t, J 7.2 Hz).

INTERMEDIATE 19

Ethyl 3-amino-2-[4-(3,5-dichloropyrid-4-ylcarboxamido benzyl]propionate

A mixture of Intermediate 18 (1.50 g, 3.7 mmol) and liquid ammonia (10 ml) was kept in a sealed vessel for 3 d at room temperature. Column chromatography (silica; MeOH/DCM 1:9 to 1:4) gave the title compound as a colourless oil (1.00 g): δH (DMSO $d_6$) 10.83 (1H, s), 8.78 (2H, d, J 8.5 Hz), 7.54 (2H, d, J 8.5 Hz), 7.16 (2H, d, J 8.5 Hz), 4.00 (2H, q, J 7.1 Hz), 3.29 (2H, br. s), 2.83–2.61 (5H, m), 1.10 (3H, t, J 7.1 Hz): m/z ($EI^+$, 70V) 396.

INTERMEDIATE 20

Ethyl 2-diazo-3-[4-(3,5-dichloropyrid-4-ylcarboxamido)phenyl]propionate

A solution of the compound of Intermediate 3 (free amine) (2.80 g, 7.40 mmol), glacial acetic acid (1.4 ml, 24.50 mmol), isoamyl nitrite (1 ml, 7.40 mmol) in 100 ml anhydrous chloroform were stirred at reflux under nitrogen for 1 h. On cooling the solution was washed with water (2×25 ml), saturated $NaHCO_3$ (2×25 ml), water (2×25 ml), dried ($Na^2SO_4$) and evaporated in vacuo to afford the title compound as a yellow solid (2.1 g, 100%): δH ($CDCl_3$) 8.56 (2H, s), 7.72 (1H, br. s), 7.55 (2H, d, J 8.5 Hz), 7.26 (2H, d, J 8.5 Hz), 4.22 (2H, J, 7.1 Hz), 3.62 (2H, s), 1.25 (3H, t, J 7.1 Hz).

INTERMEDIATE 21

5-Chloro-2-(2,5-dimethylpyrrol)-1-yl)pyridine

2-Amino-5-chloropyridine (10.0 g, 77 mmol), acetonyl acetone (8.8 g, 77 mmol) and a catalytic amount of p-toluenesulphonic acid in anhydrous toluene (250 ml) was heated to reflux for 5 h under Dean and Stark conditions. The solvent was removed in vacuo, the residue slurried in hexane (250 ml), filtered through celite and the solvent removed in vacuo to give the title compound as a yellow oil (16.0 g): δH ($CDCl_3$) 8.57 (1H, dd, J 2.7, 0.6 Hz), 7.78 (1H, dd, J 8.4, 2.7 Hz), 7.17 (1H, m, J 7.5, 0.5 Hz), 5.91 (2H, s), 2.14 (6H, s).

INTERMEDIATE 22

5-Chloro-4-propylthio-2-(2,5-dimethylpyrrol-1-yl)-pyridine

To a solution of LDA (12.3 mmol) in anhydrous toluene (6 ml) at −78° under nitrogen was added Intermediate 21 (2.3 g, 11.2 mmol) in THF (6 ml) dropwise over 15 min. After stirring a further 15 min at this temperature n-propyl disulfide (1.92, 12.8 mmol) in THF (2 ml) was added dropwise maintaining the temperature at −78°. On completion of the addition the reaction was allowed to warm to room temperature and quenched with 10% $NH_4Cl$ solution, diluted with EtOAc (50 ml) and the phases separated. The organic phase was washed with water (2×10 ml), dried ($MgSO_4$) and the solvent removed in vacuo. The residue was purified by chromatography (silica; 2% EtOAc/Hexane) to give the title compound (2.9 g) as a yellow solid: δH ($CDCl_3$) 8.39 (1H, s), 7.00 (1H, s), 5.92 (2H, s), 2.91 (2H, d, J 7.4 Hz), 2.15 (6H, s), 1.74 (2H, m), 1.09 (3H, t, J 7.4 Hz).

INTERMEDIATE 23

2-Amino-5-Chloro-4-proylthiopyridine

Intermediate 22 (1.3 g, 4.6 mmol) and hydroxylamine hydrochloride (1.6 g, 23 mmol) were heated to reflux in EtOH (12 ml) and water (3.5 ml) for 16 h. The cooled solution was poured onto conc HCl (12 ml)/water (48 ml) and the resulting solid filtered, washed with water and dried to give the title compound as a brown solid (550 mg): δH ($CDCl_3$) 8.11 (1H, s), 6.91 (1H, s), 3.01 (2H, t, J 7.3 Hz), 1.64 (2H, m), 1.00 (3H, t, J 7.3 Hz))): m/z ($EI^+$, 70V) 203.

INTERMEDIATE 24

Resin bound (S)-2-(9-Fluorenylmethoxycarbonylaminol-3-[4-(3,5-dichloropyrid-4-yl carboxamido)phenyl]propanoic acid Paramax Wang resin (Advanced Chemtech, 8.0 g, 0.69 mmol/g, 5.52 mmol equivalent) in DCM (100 ml) was treated with N-α-FMOC-4-nitro-L-phenylalanine (11.93 g, 27.6 mmol), diisopropylcarbodiimide (4.32 ml, 27.6 mmol) and 4-N,N-dimethylaminopyridine (0.67 g, 5.52 mmol) and mixture was agitated at room temperature for 16 h. The resin was filtered and washed with DMF, methanol and DCM, then air-dried. The resin was then treated with stannous chloride dihydrate (12.5 g, 55.2 mmol) in DMF (100 ml) at room temperature for 6 h, washed with DMF, methanol and DCM, then air dried overnight. The resin was treated with pyridine (4.44 ml, 55.2 mmol), 3,5-dichloropyrid-4-carbonyl chloride 3,52 g, 16.56 mmol) and 4-N,N-dimethylamino pyridine (0.67 g, 5.52 mmol) in DCM (100 ml). The reaction mixture was agitated at room temperature for 16 h. The resin was then washed with DMF, methanol and DCM, then with two 50 ml portions of a 10% solution of pyridine in DMF (100 ml). The resin was further washed with hot ethanol (2×100 ml), DMF, methanol and DCM then air-dried to give the title compound.

INTERMEDIATE 25

Resin bound 3-[4-(3,5-dichloropyrid-4-ylcarboxamido)phenyl]-2-diazopropanoic acid A portion of Intermediate 24 (3.0 g) was treated twice with a 20% solution of piperidine in DMF (100 ml), once for 5 min and once for 15 min. The resin was washed with DMF, methanol and DCM. This material was treated with isoamyl nitrite (1.79 ml, 12.30 mmols) and acetic acid (0.074 ml, 1.23 mmols) in anhydrous chloroform (70 ml) for 1 hr, then filtered and washed with DMF, methanol and DCM then finally air dried to give the title compound.

EXAMPLE 1

S-Methyl 3-[4-(3,5-dichloropyrid-4-ylcarboxamido)phenyl]-2-(4,6-dimethoxy-1,3,5-triazin-2-ylamino)propionate A solution of Intermediate 4 (330 mg, 0.90 mmol), DIPEA (163 μl, 121 mg, 0.94 mmol), and 2-chloro-4,6-dimethoxy-1,3,5-triazine (233 mg, 1.32 mmol) in MeOH (2 ml) was stirred under gentle reflux for 7 h under $N_2$. The volatiles were removed in vacuo and the residue partitioned between EtOAc (80 ml) and saturated aqueous $NaHCO_3$ (30 ml). The phases were separated and the aqueous layer re-extracted with EtOAc (40 ml). The combined organic extracts were washed with brine (10 ml), dried ($Na_2SO_4$) and evaporated in vacuo to afford a straw-coloured oil. Chromatography (silica; 4% MeOH/DCM) afforded the title compound as a colourless foam (330 mg, 73%): δH ($CDCl_3$) 8.46 (2H, s), 8.32 (1H, s), 7.51 (2H, d, J 8.4 Hz), 7.12 (2H, d, J 8.4 Hz), 6.17 (2H, d, J 8.0 Hz), 5.00 (1H, d, J 13.8, 6.0 Hz), 3.92 (3H, s), 3.89 (3H, s) and 3.75 (3H, s); m/z ($EI^+$, 160V) 507, 509.

EXAMPLE 2

S-3-[4-(3,5-Dichloropyrid-4-ylcarboxamido)phenyl]-2-(4,6-dimethoxy-1,3,5-triazin-2-ylamino)propanoic acid A solution of the compound of Example 1 (300 mg, 0.59 mmol) and $LiOH.H_2O$ (0.88 mmol) in dioxane (2 ml), MeOH (1 ml) and water (2 ml) was stirred at room temperature for 1 H. The pH was made acidic with a few drops of AcOH and the volatiles removed in vacuo. The residue was chromatographed [silica; DCM (400→200), MeOH (20), AcOH (3), $H_2O$ (2)] affording the product as a colourless oil. Freeze drying from aqueous 5 MeOH gave the title compound as a white amorphous solid (215 mg, 76%). δH ($d_6$ DMSO) 10.84 (1H, s), 8.77 (2H, s), 8.10 (1H, d, J 8.0 Hz), 7.54 (2H, d, J 8.4 Hz), 7.29 (2H, d, J 8.4 Hz), 4.58–4.48 (1H, m), 3.80 (3H, s), 3.78 (3H, s), 3.12 (1H, dd, J 14.0, 4.7 Hz) and 2.98 (1H, dd, J 14, 10.2 Hz). m/z ($EI^+$ 100V), 493, 495, 497.

EXAMPLE 3

S-Ethyl 3-[4-(3,5-dichloropyrid-4-ylcarboxamido)phenyl]-2-(6-chloropyrimidin-4-ylamino)propionate 3,5-Dichloropyrid-4-carbonyl chloride (289 mg, 1.37 mmol) was added to a stirred solution of Intermediate 9 (400 mg, 1.25 mmol) and NMM (150 μl, 139 mg, 1.37 mmol) in dry DCM (10 ml). After stirring for 1 h at room temperature under $N_2$, the reaction mixture was partitioned between DCM (70 ml) and saturated aqueous $NaHCO_3$ (30 ml). The phases were separated and the aqueous layer re-extracted with DCM (50 ml). The combined organic extracts were washed with brine (10 ml), dried ($Na^2SO_4$) and evaporated in vacuo. The obtained orange oil was chromatographed (silica; 5% MeOH/DCM) to afford the title compound as a straw-coloured foam (504 mg, 82%); δH ($CDCl_3$,) 8.48 (2H, s), 8.41 (1H, s), 8.32 (1H, s), 7.48 (2H, d, J 8.4 Hz), 7.08 (21H, d, J 8.4 Hz), 6.38 (1H, s), 5.72 (1H, br s), 4.96 (1H, br s), 4.22 (2H, q, J 7.1 Hz), 3.25 (1H, dd, J 14.0, 5.5 Hz), 3.14 (1H, dd, J 14.0, 5. δHz) and 1.21 (3H, t, J 7.1 Hz); m/z ($EI^+$, 160V) 496.

EXAMPLE 4

S-3-[4-(3,5-Dichloropyrid-4-ylcarboxamid)ophenyl]-2-(6-chloropyrimidin-4-ylamino)propanoic acid A solution of Example 3 (475 mg, 0.96 mmol) and $LiOH.H_2O$ (40 mg, 0.96 mmol) in dioxane (5 ml), MeOH (3 ml) and water (3 ml) was stirred at room temperature for 2.5 h. A few drops of AcOH were added and the volatiles removed in vacuo. The residue was chromatographed [silica; DCM (200), MeOH (20), AcOH (3), $H_2O$ (2)] to afford the product as a slightly yellow oil. The oil was dissolved in a small volume of MeOH, diluted with water and freeze-dried to give the title compound as an off-white amorphous solid (290 mg, 65%); Found: C, 47.67; H, 2.9; N, 14.65. $C_{19}H_{14}Cl_3N_5O_3.0.66H_2O$ requires C, 47.67; H, 3.23; N, 14.63%. δH ($d_6$ DMSO) 10.86 (1H, s), 8.78 (2H, s), 8.26 (1H, s), 7.98 (1H, br d, J 7.6 Hz), 7.55 (2H, d, J 8.2 Hz), 7.25 (2H, d, J 8.2 Hz), 6.66 (1H, s), 4.76 (1H, br s), 3.16 (1H, dd, J 13.9, 4.7 Hz) and 2.98 (1H, dd, J 13.9, 8.9 Hz); m/z ($EI^+$, 160V) 468.

EXAMPLE 5

S-Ethyl 3-[4-(3,5-dichloropyrid-4-ylcarboxamido)-phenyl]-2-(6-propylthiopyrimidin-4-ylamino)propionate A solution of Intermediate 3 (2.0 g, 4.8 mmol), DIPEA (1.29 g, 1.74 ml, 10 mmol) and 4-chloro-6-propylthiopyrimidine (1.08 g, 5.7 mmol) in 2-ethoxyethanol (8 ml) was heated at 110° for 2 days and 130° for 2 days under nitrogen. The volatiles were removed in vacuo and the dark oil partitioned between EtOAc (100 ml) and 5% aqueous citric acid (40 ml). The phases were separated and the aqueous layer re-extracted with EtOAc (2×30 ml). The combined organic extracts were washed consecutively with saturated aqueous $NaHCO_3$ (20 ml), water (20 ml), brine (20 ml), dried ($Na_2SO_4$) and treated with activated carbon, filtered and evaporated in vacuo. The obtained oil was purified by chromatography (silica; 2–3% MeOH/DCM) to afford the title compound (together with 20% of the ethoxyethyl ester analogue) as a pale yellow foam (1.26 g, 49%): δH ($CDCl_3$) 8.56 (2H, s), 8.38 (1H, s), 7.68 (1H, s), 7.53 (2H, d, J 8.6 Hz), 7.13 (2H, d, J 8.6 Hz), 6.20 (1H, s), 5.23–5.12 (1H, m), 5.00–4.84 (1H, m), 4.21 (2H, q, J 7.1 Hz), 3.26 (1H, d, J 14.0, 5.3 Hz), 3.15 (1H, d, J, 14.0, 5.7 Hz), 3.06 (2H, t, J 7.3 Hz), 1.71 (2H, hex, J 7.3 Hz), 1.29 (3H, t, J 7.1 Hz), 1.04 (3H, t, J 7.3 Hz); m/z ($EI^+$, 100V) 520.

EXAMPLE 6

S-Ethyl 3-[4-(3,5-dichloropyrid-4-ylcarboxamido)-phenyl]-2-(6-propylsulphonylpyrimidin-4-ylamino)propionate mCPBA (assumed 60% pure, 1.43 g, 4.96 mmol) was added to a solution of the compound of Example 5 (1.26 g, 2.36 mmol) in dry DCM (20 ml), and stirred at room temperature for 4 h. 10% aqueous sodium sulphite (20 ml) was added and stirred for 5 min. After diluting with DCM (130 ml) and shaking, the phases were separated. The organic phase was washed consecutively with saturated aqueous $NaHCO_3$ (3×ml), water (25 ml) and brine (10 ml), dried ($Na_2SO_4$) and evaporated in vacuo. Chromatography (silica; 2% MeOH/DCM) afforded the title compound as a pale yellow foam (640 mg, '50%): $\delta H$ ($CDCl_3$) 8.63 (1H, s), 8.50 (2H, s), 8.05 (1H, s), 7.47 (2H, d, J 8.6 Hz), 7.10 (2H, d, J 8.6 Hz), 6.22–6.13 (1H, br. m), 5.18–5.08 (1H, br. m), 4.24 (2H, q, J 7.4 Hz), 3.32–3.25 (2H, m), 3.17 (1H, d, J, 14.1, 6.2 Hz), 1.75 (2H, hex, J 7.4 Hz), 1.31 (3H, t, J 7.1 Hz), 1.03 (3H; t, J 7.4 Hz); m/z ($EI^+$, 100V) 566.

EXAMPLE 7

S-3-[4-(3,5-Dichlopryrid-4-ylcarboxamido)-phenyl]-2-(propylsulphinylpyrimidin-4-ylamino)propanoic acid The title compound (395 mg, 66%) was prepared from the compound of Example 6 (630 mg, 1.11 mmol) by hydrolysis in a similar manner to Example 2: $\delta H$ (DMSO ds) 10.85 (1H, s), 8.77 (2H, s), 8.56 (1H, s), 8.44 (1H, d, J 7. $\delta Hz$), 7.55 (2H, d, J 8.4 Hz), 7.26 (2H, d, J 8.4 Hz), 7.22 (1H, s), 4.85–4.72 (1H, br. m), 3.33 (2H, t, J 7.6 Hz), 3.18 (1H, d, J 13.8, 4.7 Hz), 2.99 (1H, d, J, 13.8, 9.1 Hz), 1.59 (2H, hex, J 7.6 Hz), 0.93 (3H, t, J 7.6 Hz); m/z ($EI^+$, 70V) 538.

EXAMPLE 8

S-Ethyl 3-[4-(3,5-dichloropyrid-4-ylcarboxamido)phenyl]-2-(6-propylsulphinylpyrimidin-4-ylamino)propionate mCPBA (assumed 86% pure, 223 mg, 1.11 mmol) was added to an ice-bath cooled solution of the compound of Example 5 (500 mg, 0.94 mmol) in dry DCM (15 ml), and stirred for 1 h with cooling and for 2 h at room temperature. 10% aqueous sodium sulphite (10 ml) and DCM (100 ml) was added and the mixture vigorously stirred for 5 min. The phases were separated and the organic phase was washed consecutively with saturated aqueous $NaHCO_3$ (2×30 ml), water (10 ml) and brine (10 ml), dried ($Na_2SO_4$) and evaporated in vacuo. Chromatography (silica; 2–3% MeOH/DCM) afforded the title compound as a mixture of diastereoisomers together with a small amount of the corresponding ethoxyethyl analogue (330 mg, 64%): $\delta H$ ($CDCl_3$) 8.82–8.80 (1H, s), 8.49–8.45 (3H, s), 7.53–7.47 (2H, overlapping d's, J 8.6 Hz), 7.17–7.08 (2H, overlapping d's J 8.6 Hz), 7.01–6.95 (1H, s), 6.31–6.22 (1H, m), 5.20 5.00 (1H, br. m), 4.30–4.15 (2H, overlapping q's, J 7 Hz), 3.87–3.12 (2H, br. m), 3.10–3.01 (1H, br. m), 2.87–2.70 (1H, br. m), 1.92–1.74 (1H, br. m), 1.69–1.50 (1H, br. m), 1.33–1.20 (3H, t, J 7 Hz), 1.08–0.99 (3H, overlapping t's, J 7 Hz); m/z ($EI^+$, 70V) 550.

EXAMPLE 9

S-3-[4-(35,-Dichloropyrid-4-ylcarboxamido)-phenyl]-2-(6-propylsulphinylpyrimidin-4-ylamino)propanoic acid The title compound as a 1:1 mixture of diastereoisomers (278 mg, 92%) was prepared from the compound of Example 8 (320 mg, 0.58 mmol) by hydrolysis in a similar manner to Example 2; $\delta H$ (DMSO $d_6$) 10.85 (1H, s), 8.77 (2H, s), 8.40 (1H, s), 8.25 (1H, d, J 7.6 Hz), 7.55 (2H, d, J 8.3 Hz), 7.30–7.20 (2H, m), 7.09 (1H, s), 4.82–4.69 (1H, m), 3.17 (1H, d, J 14, 4 Hz), 3.12–2.90 (2H, br. m), 2.85–2.72 (1H, m), 1.80–1.62 (1H, m), 1.55–1.37 (1H, m), 1.01–0.90 (3H, overlapping t's); m/z ($EI^{+'}$, 70V) 522.

EXAMPLE 10

S-Ethyl 3 [4-(3,5-dichloropyrid-4-ylcarboxamido)-phenyl]-2-16 benzylthiopyrimidin-4-ylamino)propionate A solution of Intermediate 3 (1.0 g, 2.39 mmol), DIPEA (647 mg, 872 µl, 5 mmol) and 4-benzylthio-6-chloro-pyrimidine (678 mg, 2.87 mmol) in 2-ethoxyethanol (4 ml) was heated at 120° for 5$\delta H$. The volatiles were removed in vacuo and the residue worked up in a manner analogous to that described for Example 5. The crude product was chromatographed (silica; 2–3% MeOH/DCM) to afford the title compound (together with some of the ethoxyethyl ester analogue) as a near colourless glassy solid (560 mg, 40%): $\delta H$ ($CDCl_3$) 8.55 (2H, s), 8.42 (1H, s), 7.73 (1H, s), 7.51 (2H, d, J 8.4 Hz), 7.39–7.24 (m, 5H), 7.11 (2H, d, J 8.4 Hz), 6.19 (1H, s), 5.27–5.18 (1H, m), 4.95–4.81 (1H, m), 4.37 (2H, s), 4.21 (2H, q, J 0.1 Hz), 3.21 (1H, d, J 14.0, 5.0 Hz), 3.15 (1H, d, J 14.0, 5.7 Hz), 1.28 (3H, t, J 7.1 Hz); m/z ($EI^+$, 70V) 582.

EXAMPLE 11

S-Ethyl 3-[4-(3,5-Dichloropyrid-4-ylcarboxamido)phenyl]-2-(6-benzylthiolpyrimidin-4-ylamino)propanoic acid The title compound was prepared from the compound of Example 10 by hydrolysis in a similar manner to Example 2: $\delta H$ (DMSO $d_6$, 390K) 10.84 (1H, br. s), 8.77 (2H, s), 8.24 (1H, s), 7.55–7.25 (7H, m), 6.46 (1H, s), 4.66 (1H, m), 4.31 (2H, s), 3.13–2.90 (2H, m); m/z ($EI^+$, 70V) 554.

EXAMPLE 12

S-Ethyl 3-[3-Chloro-4-(3,5-dichloropyrid-4-ylcarboxamido)-phenyl]-2-(6-diethylaminosulphonylpyrimidin-4-ylamino)pronionate and S-Ethyl 3-[3-5-dichloro-4-(3,5-dichloropyrid-4-ylcarboxamido)phenyl]-2-(6-diethylaminosulphonylpyrimidin-4-ylamino)propionate Chlorine gas was bubbled through a vigorously stirred ice-bath cooled mixture of the compound of Example 10 (550 mg), DCM (8 ml) and 10% aqueous HCl (20 ml). The cooled reaction mixture was then stirred for an additional 30 min. Excess chlorine was removed by purging with nitrogen and the reaction mixture diluted with DCM (70 ml). The phases were shaken, separated and the aqueous phase re-extracted with DCM (30 ml). The combined organic extracts were treated with diethylamine (2 ml) and left to stand for 45 min. The volatiles were removed in vacuo and the residue partitioned between EtOAc (70 ml) and water (20 ml). The phases were separated and the aqueous phase re-extracted with EtOAc (2×15 ml). The combined organic extracts were washed with brine (10 ml), dried (MgSO$_4$) and evaporated in vacuo. The obtained dark foam was chromatographed twice (silica; 2% MeOH/DCM then 25%Et$_2$O/DCM) affording a 2:1 mixture of the title compounds (240 mg): δH (CDCl$_3$) 8.62 (1H, s), 8.59 (2H×0.66, s), 8.57 (2H×0.33, s), 8.31 (1H×0.66, s), 7.85 (1H×0.33, s), 7.20 (2H×0.33, s), 7.11 (1H×0.66, d, J 8.4 Hz), 5.84–5.72 (1H, br. m), 5.18–4.95 (1H, br. m), 4.26 (2H, q, 7.1 Hz), 3.39 (2H, q, J 7.1 Hz), 3.28 (1H, d, J. 14.0, 5.3 Hz), 3.17 (1H, d, J 14.0, 5.6 Hz), 1.32 (3H×0.33, t, J 7.1 Hz), 1.30 (3H×0.66, t, J 7.1 Hz), 1.17 (6H, t, J 7.1 Hz); m/z (EI$^+$, 70V) 531 and 665.

EXAMPLE 13

S-3-[3-Chloro-4(3,5-dichloropyrid-4-ylcarboxamido)-phenyl]-2-(6-diethylaminosulphonylpyrimidin-4-ylamino)propanoic acid and S-3[3,5-dichloro-4-(3,5-dichloropyrid-4-ylcarboxamido)-phenyl]-2-(6-diethylaminosulphonylpyrimidin-4-ylamino) propanoic acid The mixture of compound of Example 12 (240 mg, 0.38 mmol) was treated with a solution of LiOH.2H$_2$O (27 mg, 0.64 mmol) in dioxan (3 ml) and water (3 ml) at room temperature for 2.5 h. A few crops of acetic acid were added and the volatiles were removed in vacuo. The residue was chromatographed several times (silica; DCM (400–200), MeOH (20), AcOH (3), H$_2$O (2)) to separate the two title compound affording after freeze-drying from aqueous methanol, the less polar S-3-[3-Chloro-4-(3,5-dichloropyrid-4-ylcarboxamido)-phenyl]-2-(6-diethylaminosulphonylpyrimidin-4-ylaminolpropanoic acid as a white amorphous solid (105 mg, 49%): δH (DMSO d$_6$) 10.61 (1H, s), 8.75 (2H, s), 8.50 (1H, s), 8.31 (1H, d, J 7. δHz), 7.62 (1H, d, J 8.1 Hz), 7.43 (1H, s), 7.28 (1H, d, J. 8.1 Hz), 7.10 (1H, s), 4.83–4.75 (1H, m), 3.26 (4H, t, J 7.1 Hz), 3.22 (1H, m), 3.05 (1H, dd, J, 13.8, 9.1 Hz), 1.05 (6H, t, J 7.1 Hz); m/z (ES$^+$, 70V) 603; and the more polar S-3-[3,5-dichloro-4-(,3,5-dichloropyrid-4-ylcarboxamido)-phenyl]-2-(6-diethylaminosulphonylpyrimidin-4-ylamino), propanoic acid as a white amorphous solid (49 mg, 21%): δH (DMSO d$_6$) 10.83 (1H, s), 8.76 (2H, s), 8.50 (1H, s), 8.29 (1H, d, J 7. δHz), 7.44 (2H, s), 7.12 (1H, s), 4.85–4.74 (1H, m), 3.26 (4H, t, J 7.1 Hz), 3.20 (1H, m), 3.05 (1H, dd, J 13.8, 9.9 Hz), 1.05 (6H, t, J 7.1 Hz); m/z (EI$^+$, 70V) 637.

EXAMPLE 14

S-Ethyl 3-[3-Chloro-4-(3,5-dichloropyrid-4-ylcarboxamido)-phenyl]-2-(6-propylaminosulphonylpyrimidin-4-ylamino)propionate The title compound (430 mg) was prepared in an analogous manner to the compound of Example 12 starting from the compound of Example 10 (500 mg) and using n-propylamine: δH (CDCl$_3$) 8.63 (1H, s), 8.60 (2H, s), 8.45 (1H, s), 8.32 (1H, d, J 7. δHz), 7.88 (1H, s), 7.25–6.98 (3H, m), 6.02–5.90 (1H, m), 5.13–5.06 (1H, m), 4.28 (2H, q, J 17 Hz), 3.38–3.15 (2H, m), 3.04 (2H, q, J 7.1 Hz), 1.53 (2H, q, J 7.1 Hz), 1.24 (3H, t, J 7.1 Hz), 0.97 (3H, t, 7.1 Hz); m/z (EI$^+$, 70V) 627.

EXAMPLE 15

S-3-[3-Chloro-4-(3,5-dichloropyrid-4-ylcarboxamido)-phenyl]-2-6-propylaminosulphonylpyrimidin-4-ylamino)propanoic acid The title compound (151 mg, 66%) was prepared from the compound of Example 14 (394 mg, 0.60 mmol) by hydrolysis in a similar manner to Example 2: δH (DMSO d$_6$) 10.61 (1H, s), 8.76 (2H, s), 8.51 (1H, s), 8.32 (1H, d, J 7. δHz), 7.80 (1H, t, J 5.7 Hz), 7.63 (1H, d, J 8.3 Hz), 7.45 (1H, s), 7.29 (1H, d, J 8.3 Hz), 7.10 (1H, s), 4.85–4.74 (1H, m), 3.22 (1H, d, J 13.9, 4.9 Hz), 3.02 (1H, dd, J 13.9, 9.0 Hz), 2.86 (2H, t, J 6.8 Hz), 1.38 (2H, hex, J 6. δHz), 0.79 (3H, t, J 7.3 Hz); m/z (EI$^+$, 70V) 589.

EXAMPLE 16

S-3-[4-(3,5-Dichloropyrid-4-ylcarboxamido)-phenyl]-2-(6-methoxy-2-methylsulphonylpyrimidin-4-ylamino)propanoic acid The title compound was prepared from Intermediate 3 and 2,4-di-(methylsulphonyl)-6-methoxypyrimidine by a method similar to that described for Intermediate 10 followed by ester hydrolysis according to the method of Example 2: δH (DMSO d$_6$) 12.70 (1H, br. s), 10.84 (1H, s), 8.77 (2H, s), 8.23 (d, J 7.6 Hz) and 8.08 (d, J 7.7 Hz) together (1H), 7.54 (2H, d, J 8.0 Hz), 7.33 (2H, d, J 8.0 Hz), 6.48 (1H, s), 4.55–4.46 (1H, m), 3.89 (s) and 3.86 (s) together (3H), 3.20–3.03 (2H, m); m/z (EI$^+$, 70V) 540.

EXAMPLE 17

S-3-[4-(3,5-Dichloropyrid-4-ylcarboxamido)-phenyl]-2-(6-methoxy-2 propylsulphonylpyrimidin-4-ylamino)propanoic acid The title compound was prepared from Intermediate 3 and 2,4-di-n-propylsulphonyl-6-methoxypyrimidine by a method similar to that described for Intermediate 10 followed by ester hydrolysis according to the method of Example 2: δH (DMSO d$_6$) 12.69 (1H, br.s), 10.83 (1H, s), 8.77 (2H, s), 8.18 (d, J 7.9 Hz) and 8.06 (d, J 7.9 Hz) together (1H), 7.54 (2H, d, J 8.2 Hz), 7.32 (2H, d, J. 8.2 Hz), 6.48 (s) and 6.47 (s) together (1H), 4.55–4.42 (1H, m), 3.89 (s) and 3.86 (s) together (3H), 3.29 (2H, q, J 7.7 Hz), 3.12 (1H, d, J 13.9, 4.6 Hz), 3.02 (1H, d, J 13.9, 9.9 Hz), 1.68–1.49 (2H, m), 0.94 (t, J 7.2 Hz) and 0.92 (t, J 7.2 Hz) together (3H); m/z (EI$^+$, 70V) 568 and 570.

EXAMPLE 18

S-3-[4-(3,5-Dichloropyrid-4-ylcarboxamido)-phenyl]-2-(4-trifluoromethylpyrimidin-2-ylamino)propanoic acid The title compound was prepared from Intermediate 3 and 2-chloro-4 (trifluoromethyl) pyrimidine, followed by hydrolysis: δH (DMSO d$_6$) 12.70 (1H, br.s), 10.83 (1H, s), 8.77 (2H, s), 8.58 (1H, d, J 4.9 Hz), 8.15 (d, J 8.0 Hz) and 8.06 (d, J 8.0 Hz) together (1H), 7.54 (2H, d, J 8.2 Hz), 7.33 (2H, d, J 8.2 Hz), 6.99 (1H, d, J 4.9 Hz), 4.62–4.42 (1H, br. m), 3.15 (1H, dd, J 13.7, 4.4 Hz), 3.10–2.95 (1H, m); m/z (EI$^+$, 60V) 500 and 502.

EXAMPLE 19

S-3-[4-(3,5-Dichloropyrid-4-ylcarboxamido)-phenyl]-2-(6-phenoxypyrimidin-4-ylamino)propanoic acid The title compound was prepared from Intermediate 3 and 4-chloro-6-phenoxypyrimidine, followed by hydrolysis: δH (DMSO $d_6$) 10.85 (1H, s), 8.77 (2H, s), 8.12 (1H, s), 7.60 (1H, br. d, J 8.0 Hz), 7.54 (2H, d, J 8.3 Hz), 7.41 (2H, t, J 7. δHz), 7.27–7.20 (3H, m), 7.12 (2H, d, J 8.2 Hz), 5.88 (1H, s), 4.80–4.60 (1H, br. m), 3.12 (1H, did, J 13.8, 4.7 Hz), 2.90 (1H, d, J 13.8, 9.5 Hz); m/z (EI$^+$, 60V) 524 and 526.

EXAMPLE 20

S-3-[4-(3,5-Dichloropyrid-4-ylcarboxamidol-phenyl]-2-(2-methylthiopyrimidin-4-ylamino)propanoic acid The title compound was prepared from Intermediate 3 and 4-chloro-2-methylthiopyrimidine followed by hydrolysis: δH (DMSO $d_6$) 10.83 (1H, s), 8.77 (2H, s), 7.85 (1H, d, J 5.7 Hz), 7.71 (1H, br. s), 7.54 (1H, d, J 8.5 Hz), 7.25 (1H, d, J 8.5 Hz), 6.28 (1H, d, J 5.7 Hz), 4.70–4.53 (1H, br. m), 3.12 (1H, d, J 14.0 8.0 Hz), 2.96 (1H, d, J 14.0, 8.0 Hz); m/z (EI$^+$, 60V) 478.

EXAMPLE 21

S-3-[4(3,5-Dichloropyrid-4-ylcarboxamido)phenyl]-2-95-carboxy-2-methylthiolpyrimidin-4-ylamino) propanoic acid The title compound was prepared from Intermediate 3 and ethyl 4-chloro-2-methylthiopyrimidine-5-carboxylate, followed by hydrolysis: δH (DMSO $d_6$) 10.87 (1H, s), 9.01 (1H br. s), 8.77 (2H, s), 8.49 (1H, s), 7.55 (2H, d, J 8.4 Hz), 7.20 (2H, d, J 8.4 Hz), 4.90–4.80 (1H, m), 3.21 (1H, d, J 13.8, 5.2 Hz), 3.09 (1H, d, J 13.8, 6.9 Hz), 2.44 (3H, s); m/z (EI$^+$, 60V) 522.

EXAMPLE 22

S-3-[4-(3,5-Dichloropyrid-4-ylcarboxamido)-phenyl]-2-(5-ethoxycarboxy-2-methylthiopyrimidin-4-ylamino)propanoic acid The title compound was prepared from Intermediate 3 and ethyl 4-chloro-2-methylthiopyrimidine-5-carboxylate with subsequent partial hydrolysis of the coupled product: δH (DMSO $d_6$) 10.84 (1H, br. s), 8.77 (2H, s), 8.55 (1H, s), 8.47 (1H, d, J 6. δHz), 7.54 (2H, d, J 8.3 Hz), 7.18 (2H, d, J 8.3 Hz), 4.94–4.83 (1H, m), 4.25 (2H, q, J 7.1 Hz), 3.25 (1H, d, J 13.8, 5.3 Hz), 3.13 (1H, d, J 13.8, 6. δHz), 2.46 (3H, s), 1.26 (3H, t, J 7.1 Hz); m/z (EI$^+$, 60V) 550.

EXAMPLE 23

S-3-[4-(3,5-Dichloropyrid-4-ylcarboxamido)-phenyl]-2-(3-nitropyrid-2-ylamino)propanoic acid The title compound was prepared from Intermediate 3 and 2-chloro-3-nitropyridine, followed by hydrolysis: δH (DMSO $d_6$) 10.86 (1H, s), 8.77 (2H, s), 8.49–8.43 (2H, m), 8.29 (1H, d, J 7.0 Hz), 7.55 (2H, d, J 8.5 Hz), 7.22 (2H, d, J 8.5 Hz), 6.84 (1H, dd, J 8.3, 4.5 Hz), 5.03–4.99 (1H, m), 3.30–3.15 (2H, m); m/z (EI$^+$, 60V) 476 and 478.

EXAMPLE 24

S-3-[4-(3,5-Dichloropyrid-4-ylcarboxamido)-phenyl]-2-(5-nitropyrid-2-ylamino)propanoic acid The title compound was prepared from Intermediate 3 and 2-chloro-5-nitropyridine, followed by hydrolysis: δH (DMSO $d_6$) 10.84 (1H, s), 8.85 (1H, d, J 2.6 Hz), 8.76 (2H, s), 8.32 (1H, d, J 7.4 Hz), 8.10 (1H, d, J, 9.4, 2.6 Hz), 7.54 (2H, d, J 8.3 Hz), 7.26 (2H, d, J 8.3 Hz), 6.69 (1H, d, J 9.4 Hz), 4.81 (1H, br. m), 3.19 (1H, dd, J, 13.9, 4.7 Hz), 3.00 (1H, dd, J 13.9, 9.2 Hz); m/z (EI$^+$, 60V) 476 and 478.

EXAMPLE 25

S-3-[4-(3,5-Dichloropyrid-4-ylcarboxamido)-phenyl]-2-(6-propylthiopyrimidin-4-ylamino)propanoic acid The title compound was prepared by hydrolysis of the compound of Example 5: δH (DMSO $d_6$) 10.83 (1H, br. s), 8.77 (2H, s), 8.21 (1H, s), 7.54 (2H, d, J 8.4 Hz), 7.24 (2H, d, J 8.4 Hz), 6.43 (1H, br. s), 4.67 (1H, br. s), 3.13 (1H, dd, J 13.9, 4. δHz)), 3.00–2.90 (3H, m), 1.61 (2H, hex, J 7.3 Hz), 0.95 (3H, t, J 7.3 Hz); m/z (EI$^+$, 160V) 506 and 508.

EXAMPLE 26

S-3-[4-(3,5-Dichloropyrid-4-ylcarboxamido)-phenyl]-2-(2-nitrophenylamino)propanoic acid The title compound was prepared from Intermediate 3 and 2-fluoronitrobenzene, followed by hydrolysis: δH (DMSO $d_6$) 10.86 (1H, br. s), 8.76 (2H, s), 8.20 (1H, d, J 7.7 Hz), 8.08 (1H, dd, J. 8.6, 1.6 Hz), 7.56 (2H, d, J 8.5 Hz), 7.53 (1H, m), 7.16 (2H, d, J 8.5 Hz), 7.04 (1H, d, J 8.2 Hz), 6.74 (1H, t, J 7.5 Hz), 4.79–4.73 (1H, m), 3.26–3.13 (2H, m); m/z (EI$^+$, 60V) 476 and 478.

EXAMPLE 27

S-3-[4-(3,5-Dichloropyrid-4-ylcarboxamido)-phenyl]-2-(pyrimidin-2-ylamino)propanoic acid The title compound was prepared from Intermediate 3 and 2-chloropyrimidine, followed by hydrolysis: δH (DMSO $d_6$) 10.82 (1H, br. s), 8.76 (2H, s), 8.23 (2H, d, J 4.7 Hz), 7.52 (2H, d, J 8.3 Hz), 7.27 (2H, d, J 8.3 Hz), 7.12 (1H, d, J 7.5 Hz), 6.57 (1H, t, J 4.7 Hz), 4.50–4.40 (1H, m), 3.12 (1H, d, J 13.8, 4.5 Hz), 3.00 (1H, dd, J 13.8, 9.1 Hz); m/z (EI$^+$, 60V) 432 and 434.

EXAMPLE 28

S-3-[4-(3,5-Dichloropyrid-4-ylcarboxamido)-phenyl]-2-(6-methylsulphonylpyrimidin-4-ylamino) propanoic acid The title compound was prepared from Intermediate 3 and 2,4-di-(methylsulphonyl)-pyrimidine, followed by hydrolysis: δH (DMSO $d_6$) 8.79 (2H, s), 8.58 (1H, s), 8.47 (1H, d, J 7. δHz), 7.57 (2H, d, J 8.5 Hz), 7.28 (2H, d, J 8.5 Hz), 7.21 (1H, s), 4.79 (1H, m), 3.20 (3H, s), 3.19 (1H, m), 3.00 (1H, dd, J, 13.9, 9.2 Hz); m/z (EI$^+$, 70V) 510.

EXAMPLE 29

S-3-[4-(3,5-Dichloropyrid-4-ylcarboxamido)-phenyl]-2-(2-propylsulphonylpyrimidin-4-ylamino)propanoic acid The title compound was prepared from Intermediate 3 and Intermediate 13, followed by hydrolysis: δH (DMSO $d_6$) 8.60 (2H, s), 8.10 (1H, d, J 6.0 Hz), 7.50 (2H, d, J 8.5 Hz), 7.28 (2H, d, J 8.5 Hz), 6.70 (1H, d, J 6.0 Hz), 4.90 (1H, m), 3.30 (4H, m), 3.10 (1H, m), 1.20 (2H, m), 1.00 (3H, t, J 7.1 Hz); m/z (EI', 70V) 538.

EXAMPLE 30

S-Ethyl 3-[4-(3,5-dichloropyrid-4-ylcarboxamido)-phenyl]-2-(4-methoxy-6-dimethylamino-1,3,5-triazin-2-ylamino)propanionate To a solution of Intermediate 10 (0.26 g, 0.50 mmol) in dry THF (5 ml) under nitrogen was added dimethylamine (941 mg, 0.5 mmol) and DIPEA (0.17 ml). The solution was stirred at room temperature for 4.5 h then the solvent was removed in vacuo and DCM (10 ml) was added. The organic layer was washed with aqueous sodium bicarbonate and water, dried (MgSO$_4$) and the solvent removed in vacuo. Flash chromatography (silica; EtOAc/Hexane 1:1) gave the title compound as a froth (0.16 g, 59%): δH (CDCl$_3$) 8.55 (2H, s), 7.75 (1H, br. s), 7.54 (2H, d, J 8.4 Hz), 7.18 (2H, d, J 8.4 Hz), 5.40 (1H, m), 4.90 (1H, m), 4.17 (2H, d, J 7.2 Hz), 3.84 (3H, s), 3.28–3.10 (2H, m), 3.11 (6H, s), 1.16 (3H, t, J 7.2 Hz); m/z (EI$^+$, 70V) 534.

EXAMPLE 31

S-3-[4-(3,5-Dichlorolpyrid-4-ylcarboxamido)-phenyl]-2-(4-methoxy-6-dimethylamino-1,3,5-triazin-2-ylamino)propanoic acid The title compound was prepared from the compound of Example 30 by hydrolysis in a similar manner to Example 2: δH (DMSO $d_6$) 10.83 (1H, s), 8.77 (2H, s), 7.53 (2H, d, J 8.0 Hz), 7.38 (1H, m), 7.28 (2H, d, J 7.9 Hz), 4.72 (1H, m), 3.72 (3H, d, J, 4.2 Hz), 3.00 (δH, d, J 4.5 Hz); m/z (EI", 60V) 506.

In a similar manner were prepared the following compound of Examples 32–49:

EXAMPLE 32

S-3-[4-(3,5-Dichloropyrid-4-ylcarboxamido)-phenyl]-2-(4-methoxy-6 diethylamino-1,3,5-triazin-2-ylamino)propanoic acid Prepared from Intermediate 10 and diethylamine, followed by hydrolysis: δH (DMSO $d_6$, 390K) 10.39 (1H, br. s), 8.65 (2H, s), 7.50 (2H, d, J 8.3 Hz), 7.25 (2H, d, J 8.3 Hz), 6.41 (1H, br. m), 4.55 (1H, br. m), 3.54 (4H, dd, J 6.9 Hz), 3.39 (3H, s), 3.20–3.00 (2H, m), 1.11 (6H, t, J 6.9 Hz); m/z (EI$^+$, 60V) 534.

EXAMPLE 33

S-3-[4-(3,5-Dichloropyrid-4-ylcarboxamido)-phenyl]-2-(4-methoxy-6 morpholino-1,3,5-triazin-2-ylamino)propanoic acid Prepared from Intermediate 10 and morpholine, followed by hydrolysis: δH (DMSO $d_6$, 365K) 10.49 (1H, br. s), 8.69 (2H, s), 7.53 (2H, d, J 8.1 Hz), 7.25 (2H, d, 1 8.4 Hz), 6.87 (1H, br. s), 4.62 (1H, m), 3.78 (3H, s), 3.70–3.55 (δH, m), 3.20–3.00 (2H, m); m/z (EI$^+$, 70V) 548.

EXAMPLE 34

S-3-[4-(3,5-Dichloropyrid-4-ylcarboxamido)-phenyl]-2-(4-methoxy-6 propyloxy-1,3,5-triazin-2-ylamino)propanoic acid Prepared from Intermediate 10 and sodium n-propoxide, followed by hydrolysis: δH (DMSO $d_6$, 390K) 8.69 (2H, s), 7.53 (2H, d, J 8.4 Hz), 7.50 (1H, br. m), 7.27 (2H, d, J 8.3 Hz), 4.66 (1H, m), 4.20 (2H, t, J 6.6 Hz), 3.82 (3H, s), 3.25–3.00 (2H, m), 1.68 (2H, m, J 6. δHz), 0.93 (3H, t, J 7.4 Hz); m/z (EI$^+$, 60V) 521.

EXAMPLE 35

S-3-[4-(3,5-Dichloropyrid-4-ylcarboxamido)-phenyl]-2-(4-methoxy-6 phenoxy-1,3,5-triazin-2,-ylamino)propanoic acid Prepared from Intermediate 10 and sodium phenoxide, followed by hydrolysis: δH (DMSO $d_6$) 10.84 (1H, s), 8.77 (2H, s), 8.25 (1H, m), 7.53 (2H, d, J 8.4 Hz), 7.40–7.10 (7H, m), 4.52 (1H, m), 4.41 (1H, m), 3.76 (3H, s), 3.10–2.80 (2H, m); m/z (EI$^+$, 60V) 555.

EXAMPLE 36

S-3-[4-(3,5-Dichloropyrid-4-ylcarboxamido)-phenyl]2-(4-methoxy-6 propylamino-1,3,5-triazin-2-ylamino)propanoic acid Prepared from Intermediate 10 and n-propylamine, followed by hydrolysis: δH (DMSO $d_6$, 390K) 10.38 (1H, br. s), 8.67 (2H, s), 7.51 (2H, d, J 8.4 Hz), 7.25 (2H, d, J 8.4 Hz), 6.60 (1H, m), 6.44 (1H, m), 4.68 (1H, m), 3.77 (3H, s), 3.25–3.00 (4H, m), 1.53 (2H, q, J 14.3, 7.2 Hz), 0.88 (3H, t, J 7.4 Hz); m/z (EI$^+$, 60V) 520.

EXAMPLE 37

S-3-[4-(3,5-Dichloropyrid-4-ylcarboxamido)-phenyl]-2-[4-methoxy-6-(2-hydroxyethylamino)-1,3,5-triazin-2-ylamino]propanoic acid Prepared from Intermediate 10 and 2-hydroxyethylamine, followed by hydrolysis: δH (DMSO $d_6$, 350K) 10.57 (1H, s), 8.72 (2H, s), 7.54 (2H, d, J 8.2 Hz), 7.27 (2H, d, J 8.3 Hz), 6.78–6.68 (1H, m), 4.62 (1H, m), 3.77 (3H, s), 3.50 (2H, d, J 6.0 Hz), 3.35 (2H, d, J 5.65 Hz), 3.17–3.02 (2H, m); m/z (EI$^+$, 60V) 522.

EXAMPLE 38

S-3-[4-(3,5-Dichloropyrid-4-ylcarboxamido)-phenyl]-2-[4-methoxy-6-(4-carboxylpiperidinyl)-1,3,5-triazin-2-ylamino)propanoic acid Prepared from Intermediate 10 and ethyl piperidine-4-carboxylate, followed by hydrolysis: δH (DMSO d$_6$, 390K) 10.83 (1H, s), 8.76 (1H, s), 7.53 (2H, d, J 8.3 Hz), 7.45 (1H, m), 7.27 (2H, d, J 8.4 Hz), 4.55–4.30 (2H, m), 3.72 (3H, s), 3.10–2.80 (2H, m), 1.90–1.75 (2H, m), 1.50–1.30 (2H, m); m/z (EI$^+$, 70V) 590.

EXAMPLE 39

S-3-[4-(3,5-Dichloropyrid-4-ylcarboxamido)-phenyl]-2-[4-methoxy-6-piperazinyl-1,3,5-triazin-2-ylamino)propanoic acid Prepared from intermediate 10 and N-BOC piperazine, followed by hydrolysis and BOC deprotection: δH (DMSO d$_6$) 10.58 (1H, s), 8.72 (3H, s), 7.53 (2H, d, J 8.5 Hz), 7.24 (2H, d, J 8.5 Hz), 6.86 (1H, m), 4.56 (1H, m), 3.78 (3H, s), 3.64 (4H, t, J 5.0 Hz), 3.17–3.00 (2H, m), 2.75 (4H, t, J 5.0 Hz); m/z (EI$^+$, 60V) 547.

EXAMPLE 40

S-3-[4-(3,5-Dichloropyrid-4-ylcarboxamido)-phenyl]-2-(4-methoxy-6-(N'-t-butyloxycarbonylpiperazinyl)-1,3,5-triazin-2-ylamino)propanoic acid Prepared from Intermediate 10 and N-BOC piperazine, followed by hydrolysis: δH (DMSO d$_6$, 390K) 10.34 (1H, s), 8.67 (2H, s), 7.53 (2H, d, J 7.0 Hz), 7.52 (1H, m), 7.27 (2H, d, J 8.4 Hz), 6.65 (1H, d, J 7.6 Hz), 4.70 (1H, m), 3.81 (3H, s), 3.70 (4H, m), 3.40 (4H, m), 3.30–3.10 (2H, m), 1.46 (9H, s); m/z (EI$^+$, 70V) 647.

EXAMPLE 41

S-3-[4-(3,5-Dichloropyrid-4-ylcarboxamido)-phenyl]-2-(6-methyl-2-propylsulphonylpyrimidin-4-ylamino)propanoic acid Prepared from Intermediate 3 and 6-methyl-2,4-di-(n-propylsulphonyl)-pyrimidine, followed by hydrolysis: δH (DMSO d$_6$) 10.83 (1H, s), 8.77 (2H, s), 8.27 (1H, d, J 8.0 Hz), 7.54 (2H, d, J 8.3 Hz), 7.25 (2H, d, J 8.2 Hz), 6.58 (1H, s), 4.66 (1H, m), 3.44–2.90 (4H, m), 2.28 (3H, s), 1.67–1.59 (2H, m), 0.96 (3H, t, J 7.4 Hz); m/z (EI$^+$, 70V) 552.

EXAMPLE 42

S-3-[4-(3,5-Dichloropyrid-4 ylcarboxamido)-phenyl]-2-(6-benzylsulphonylpyrimidin-4-ylamino)propanoic acid Prepared from Intermediate 3 and 4,6-di-(benzylsulphonyl)pyrimidine, followed by hydrolysis: δH (DMSO d$_6$) 10.85 (1H, s), 8.77 (2H, s), 8.62 (1H, s), 8.35 (1H, d, J 7.4 Hz), 7.54 (2H, d, J 8.3 Hz), 7.30–7.19 (7H, m), 7.02 (1H, s), 4.71 (1H, m), 3.29–2.97 (2H, m), 1.89 (2H, s); m/z (EI$^+$, 70V) 586.

EXAMPLE 43

S-3-[4-(3,5-Dichlorolpyrid-4-ylcarboxamido)-phenyl]-2-(6-carboxy-2-propylsulphonylpyrimidin-4-ylamino)propanoic acid Prepared from Intermediate 3 and methyl 2,6-di-(n-propylsulphonyl) pyrimidine-4-carboxylate, followed by hydrolysis: δH (DMSO d$_6$) 10.85 (1H, s), 8.76 (1H, s), 8.76 (2H, s), 7.56 (2H, d, J 8.5 Hz), 7.35 (1H, s), 7.26 (2H, d, J 8.5 Hz), 4.74 (1H, m), 3.74–2.98 (4H, m), 1.70–1.62 (2H, J 7.5 Hz), 0.97 (3H, t, J 7.4 Hz); m/z (EI$^+$, 70V) 582.

EXAMPLE 44

S-3-[4-(3,5-Dichlorolpyrid-4-ylcarboxamido)-phenyl]-2-(6-methyl-4-(propylaminocarbonyl)-pyrimidin-2-ylamino)propanoic acid Prepared from Intermediate 3 and 2-chloro-4-methyl-6-(n-propylamino-carbonyl) pyrimidine, followed by hydrolysis: δH (DMSO d$_6$) 10.82 (1H, s), 8.76 (2H, s), 8.32 (1H, br. s), 7.53 (2H, d, J 8.5 Hz), 7.31 (2H, d, J 8.2 Hz), 7.00 (1H, s), 4.75 (1H, m), 3.30–3.10 (4H, m), 2.30 (3H, s), 1.54–1.47 (2H, 5 q, J 14,6, 7.4 Hz), 0.87 (3H, t, J 7.3 Hz); m/z (EI$^+$, 70V) 531.

EXAMPLE 45

S-3-[4-(3,5-Dichlorolpyrid-4-ylcarboxamido)-phenyl]-2-(6-methyl-4-(diethylaminocarbonyl)-pyrimidin-2-ylaminolpropanoic acid Prepared from Intermediate 3 and 2-chloro-4-methyl-6-(diethylamino-carbonyl) pyrimidine, followed by hydrolysis: δH (DMSO d$_6$) 10.34 (1H, s), 8.67 (1H, s), 7.51 (2H, d, J 6.3 Hz), 7.27 (2H, d J 8.3 Hz), 6.54 (1H and 1H, together 2H, s), 7.51 (2H, d, J 6.3 Hz), 7.27 (2H, d J 8.3 Hz), 6.54 (1H and 1H, together 2H, s), 4.75 (1H, m), 3.35 (4H, m), 3.23–3.07 (2H, m), 2.30 (3H, s), 1.13 (6H, m); m/z (EI$^+$, 70V) 545.

EXAMPLE 46

S-3-[4-(3,5-Dichloropyrid-4-ylcarboxamido)-phenyl]-2-(6-carboxy-2-iso-butylsulphonylpyrimidin-4-ylamino)propanoic acid Prepared from Intermediate 3 and methyl 2,6-di-(iso-butylsulphonyl) pyrimidine-4-carboxylate, followed by hydrolysis: δH (DMSO d$_6$) 10.84 (1H, s), 8.76 (2H, s), 7.55 (2H, d, J 8.5 Hz), 7.35 (1H, s), 7.26 (2H, d, J 8.5 Hz), 4.75 (1H, m), 3.39–3.02 (4H, m), 2.14–2.07 (1H, m), 0.98 (6H, d, J 3.3 Hz); m/z (EI$^+$, 70V) 596.

EXAMPLE 47

S-3-[4-(3,5-Dichloropyrid-4-ylcarboxamido)-phenyl]-2-(6-carboxy-2-hexylsulphonylpyrimidin-4-ylamino)propanoic acid Prepared from Intermediate 3 and methyl 2,6-di-(n-hexylsulphonyl) pyrimidine-4-carboxylate, followed by hydrolysis: δH (DMSO d$_6$) 10.84 (1H, 30 s), 8.78 (2H, s), 7.54 (2H, d, J 8.4 Hz), 7.36 (1H, s), 7.25 (2H, d, J 8.5 Hz), 4.77–4.71 (1H, m), 3.40–3.00 (4H, m), 1.65 (2H, m), 1.36 (2H, m), 1.24 (2H, t, J 3.3 Hz), 0.82 (3H, t, J 6.9 Hz); m/z (EI$^+$, 70V) 624.

EXAMPLE 48

S-3-[4-(3,5-Dichloropyrid-4-ylmethyloxy)-phenyl]-2-(4,6-dimethoxy-1,3,5-triazin-2-ylamino)propanoic acid The title compound was prepared from Intermediate 7 and 2-chloro-4,6-dimethoxy-1,3,5-triazine, followed by hydrolysis: $\delta$H (DMSO $d_6$) 8.70 (2H, s), 8.10 (1H, d, J 8.0 Hz), 7.24 (2H, d, J 8.3 Hz), 6.95 (2H, d, J 8.3 Hz), 5.18 (2H, s), 4.52 (1H, m), 3.81 (3H, s), 3.80(3H, s), 3.15–2.90 (2H, m); m/z (EI$^+$, 60V) 480.

EXAMPLE 49

S-3-[4-(3,5-Dichlorolpyrid-4-ylcarboxamido)-phenyl]-2-(4,6-propyloxy-1,3,5-triazin-2-ylamino)-propanoic acid Prepared from Intermediate 3 and 2-chloro-4,6-di-n-propoxy-1,3,5-triazine, followed by hydrolysis: $\delta$H (DMSO $d_6$) 10.84 (1H, br. s), 8.77 (2H, s), 8.00 (1H, d, J 7. $\delta$Hz), 7.54 (2H, d, J 8.4 Hz), 7.30 (2H, d, J 8.4 Hz), 4.52 (1H, m), 3.15–2.80 (2H, m), 1.64 (4H, m), 0.89 (6H, m); m/z (EI$^+$, 60V) 549.

EXAMPLE 50

S-Methyl 3-[4-(3,5-dichloropyrid-4-ylcarboxamido)-phenyl]-2-(N-methyl-4,6-dimethoxy-1,3,5-triazin-2-ylamino)propionate The title compound (350 mg, 80%) was prepared in an analogous manner to the compound of Example 1 starting from S-Methyl 3-[4-(3,5-dichloropyrid-4-ylcarboxamido)-phenyl]-2-(N-methylamino)propionate hydrochloride (500 mg 1.19 mmol): $\delta$H (CDCl$_3$) 8.55 (2H, s), 7.80 (1H, s), 7.50 (2H, d, J 8.0 Hz), 7.20 (2H, d, J 8.0 Hz), 5.40 (1H, m), 4.00 (3H, s), 3.95 (3H, s), 3.75 (3H, s), 3.50 (2H, m), 3.10 (3H, s); m/z (EI$^+$, 70V) 521.

EXAMPLE 51

S-3-[4-(3,5-Dichloropyrid-4-ylcarboxamido)-phenyl]-2-(N-methyl-4,6-dimethoxy-1,3,5-triazin-2-ylamino)propanoic acid The title compound was prepared from the compound of Example 50 by the method of Example 2: $\delta$H (DMSO $d_6$) 10.81 (s, 1H), 8.77 (2H, s), 7.51 (2H, d, J 8.5 Hz), 7.23 (2H, d, J 8.5 Hz), 5.34 (1H, m), 3.81 (3H, s), 3.80 (3H, s), 3.22 (2H, m), 2.92 (3H, s); m/z (EI$^+$, 70V) 507.

EXAMPLE 52

R-3-[4-(3,5-Dichloropyrid-4-ylcarboxamido)-phenyl]-2-(4,6-dimethoxy-1,3,5-triazin-2-ylamino)propanoic acid The title compound was prepared from R-ethyl-3-[4-(3,5-dichloropyrid-4-ylcarboxamido)phenyl-2-aminopropionate hydrochloride in an analogous fashion to the compounds of Examples 1 and 2: $\delta$H (DMSO $d_6$) 10.84 (s, 1H), 8.72 (2H, s), 8.15 (1H, d, J 7. $\delta$Hz), 7.55 (2H, d, J 8.4 Hz), 7.30 (2H, d, J 8.4 Hz), 4.55 (1H, m), 3.80 (3H, s), 3.78 (3H, s), 3.12 (1H, dd, J 13.8, 4.5 Hz), 3.01 (1H, dd, J 13.8, 10.3 Hz)); m/z (EI$^+$, 70V) 493.

EXAMPLE 53

S-Ethyl 3-[4-N-methyl-(3,5-dichloropyrid-4-ylcarboxamido)-phenyl]-2-(N-methyl-4,6-dimethoxy-1,3,5-triazin-2-ylamino)propionate To a solution of the ethyl ester analogue of the compound of Example 50 (310 mg, 0.59 mmol) in DMF (10 ml) was added cesium carbonate (388 mg, 1.18 mmol) and iodomethane (390 µl, 590 mmol) and the mixture was stirred at room temperature for 16 h. The reaction was concentrated in vacuo and extracted with ethyl acetate (50 ml). The organics were washed with water (2×50 ml), dried (Na$_2$SO$_4$) and evaporated. The residue was chromatographed (silica; EtOAc/Hexane 1:1) to give the title compound as a white solid (100 mg, 31%): $\delta$H (CDCL$_3$) 8.35 (1H, d), 7.20 (2H, d), 7.00 (2H, d), 5.10 (1H, m), 4.10 (2H, m), 4.00 (3H, s), 3.90 (3H, s), 3.49 (3H, s), 3.40 (1H, m), 3.30 (1H, m), 2.80 (3H, m), 1.20 (3H, m); m/z (EI$^+$, 70V) 549.

EXAMPLE 54

S-3-[4-N-Methyl-(3,5-dichloropyrid-4-ylcarboxamido)-phenyl]-2-(N-methyl-4,6-dimethoxy-1,3,5-triazin-2-ylamino)propanoic acid The title compound was prepared from the compound of Example 53 in an analogous manner to Example 2: $\delta$H (DMSO $d_6$) 8.37, (1H, s), 8.32 (1H, s), 7.18 (2H, d, J 8.4 Hz), 7.11 (2H, d, J 8.4 Hz), 5.24 (1H, dd, J 11.0, 5.3 Hz), 3.85 (6H, s), 3.36 (3H, s), 3.19 (2H, m), 2.77 (3H, s); m/z (EI$^+$, 70V) 521.

EXAMPLE 55

S-Ethyl [4-N-Methyl-(3,5-dichloropyrid-4-ylcarboxamido)-phenyl]-2-[(6-chloropyridazin-3-yl)amino]propionate A solution of the compound of Intermediate 3 (420 mg, 1 mmol) in CH$_3$CN (2 ml) was treated with DIPEA (0.36 ml, 2.1 mmol) and 3,6-dichloropyridazine (164 mg, 1.1 mmol) and heated to reflux temperature for 36 h. The solvent was removed in vacuo, the residue re-dissolved in EtOH (2.5 ml) and a further portion of pyridazine (82 mg, 0.55 mmol) and DIPEA (0.18 ml, 1.1 mmol) were added. The resulting mixture was heated to reflux for 4$\delta$H, the solvent was removed in vacuo and the residue was dissolved in EtOAc (20 ml) and washed with 10% citric acid (2×10 ml), NaHCO$_3$ (2×10 ml) and brine (10 ml), dried (MgSO$_4$) and the solvent removed in vacuo. The product was purified by chromatography (silica 2–5% MeOH/DCM) to give the title compound as a white solid (80 mg, 16%): $\delta$H (DMSO $d_6$) 10.85 (1H, s), 8.77 (2H, s), 7.56 (2H, d, J 8.5 Hz), 7.50 (1H, d, J 7.7 Hz), 7.39 (1H, d, J 9.3 Hz), 7.26 (2H, d, J 8.5 Hz), 7.02 (1H, d, J 9.3 Hz), 4.20 (1H, m), 4.06 (2H, q, J 7.1 Hz), 3.10 (2H, m), 1.12 (3H, t, J 7.1 Hz); m/z (EI$^+$, 60V) 494.

EXAMPLE 56

S-[4-(3,5-Dichloropyrid-4-ylcarboxamido)phenyl]-2-[(6-chloropyridazin-3-yl)amino]propanoic acid The title compound (50 mg, 79%) was prepared from the compound of Example 55 by hydrolysis in a similar manner to Example 2 (67 mg, 0.14 mmol): $\delta$H (DMSO $d_6$) 10.84 (1H, s), 8.77 (2H, s), 7.55 (2H, d, J 8.5 Hz), 7.37 (1H, d, J 9.3 Hz) 7.35 (1H, m), 7.26 (2H, d, J 8.5 Hz), 7.01 (1H, d, J 9.3 Hz), 4.67 (1H, m), 3.17 (1H, dd, J 18.8, 5.0 Hz), 2.96 (1H, dd, J 22.6, 8.9 Hz); m/z (EI$^+$, 60V) 466.

EXAMPLE 57

S-Ethyl-3-(4-nitrophenyl)-2-[(4,6-dimethoxy-1,3,5-triazin-2-yl)amino]propionate

2-Chloro-4,6-dimethoxy-1,3,5-triazine (8.05 g, 45.8 mmol) was added to a solution of (S)-4-nitrophenylalanine ethyl ester hydrochloride (5.0 g, 38.2 mmol) and DIPEA (13.6 ml, 78.3 mmol) in acetonitrile (80 ml) and the reaction was stirred at room temperature for 16 h, concentrated in vacuo and the residue partitioned between EtOAc (100 ml) and NaHCO$_3$ solution (100 ml). The organic layer was washed with 10% citric acid solution (100 ml), NaHCO$_3$ solution (100 ml) and water (100 ml), dried (MgSO$_4$) and concentrated in vacuo. The crude product was purified by chromatography (silica; EtOAc/Hexane 1:1) to give the title compound (6.66 g, 97%): δH (CDCL$_3$) 8.10 (2H, d, J 9.0 Hz), 7.30 (2H, d, J 9.0 Hz), 6.10 (1H, m), 5.0 (1H, m), 4.1 (2H, q, J 7.1 Hz), 3.92 (3H, s), 3.90 (3H, s), 3.30 (2H, m), 1.25 (3H, t, J 7.1 Hz); m/z (E$^+$, 70V) 378.

EXAMPLE 58

S-Ethyl-3-(4-aminophenyl)-2-[(4,6-dimethoxy-1,3,5-triazin-2-yl)amino]propionate

Palladium (10% on charcoal) (660 mg) was added to a solution of the compound of Example 57 (6.66 g, 24.3 mmol) in EtOH (100 ml) and stirred under an atmosphere of hydrogen for 16 h. The catalyst was removed by filtration and the solution concentrated in vacuo to give the title compound as a pink solid (5.26 g, 86%) which was used without further purification: δH (CDCL$_3$) 6.90 (2H, d), 6.60 (2H, d), 5.75 (1H, d), 4.90 (1H, m), 4.10 (2H, q), 3.95 (3H, s), 3.90 (3H, s), 3.10 (2H, m), 1.30 (3H, t); m/z (ES$^+$, 70V) 348.

EXAMPLE 59

S-Ethyl-3-[4-(2,6-dichlororphenylcarboxamido)phenyl]-2-[(4,6-dimethoxy-1,3,5-triazin-2-yl)amino]propionate 2,6-Dichlorobenzoyl chloride (0.22 ml, 1.5 mmo) was added to a solution of the compound of Example 58 (0.50 g, 1.4 mmol) and NMM (0.17 ml, 1.5 mmol) in DCM (10 ml). The reaction was stirred at room temperature for 72 h, then partitioned between DCM (50 ml) and NaHCO$_3$ solution (50 ml). The organic layer was washed with 10% citric acid solution (50 ml), NaHCO$_3$ solution (50 ml) and water (50 ml), dried (MgSO$_4$) and concentrated in vacuo to give the title compound as a pink solid (0.61 g, 82%) which was used without further purification: δH (CDCL$_3$) 7.60 (2H, d), 7.30 (3H, m), 7.10 (2H, d), 5.90 (1H, d), 4.90 (1H, m), 4.20 (2H, m), 3.90 (3H, s), 3.89 (3H, s), 3.20 (2H, m), 1.25 (3H, m); m/z (EI$^+$, 70V) 520.

EXAMPLE 60

S-3-[4-(2,6-Dichlorophenylcarboxamido)phenyl]-2-[(4,6-dimethoxy-1,3,5-triazin-2-yl)amino]propanoic acid The title compound was prepared by hydrolysis in a similar manner to Example 2 from the compound of Example 59: δH (DMSO d$_6$) 10.70 (1H, s), 8.15 (2H, d), 7.50 (6H, m), 7.25 (2H, d), 4.50 (1H, m), 3.75 (6H, m), 3.00 (2H, m); m/z (EI$^+$, 60V) 492.

EXAMPLE 61

S-Ethyl-3-[4-(2-fluoro-6-trifluoromethylphenylcarboxamido)phenyl]-2-[(4,6-dimethoxy-1,3,5-triazin-2-yl)amino]propionate The title compound was prepared in an analogous manner to the compound of Example 59 using 2-fluoro-6-trifluoromethylbenzoyl chloride: δH (CDCL$_3$) 7.6 (51H, m), 7.40 (1H, m), 7.10 (2H, d J 8.0 Hz), 5.90 (1H, d, J 6.0 Hz), 5.0 (1H, m), 4.2 (2H, q), 3.90 (2×3H s), 3.20 (2H, m), 1.25 (3H, t); m/z (EI$^+$, 70V) 538.

EXAMPLE 62

S-3-[4-(2-Fluoro-6-trifluoromethylphenylcarboxamido)phenyl]-2-[(4,6-dimethoxy-1,3,5-triazin-2-yl)amino]propanoic acid The title compound was prepared from the compound of Example 61 by hydrolysis in a similar manner to Example 2: δH (DMSO d$_6$) 8.10 (2H, m), 7.80 (3H, m), 7.50 (2H, m), 7.30 (2H, m), 4.50 (1H, m), 3.70 (6H, s), 3.00 (2H, m); m/z (EI$^+$, 70V) 510.

EXAMPLE 63

S-Ethyl-3-[4-(4,6-dimethoxy-1 3 5-triazin-2-yl)aminophenyl]-2-[(4,6-dimethoxy-1,3,5-triazin-2-yl)amino]propionate 2-Chloro-4,6-dimethoxy-1,3,5-triazine (0.30 g, 1.7 mmol) was added to a solution of the compound of Example 58 (0.50 g, 1.4 mmol) and DIPEA (0.60 ml, 3.2 mmol) in CH$_3$CN (10 ml). The reaction was stirred at room temperature for 72 h, then concentrated in vacuo, partitioned between EtOAc (50 ml) and NaHCO$_3$ solution (50 ml). The organic layer was washed with 10% citric acid solution (50 ml), NaHCO$_3$ solution (50 ml) and water (50 ml), dried (MgSO$_4$) and concentrated in vacuo to give the title compound as an off white solid (0.23 g, 32%) which was used without further purification: δH (CDCL$_3$) 7.5 (2H, d, J 9.0 Hz), 7.10 (2H, d, J 9.0 Hz), 6.05 (1H, d, J 6.0 Hz), 5.0 (1H, m), 4.15 (2H, q), 4.05 (6H, s), 3.95 (6H, s), 3.20 (2H, m), 1.25 (3H, m); m/z (EI$^+$, 70V) 487.

EXAMPLE 64

S-3-[-4-(4,6-Dimethoxy-1,3,5-triazin-2-yl)aminophenyl]-2-[(4,6-dimethoxy-1,3,5-triazin-2-yl-)amino]propanoic acid The title compound was prepared from the compound of Example 63 by hydrolysis in a similar manner to Example 2: δH (DMSO d$_6$) 10.00 (1H, s), 8.20 (2H, d), 7.55 (2H, d), 7.20 (2H, d), 4.55 (1H, m), 3.90 (6H, s), 3.80 (6H, s), 3.00 (2H, m); m/z (EI⁺, 70V) 459.

EXAMPLE 65

S-Ethyl 3-[4-(4,6-dimethoxy-1,3,5-triazin-2-yl)phenoxy]-2-[(4,6-dimethoxy-1,3,5-triazin-2-ylamino] propionate A solution of Intermediate 11 (0.50 g, 1.43 mmol) in DMF (10 ml) was treated with caesium carbonate (0.94 g, 2.86 mmol) and stirred at room temperature for 15 min. 2-Chloro-4,6-dimethoxy-1,3,5-triazine (0.25 g, 1.43 mmol) was added and the reaction stirred for 16 h then concentrated in vacuo, and partitioned between EtOAc (50 ml) and water (50 ml). The organic layer was separated, dried (MgSO₄) and concentrated in vacuo to give the title compound as an off-white solid (0.47 g, 67%): δH (DMSO d₆) 7.25 (2H, d, J 7.0 Hz), 7.20 (2H, d, J 7.0 Hz), 5.90 (1H, d), 5.00 (1H, m), 4.20 (2H, m), 4.00 (12H, s), 3.20 (2H, m), 1.20 (3H, t, J 7.1 Hz); m/z (EI⁺, 70V) 488.

EXAMPLE 66

S-3-[4-(4,6-Dimethoxy-1,3,5-triazin-2-yl)phenoxy]-2-[(4,6-dimethoxy-1,3,5-triazin-2-yl))amino]propanoic acid The title compound was prepared from the compound of Example 65, by hydrolysis in a similar manner to Example 2: δH (DMSO d₆) 8.00 (1H, s), 7.35 (2H, d, J 8.0 Hz), 7.10 (2H, d, J 8.0 Hz), 4.50 (1H, m), 3.85 (6H, s), 3.79 (6H, s), 3.77 (6H, s), 3.20 (2H, m); m/z ($^{EI+'}$, 70V) 460.

EXAMPLE 67

S-Ethyl 3-[4-(2,6-dichlorobenzyl)phenoxy2)-2-[(4,6-dimethoxy-1,3,5-triazin-2-yl))amino]propionate A solution of Intermediate 11 (0,50 g, 1.43 mmol) in DMF (10 ml) was treated with caesium carbonate (0.948, 2.86 mmol) and stirred at room temperature for 15 min. 2,6-Dichlorobenzyl bromide (0.38 g, 1.58 mmol) was added and the reaction stirred for 16 h then concentrated in vacuo, and partitioned between EtOAc (50 ml) and water (50 ml). The organic layer was separated, washed with water (2×50 ml), dried (MgSO₄) and concentrated in vacuo. The residue was purified by chromatography (silica; EtOAc/Hexane 1:1) to give the title compound as an oil (0.26 g, 36%): δH (DMSO d₆) 7.45 (1H, m), 7.40 (1H, m), 7.35 (1H, m), 7.10 (2H, d), 6.90 (2H, d), 5.8 (1H, d), 5.25 (2H, s), 4.10 (2H, m), 3.90 (6H, s), 3.10 (2H, m), 1.3 (3H, m); m/z (EI⁺, 70V) 507.

EXAMPLE 68

S-3-[4-(2,6-Dichlorobenzyl)phenoxy]-2-[(4,6-dimethoxy-1,3,5-triazin-2-yl]amino]propanoic acid The title compound was prepared from the compound of Example 67, by hydrolysis in a similar manner to Example 2: δH (DMSO d₆) 8.10 (1H, d), 7.50 (2H, m), 7.45 (1H, m), 7.25 (2H, d, J 8.0 Hz), 6.95 (2H, d, J 8.0 Hz), 5.15 (2H, m), 4.50 (1H, m), 3.80 (3H, s), 3.75 (3H, s), 3.00 (2H, m); m/z (EI⁺, 70V) 479.

EXAMPLE 69

S-3-[4-(3,5-Dichloropryid-4-ylcarboxamido)phenyl]-2-]3-(propylsulphonyl)pyrazin-2-ylamino]propanoic acid The title compound was prepared in an analogous manner to the compound of Example 1 starting from Intermediate 3 and Intermediate 12, followed by hydrolysis: δH (DMSO d₆) 10.86 (1H, s), 8.77 (2H, s), 8.40 (1H, d, J 2.3 Hz), 7.99 (1H, d, J 2.3 Hz), 7.55 (2H, d, J, 8.5 Hz), 7.37 (1H, d, J 7.0 Hz), 7.18 (2H, d, J 8.5 Hz), 4.80 (1H, br. q), 3.38–3.22 (3H, m), 3.10 (1H, dd, J 13.9, 7.0 Hz), 7.18 (2H, d, J 8.5 Hz), 4.80 (1H, br. q), 3.38–3.22 (3H, m), 3.10 (1H, dd, J 13.9, 7.0 Hz), 1.55–1.46 (2H, m), 0.88 (3H, t, J 7.4 Hz); m/z (EI⁺, 70V) 538.

EXAMPLE 70

S-3-[4-(3,5-Dichlorolopyrid-4-ylcarboxamido)phenyl]-2-[3-chloropyrazin-2-ylamino]propanoic acid The title compound was prepared in an analogous manner to the compound of Example 5 starting from Intermediate 3 and 2,3-dichloropyrazine, followed by hydrolysis: δH (DMSO d₆) 12.81 (1H, br. s), 10.83 (1H, s), 8.77 (2H, s), 7.99 (1H, d, J 2.7 Hz), 7.61 (1H, d, J 2.7 Hz), 7.54 (2H, d, J 8.5 Hz), 7.28 (2H, d, J 8.5 Hz), 6.87 (1H, d, J 7.9 Hz), 4.68–4.61 (1H, m), 3.22 (2H, m); m/z (EI⁺, 70V) 466.

EXAMPLE 71

S-3-[4-(3,5-Dichloropyrid-4-ylcarboxamido)phenyl]-2-[6-chloropyrazin-2-ylamino]propanoic acid The title compound was prepared in an analogous manner to the compound of Example 5 starting from Intermediate 3 and 2,6-dichloropyrazine, followed by hydrolysis: δH (DMSO d⁶) 12.82 (1H, br. s), 10.84 (1H, s), 8.77 (2H, s), 7.97 (1H, s), 7.84 (1H, d, J 8.0 Hz), 7.72 (1H, s), 7.54 (2H, d, J 8.5 Hz), 7.27 (2H, d, J 8.5 Hz), 4.51 (1H, ddd, J 8.9, 8.0, 4.9 Hz), 3.15 (1H, dd, J 13.9, 4.4 Hz), 2.96 (1H, dd, J 13.9, 9.1 Hz); m/z (EI⁺, 70V) 466.

EXAMPLE 72

S-Ethyl 3-[4-(3,5-Dichloropyrid-4-ylcarboxamido) phenyl]-2-(3-chloroquinoxalin-2ylamino]propionate The title compound was prepared in an analogous manner to the compound of Example 5 starting from Intermediate 3 and 2,3-dichloroquinoxaline. The product contains some ethoxyethylester as a result of transesterification in the ethoxyethanol used as solvent in this case: δH (DMSO d₆) 10.38 (1H, s), 8.76 (2H, s), 7.76 (1H, d, J 8.2 Hz), 7.65–7.41 (6H, m), 7.32 (2H, d, J 8.4 Hz), 4.82–4.75 (1H, m), 4.17–4.06 (2H, m), 3.40–3.20 (2H, m), 1.14 (3H, t, J 7.1 Hz); m/z (EI⁺, 70V) 544. For the ethoxyethyl ester: δH (DMSO d₆) 3.47–3.42 (m). 0.97 (3H, t, J 7.0 Hz); m/z (EI⁺, 70V) 588.

EXAMPLE 73

S-3-[4-(3,5-Dichloropyrid-4-yl)carboxamido)phenyl]-2-[3-chloroquinoxalin-2-ylamino]propanoic acid The title compound was prepared from the compound of Example 72 by hydrolysis: δH (DMSO d$_6$) 12.84 (1H, br. s), 10.81 (1H, s), 8.76 (2H, s), 7.76 (1H, d, J 8.2 Hz), 7.63–7.61 (2H, m), 7.54 (1H, d, J 8.5 Hz), 7.46–41 (1H, m), 7.33–7.25 (3H, m), 4.86–4.79 (1H, m), 3.30–3.26 (2H, m); m/z (EI$^+$, 70V) 516.

EXAMPLE 74

S-3-[4-(3,5-Dichloropyrid-4-ylcarboxamido)phenyl]-2-[3-phenoxyquinoxalin-2-ylamino]propanoic acid The title compound was prepared in an analogous manner to the compound of example 5 starting from Intermediate 3 and Intermediate 14 followed by hydrolysis: δH (DMSO d$_6$) 12.90 (1H, br. s), 10.83 (1H, s), 8.76 (2H, s), 7.57–7.23 (14H, m), 4.91–4.84 (1H, m), 3.30 (2H, br. d J 6.6 Hz); m/z (EI$^+$, 70V) 574.

EXAMPLE 75

S-Ethyl 3-[4-(3,5-Dichloropyrid-4-ylcarboxamido)phenyl]-2-[3-morpholinoquinoxalin-2-ylamino]propionate A mixture of the compound of Example 73 (300 mg, 0.55 mmol), morpholine (58 μl, 0.66 mmol) and DIPEA (192 μlL, 1.1 mmol) in ethoxyethanol (2 ml) was heated at reflux overnight. The solvent was removed in vacuo. The residue was dissolved in DCM, washed with dil. HCl, dried (Na$_2$SO$_4$) and evaporated in vacuo. Column chromatography (silica; EtOAc/Hexane 6:4) gave the title compound (280 mg) as a brown oil, which contains some of the corresponding ethoxyethyl ester from transesterification: δH (DMSO d$_6$) 10.84 (1H, s), 8.77 (2H, s), 7.61–7.27 (6H, m), 6.70 (1H, d, J 7.81 Hz), 4.75 (1H, m), 4.21–4.07 (2H, m and ethoxyethyl ester), 3.86–3.80 (2H, m), 3.71–3.66 (2H, m), 3.50 (m, ethoxyethyl ester), 3.30 (2H, m), 3.12–3.17 (2H, m), 2.97–2.91 (2H, m), 1.16 (t, J 7.1 Hz) and 1.00 (t, J 7.0 Hz) together (3H); m/z (EI$^+$, 70V) 595, 639 (ethoxyethyl ester).

EXAMPLE 76

S-3-(4-(3,5-Dichloropyrid-4-ylcarboxamido)]phenyl]-2-[3-morpholinoquinoxalin-2-ylamino]propanoic acid The title compound was prepared by starting from the compound of Example 75 followed by hydrolysis: δH (DMSO d$_6$) 10.83 (1H, s), 8.76 (2H, s), 7.61–7.26 (δH, m), 6.55 (1H, d, J 7. δHz), 4.74 (1H, m), 3.84–3.79 (2H, m), 3.69–3.64 (2H, m), 3.30–3.20 (2H, m), 3.20–3.10 (2H, m), 2.93–2.88 (2H, m); m/z (EI$^+$, 70V) 567.

EXAMPLE 77

Ethyl 2-[4-(3,5-dichlorolpyrid-4-ylcarboxamido) benzyl]-3-[6-(propylsulphonyl)-pyrimidin-4-ylamino]propionate A mixture of Intermediate 19 (440 mg, 1.11 mmol) Intermediate 13 (271 mg, 0.93 mmol) and DIPEA (193 μL, 1.11 mmol) in CH$_3$CN (5 ml) was stirred at room temperature for 2 h. The solvent was removed in vacuo and the residue dissolved in DCM, washed with dil. HCl, dried (Na$_2$SO$_4$) and evaporated in vacuo. Column chromatography (silica; MeOH/DCM 5:95) gave the title compound as a colourless oil (400 mg): δH (DMSO d$_6$) 10.85 (1H, s), 8.78 (2H, s), 8.30(1H, br. t, J 5.7 Hz), 7.55 (2H, d, J 8.5 Hz), 7.20 (2H, d, J 8.5 Hz), 7.10 (1H, s), 3.97 (2H, q, J 7.4 Hz), 3.60 (2H, br. m), 3.36–3.27 (4H, m), 2.99, (1H, m), 1.58 (2H, sext, J 7.5 Hz), 1.03 (3H, t, J 7.1 Hz), 0.93 (3H, t, J 7.4 Hz): m/z (EI$^+$, 70V) 580.

EXAMPLE 78

2-[4-(3,5-Dichloropyrid-4-ylcarboxamido)benzyl]-3-[6-(propylsulphonyl-pyrimidin-4-ylamino]propanoic acid The title compound was prepared by hydrolysis from the compound of Example 77 in a similar manner to Example 2: δH (DMSO d$_6$) 12.38 (1H, br. s), 10.85 (1H, s), 8.78 (2H, s), 8.57 (1H, s), 8.30 (1H, br, m), 7.55 (2H, d, J 38.5 Hz), 7.21 (2H, d, J 8.5 Hz), 7.12 (1H, s), 3.55 (2H, br. m), 3.33–3.29 (4H, m), 2.95–2.83 (1H, m), 1.59 (2H, sext, J 7.6 Hz), 0.94 (3H, t, J 7.4 Hz): m/z (EI$^+$, 70V) 552.

EXAMPLE 79

Ethyl 3-[4-(3,5-dichloropyrid-4-ylcarboxamido) phenyl]-2-(3-benzyloxybenzeneamino)propionate A solution of Intermediate 20 (500 mg, 1.3 mmol), 3-benzyloxyaniline (1.1 equiv) and rhodium (II) acetate dimer (5 mol %) in anhydrous toluene (20 ml) were stirred at 80° for 7 h. The mixture was cooled and the volatiles removed in vacuo. The residue was purified by chromatography (silica; 1% MeOH/DCM) to give the title compound (500 mg, 70%): δH (CDCL$_3$) 8.50 (2H, s), 8.06 (1H, br. s), 7.49 (2H, d, J 8.5 Hz), 7.43–7.26 (6H, m), 7.14 (2H, d, J 8.5 Hz), 7.05 (1H, t, J 8.5 Hz), 6.37 (1H, d, J 7.3 Hz), 6.24 (2H, m), 5.00 (2H, s), 4.40–4.08 (4H, m), 3.13 (1H, dd, J 13.4, 7 Hz), 3.02 (1H, dd, J 13.4, 5.9 Hz), 1.20 (3H, t, J 7.2 Hz): m/z (EI$^+$, 70V) 564.

EXAMPLE 80

Ethyl 3-[4-(3,5-dichloropyrid-4-ylcarboxamido) phenyl]-2-(3-propylthiobenzeneamino)propionate The title compound was prepared by a similar procedure to the compound of Example 79, starting from 3-propylthioaniline: δH (CDCL$_3$) 8.56 (2H, s), 7.72–7.58 (2H, m), 7.53 (2H, d, J 8.5 Hz), 7.10 (2H, d, J 8.4 Hz), 7.04 (1H, t, J 7.9 Hz), 6.68 (1H, d, J 7.9 Hz), 6.57 (1H, s), 6.42 (1H, d), 4.40–4.10 (3H, m), 3.25–3.07 (2H, m), 2.83 (2H, t, J 7.3 Hz), 1.63 (2H, m), 1.21 (3H, t, J 6. δHz), 1.01 (3H, t, J 7.4 Hz): m/z (EI$^+$, 70V) 532.

EXAMPLE 81

Ethyl 3-[4-(3,5-dichloropyrid-4-ylcarboxamido) phenyl]-2-(4-ethoxycarbonylbenzeneamino)propionate The title compound was prepared by a similar procedure to the compound of Example 79, starting from ethyl 4-aminobenzene carboxylate: $\delta H$ ($CDCL_3$) 8.58 (2H, s), 7.85 (2H, d, J 8. δHz), 7.56–7.51 (3H, m), 7.15 (2H, d, J 8.5 Hz), 6.56 (1H, d, J 8. δHz), 4.70–4.60 (1H, br. m), 4.55–4.45 (1H, br. m), 4.32 (2H, q, J 7.2 Hz), 4.16 (2H, q, J 7.1 Hz), 3.30–3.14 (2H, m), 1.33 (3H, t, J 7.2 Hz), 1.23 (3H, t, J 7.1 Hz): m/z ($EI^+$, 70V) 530.

EXAMPLE 82

Ethyl 3-[4-(3,5-dichloropyrid-4-ylcarboxamido) phenyl]-2-(3-propylsulphonylbenzeneamino)propionate The title compound was prepared by oxidation of the compound of Example 80 with mCPBA: $\delta H$ ($CDCL_3$) 8.47 (2H, s), 8.36 (1H, br. s), 7.51 (2H, d, J 8.5 Hz), 7.30 (1H, t, J 7.9 Hz), 7.12 (2H, d, J 8.4 Hz), 7.01 (1H, m), 6.78 (1H, m), 4.61 (1H, br. m), 4.40 (1H, br. m), 4.10 (2H, q, J 5.9 Hz), 3.15 (1H, dd, J 13.9, 5.6 HZ), 3.05 (1H, dd, J 13.9, 6.3 Hz), 2.95 (2H, m), 1.61 (2H, m), (3H, t, J 7.2 Hz), 0.94 (3H, t, J 7.4 Hz): m/z ($EI^+$, 70V) 564.

EXAMPLE 83

Ethyl 3-[4-(3,5-dichloropyrid-4-ylcarboxamido) phenyl]-2-(3-propylsulphinylbenzeneamino)propionate The title compound was prepared by oxidation of the compound of Example 80 with mCPBA: $\delta H$ ($CDCL_3$) 9.11 (1H, d, J 8.3 Hz), 8.44 (2H, s), 7.56 (2H, d, J 8.0 Hz), 7.21 (1H, t, J 7. δHz), 7.12 (2H, m), 6.80–6.64 (3H, m), 4.65–4.35 (2H, br. m), 4.10 (2H, q, J 7.1 Hz), 3.20–3.00 (2H, m), 2.70–2.50 (2H, m), 1.80–1.50 (2H, m), (3H, t, J 8.7 Hz), 0.99 (3H, t, J 7.5 Hz): m/z ($EI^+$, 70V) 548.

EXAMPLE 84

Ethyl 3-[4-(3,5-dichloropyrid-4-ylcarboxamido) phenyl]-2-(4-ethylacetatobenzeneamino)propionate The title compound was prepared by a similar procedure to the compound of Example 79, starting from ethyl 4-aminobenzene acetate: $\delta H$ ($CDCL_3$) 8.57 (2H, s), 7.81 (2H, d, J 8.5 Hz), 7.17 (2H, d, J 8.5 Hz), 7.06 (2H, d, J 8. δHz), 6.55 (2H, d, J 8.6 Hz), 4.30 (1H, br. m), 4.10 (4H, m), 3.48 (2H, s), 3.25–3.00 (2H, m), 1.20 (6H, m): m/z ($EI^+$, 70V) 544.

EXAMPLE 85

Ethyl 3-[4-(3,5-dichloropyrid-4-ylcarboxamido) phenyl]-2-(3-acetylbenzeneamino)propionate The title compound was prepared by a similar procedure to the compound of Example 79, starting from 3-amino acetophenone: $\delta H$ ($CDCL_3$) 8.56 (2H, s), 7.65 (1H, br. m), 7.40–7.10 (5H, m), 6.80 (1H, m), 4.50–4.30 (2H, br. m), 4.16 (2H, q, J 7.2 Hz), 3.25–3.10 (2H, m), 2.54 (3H, s), 1.22 (3H, t, J 7.2 Hz): m/z ($EI^+$, 70V).

EXAMPLE 86

Ethyl 3-[4-(3,5-dichloropyrid-4-ylcarboxamido phenyl]-2-(2-chloropyridine-3-amino)propionate The title compound was prepared by a similar procedure to the compound of Example 79, starting from 3-amino-2-chloro-pyridine: $\delta H$ ($CDCL_3$) 8.56 (2H, s), 7.78 (1H, br. s), 7.70 (1H, d, J 4.7 Hz), 7.56 (2H, d, J 8.5 Hz), 7.20 (2H, d, J 8.5 Hz), 7.04 (1H, m), 6.78 (1H, m, J 8.0, 1.3 Hz), 4.87 (1H, br. m), 4.40–4.15 (3H, m), 3.18 (1H, dd, J 14.0, 5.7 Hz), 3.11 (1H, dd, J 13.7, 6.6 Hz), 1.23 (3H, t, J, 7.1 Hz): m/z ($EI^+$, 70V) 493.

EXAMPLE 87

Ethyl 3-[4-(3,5-dichloropyrid-4-ylcarboxamido) phenyl]-2-(3-benzoylbenzeneamino)propionate The title compound was prepared by a similar procedure to the compound of Example 79, starting from 3-amino benzophenone: $\delta H$ ($CDCL_3$) 8.55 (2H, s), 7.72 (2H, d, J 8.5 Hz), 7.70–7.40 (6H, m), 7.30–7.00 (6H, m), 6.80 (1H, m), 4.40 (1H, br. m), 4.15 (2H, q, J 7.2 Hz), 3.40–3.20 (2H, m), 1.20 (3H, t, J 7.2 Hz): m/z ($EI^+$, 70V) 562.

EXAMPLE 88

Ethyl 3-[4-(3,5-dichloropyrid-4-ylcarboxamido) phenyl]-2-(3-ethoxycarbonylbenzeneamino)propionate The title compound was prepared by a similar procedure to the compound of Example 79, starting from ethyl 3-aminobenzoate: $\delta H$ ($CDCL_3$) 8.44 (2H, s), 7.50 (2H, d, J 8.4 Hz), 7.35 (1H, d, J 7.7 Hz), 7.30–7.10 (4H, m), 6.77 (1H, m), 4.40 (1H, br. s), 4.31 (2H, q, J 7.2 Hz), 4.09 (2H, m), 3.25–3.00 (2H, m), 1.33 (3H, t, J 7.2 Hz), 1.21 (3H, t, J 7.2 Hz): m/z ($EI^+$, 70V) 530.

EXAMPLE 89

Ethyl 3-[4-(3,5-dichloropyrid-4-ylcarboxamido) phenyl]-2-(5-chloro-4 propylthiolpyridine-2-amino) propionate The title compound was prepared by a similar procedure to the compound of Example 79, starting from Intermediate 23: $\delta H$ ($CDCL_3$) 8.53 (2H, s), 8.11 (1H, s), 7.87 (1H, s), 7.54 (2H, d, J 8.4 Hz), 7.19 (2H, d, J 8.4 Hz), 6.17 (1H, s), 4.80 (1H, br. m), 4.21 (2H, q, J 7.1 Hz), 3.21 (1H, dd, J 14.0, 5.5 Hz), 3.09 (1H, dd, J 14.0, 5.7 Hz), 2.80 (2H, t, J 7.2 Hz), 1.74 (2H, m), 1.30 (3H, t, J 7.1 Hz), 1.07 (3H, t, J 7.3 Hz): m/z ($EI^+$, 70V) 568.

EXAMPLE 90

Ethyl 3-[4-(3,5-dichloropyrid-4-ylcarboxamido) phenyl]-2-(5-chloro-4 propylsulphinylpyridine-2-amino)propionate The title compound was prepared by oxidation of the compound of Example 89 with mCPBA: $\delta H$ ($CDCL_3$) 8.55 (2H, s), 7.94 (2H, m), 7.52 (2H, d, J 8.4 Hz), 7.12 (2H, m), 6.82 (1H, d), 4.90 (1H, m), 4.20 (2H, m), 3.40–3.00 (3H, m), 2.90–2.70 (1H, m), 2.00–1.60 (2H, m), 1.25 (3H, t, J 7.2 Hz), 1.07 (3H, t, J 7.2 Hz): m/z ($EI^+$, 70V) 584.

EXAMPLE 91

Ethyl 3-[4-(3,5-dichloropyrid-4-ylcarboxamido) phenyl]-2-(5-chloro-4-propylsulphonylpyridine-2-amino)propionate The title compound was prepared by oxidation of the compound of Example 89 with m-chloroperoxybenzoic acid: δH (CDCL$_3$) 8.56 (2H, s), 8.19 (1H, s), 7.63 (1H, br. s), 7.51 (2H, d, J 8.4 Hz), 7.17 (2H, d, J, 8.4 Hz), 7.14 (1H, s), 5.34 (1H, br. m), 4.21 (2H, q, J 7.2 Hz), 3.30 (2H, t, J 7.9 Hz), 3.35–3.10 (2H, m), 1.70 (2H, m), 1.29 (3H, t, J 7.2 Hz), 1.01 (3H, t, J 7.5 Hz): m/z (EI$^+$, 70V) 598.

EXAMPLE 92

Ethyl 3-[4-(3,5-dichloropyrid-4-ylcarboxamido) phenyl]-2-(5-chloropyridine-2-amino)propionate The title compound was prepared by a similar procedure to the compound of Example 79, starting from 2-amino-5-chloro-pyridine: δH (CDCL$_3$) 8.56 (2H, s), 8.03 (1H, m), 7.59 (1H, m), 7.15 (2H, d, J 8.5 Hz), 6.37 (1H, d, J 8.9 Hz), 4.84 (1H, br. m), 4.15 (2H, q J 7.2 Hz), 3.30–3.10 (2H, m), 1.20 (3H, t, J 7.2 Hz).

EXAMPLE 93

Ethyl 3-[4-(3,5-dichloropyrid-4-ylcarboxamido) phenyl]-2-(4-propylthiopyridine-2-amino)propionate The title compound was prepared by a similar procedure to the compound of Example 79, starting from 2-amino-4-propylthio-pyridine: δH (CDCL$_3$) 8.51 (2H, s), 8.40 (1H, br. s), 7.81 (1H, d, J 5.6 Hz), 7.49 (2H, d, J 8.5 Hz), 7.13 (2H, d, J 8.5 Hz), 6.44 (1H, dd, J 5.6, 1.6 Hz), 6.19 (1H, d, J 1.2 Hz), 4.95–4.72 (2H, m), 4.15 (2H, q, J 7.1 Hz), 3.30–3.05 (2H, m), 2.80 (2H, t, J, 7.4 Hz), 1.70 (2H, m), 1.22 (3H, t, J 7.1 Hz), 1.01 (3H, t, J 7.4 Hz).

EXAMPLE 94

Ethyl 3-[4-(3,5-dichloropyrid-4-ylcarboxamido) phenyl]-2-(4-propylsulphonylpyridine-2-amino)propionate The title compound was prepared by oxone oxidation of the compound of Example 93: δH (CDCL$_3$) 8.56 (2H, s), 8.23 (1H, d, J 5.3 Hz), 7.68 (1H, br. m), 7.53 (2H, d, J 8.5 Hz), 7.20 (2H, d, J 8.5 Hz), 6.96 (1H, m), 6.90 (1H, s), 4.90 (1H, br. m), 4.19 (2H, q, J 7.1 Hz), 3.40–3.10 (2H, m), 3.01 (2H, m), 1.70 (2H, m), 1.25 (3H, t, J 7.2 Hz), 1.02 (3H, t, J 7.5 Hz): m/z (EI$^+$, 70V) 565.

EXAMPLE 95

Ethyl 3-[4-(3,5-dichloropyrid-4-ylcarboxamido) phenyl]-2-(5-methoxycarbonyl-4-propylthiopyridine-2-amino)propionate The title compound was prepared by a similar procedure to the compound of Example 79, starting from ethyl 2-amino-4-propylthio-pyridine-5-carboxylate: δH (CDCL$_3$) 8.65 (1H, s), 8.53 (2H, s), 8.05 (1H, br. s), 7.52 (2H, d, J 8.5 Hz), 7.20 (2H, d, J 8.5 Hz), 6.20 (1H, s), 5.62 (1H, br. m), 4.92 (1H, br. m), 4.20 (2H, q J 7.2 Hz), 3.90 (3H, s), 3.40–3.10 (2H, m), 2.72 (2H, t, J 7.4 Hz), 1.72 (2H, m), 1.22 (3H, t, J 7.2 Hz), 1.10 (3H, t, J 7.4 Hz).

EXAMPLE 96

Ethyl 3-[4-(3,5-dichloropyrid-4-ylcarboxamido) phenyl]-2-(5-methoxycarbonyl-4-propylsulphonylpyridine-2-amino)propionate The title compound was prepared by ozone oxidation of the compound of Example 95: isolated crude and used without further purification in Example 112.

EXAMPLE 97

3-[4-(3,5-Dichloropyrid-4-ylcarboxamido)phenyl]-2-(3-benzyloxybenzeneamino propanoic acid The title compound was prepared by lithium hydroxide hydrolysis of the compound of Example 79: δH (DMSO d$_6$) 10.84 (1H, s), 8.77 (2H, s), 7.53 (2H, d, J, 8.6 Hz), 7.42–7.26 (7H, m), 6.92 (1H, t, J 8.0 Hz), 6.17 (3H, m), 4.97 (2H, s), 4.05 (1H, br. m), 3.29–2.89 (2H, m): m/z (EI$^+$, 70V) 536.

EXAMPLE 98

3-[4-(3,5-Dichloropyrid-4-ylcarboxamido)phenyl]-2-3 propylthiobenzeneamino)propanoic acid The title compound was prepared by lithium hydroxide hydrolysis of the compound of Example 80: δH (DMSO d$_6$) 10.83 (1H, s), 8.77 (2H, s), 7.53 (2H, d, J 8.5 Hz), 7.27 (2H, d, J 8.5 Hz), 6.95 (1H, t, J 7.9 Hz), 6.52–6.30 (3H, m), 4.10 (1H, br. m), 3.20–2.90 (2H, m), 2.80 (2H, t, J 7.2 Hz), 1.52 (2H, m), 0.92 (3H, t, J 7.4 Hz): m/z (EI$^+$, 70V) 504.

EXAMPLE 99

3-[4-(3,5-Dichloropyrid-4-ylcarboxamido)phenyl]-2-(4-carboxybenzeneamino)propanoic acid The title compound was prepared by lithium hydroxide hydrolysis of the compound of Example 81: δH (DMSO d$_6$) 10.83 (1H, s), 8.77 (2H, s), 7.65 (2H, d, J 8.7 Hz), 7.53 (2H, d, J 8.5 Hz), 7.27 (2H, d, J 8.5 Hz), 6.76 (1H, d, J 8.6 Hz), 6.60 (2H, d, J 8.7 Hz), 4.22 (1H, br. m), 3.30–2.95 (2H, m): m/z (EI$^+$, 70V) 574.

EXAMPLE 100

3-[4-(3,5-Dichloropyrid-4-ylcarboxamido)phenyl]-2-(3-propylsulphonylbenzeneamino)propanoic acid The title compound was prepared by lithium hydroxide hydrolysis of the compound of Example 82: δH (DMSO d$_6$) 10.84 (1H, s), 8.77 (1H, s), 7.53 (2H, d, J 8.5 Hz), 7.29 (3H, m), 7.28 (1H, s), 7.01 (1H, d, J 7.6 Hz), 6.86 (1H, d, J 8.1 Hz), 6.55 (1H, d, J 8.9 Hz), 4.20 (1H, br. m), 3.17–3.11 (3H, m), 2.91 (1H, dd, J 13.8, 8.7 Hz), 1.48 (2H, m), 0.86 (3H, t, J 7.5 Hz): m/z (EI$^+$, 70V) 536.

EXAMPLE 101

3-[4-(3,5-Dichloropyrid-4-ylcarboxamido)phenyl]-2-(3-propylsulphinylbenzeneamino]propanoic acid The title compound was prepared by lithium hydroxide hydrolysis of the compound of Example 83: $\delta$H (DMSO d$_6$) 12.75 (1H, br. s), 10.89 (1H, s), 8.80 (2H, s), 7.55 (2H, d, J 8.5 Hz), 7.31 (2H, d, J 8.5 Hz), 7.21 (1H, t, J 7.9 Hz), 6.84 (1H, s), 6.76–6.68 (2H, m), 6.42 (1H, br. m), 3.33 (2H, t, J 8.9 Hz), 3.30–2.50 (4H, m), 1.80–1.30 (2H, m), 0.93 (3H, t, J 7.2 Hz): m/z (EI$^+$, 70V) 520.

EXAMPLE 102

3-[4-(3,5-Dichloropyrid-4-ylcarboxamido)phenyl]-2-(4-carboxymethylbenzeneamino)propanoic acid The title compound was prepared by lithium hydroxide hydrolysis of the compound of Example 84: $\delta$H (DMSO d$_6$) 10.83 (1H, s), 8.76 (2H, s), 7.53 (2H, d, J 8.5 Hz), 7.27 (2H, d, 1 8.5 Hz), 6.92 (2H, d, J 8.5 Hz), 6.51 (2H, d, J 8.5 Hz), 4.00 (1H, br. m), 2.95 (2H, m): m/z (EI$^+$, 70V) 488.

EXAMPLE 103

3-[4-(3,5-Dichloropyrid-4-ylcarboxamido)phenyl]-2-[3-acetylbenzeneamino)propanoic acid The title compound was prepared by lithium hydroxide hydrolysis of the compound of Example 85: $\delta$H (DMSO d$_6$) 10.84 (1H, s), 8.77 (2H, s), 7.53 (2H, d, J 8.5 Hz), 7.29 (2H, d, J 8.5 Hz), 7.30–7.10 (3H, m), 6.82 (1H, m), 6.20 (1H, br. m), 4.17 (1H, br. m), 3.20–2.90 (2H, m): m/z (EI$^+$, 70V) 472.

EXAMPLE 104

3-[4-(3,5-Dichloropyrid-4-ylcarboxamido)phenyl]-2-(2-chloro-pyridine-3-amino)propanoic acid The title compound was prepared by lithium hydroxide hydrolysis of the compound of Example 86: $\delta$H (DMSO d$_6$) 10.85 (1H, s), 8.77 (2H, s), 7.75–7.50 (3H, m), 7.40–7.10 (4H, m), 5.28 (1H, d, J 8.4 Hz), 4.40 (1H, br. m), 3.15 (2H, d, J 5.9 Hz): m/z (EI$^+$, 70V) 467.

EXAMPLE 105

3-[4-(3,5-Dichloropyrid-4-ylcarboxamido)phenyl]-2-(3-benzoylbenzeneamino)propanoic acid The title compound was prepared by lithium hydroxide hydrolysis of the compound of Example 87: $\delta$H (DMSO d$_6$) 10.84 (1H, s), 8.77 (2H, s), 7.90–7.40 (6H, m), 7.35–7.10 (3H, m), 7.05–6.80 (3H, m), 6.30 (1H, m), 4.14 (1H, br. m), 3.20–2.80 (2H, m): m/z (EI$^+$, 70V) 534.

EXAMPLE 106

3-[4-((3,5-Dichloropyrid-4-ylcarboxamido)phenyl]-2-3-carboxybenzeneamino)propanoic acid The title compound was prepared by lithium hydroxide hydrolysis of the compound of Example 88: $\delta$H (DMSO d$_6$) 12.61 (1H, br. s), 10.84 (1H, s), 8.77 (2H, s), 7.54 (2H, d, J 8.5 Hz), 7.30 (2H, d, J 8.5 Hz), 7.13 (3H, m), 6.78 (1H, m), 6.20 (1H, b r. m), 4.12 (1H, br. m), 3.20–2.90 (2H, m): m/z (EI$^+$, 70V) 474.

EXAMPLE 107

3-[4-(3,5-Dichloropyrid-4-ylcarboxamido)phenyl]-2-(5-chloro-4-propylthiopyridine-2-amino)propanoic acid The title compound was prepared by lithium hydroxide hydrolysis of the compound of Example 89: $\delta$H (DMSO d$_6$) 10.83 (1H, s), 8.77 (2H, s), 7.81 (1H, s), 7.53 (2H, d, J 8.4 Hz), 7.23 (2H, d, J 8.4 Hz), 6.54 (1H, s), 4.56 (1H, m), 3.20–2.80 (4H, m), 1.63 (2H, m), 0.99 (3H, t, J 7.3 Hz): m/z (EI$^+$, 70V) 540.

EXAMPLE 108

3-[4-(3,5-Dichloropyrid-4-ylcarboxamido)phenyl]-2-(5-chloro-4-propylsulphinylpyridine-2-amino)propanoic acid The title compound was prepared by lithium hydroxide hydrolysis of the compound of Example 90: $\delta$H (DMSO d$_6$) 12.48 (1H, br. s), 10.72 (1H, s), 8.65 (1H, s), 7.86 (1H, s), 7.70–7.40 (3H, m), 7.20 (2H, m), 6.88 (1H, m), 4.40 (1H, br. m), 3.10–2.90 (2H, m), 2.90–2.50 (2H, m), 1.80–1.30 (2H, m), 0.85 (3H, m): m/z (EI$^+$, 70V) 555.

EXAMPLE 109

3-[4-(3,5-Dichloropyrid-4-ylcarboxamido)phenyl]-2-(5-chloro-4-propylsulphonylpyridine-2-amino)propanoic acid The title compound was prepared by lithium hydroxide hydrolysis of the compound of Example 91: $\delta$H (DMSO d$_6$) 10.84 (1H, s), 8.77 (2H, s), 8.18 (1H, s), 7.80 (1H, br. m), 7.53 (2H, d, J 8.5 Hz), 7.26 (3H, m), 4.60 (1H, m), 3.41 (2H, m), 3.30–3.10 (1H, m), 3.10–2.80 (1H, m), 1.50 (2H, m), 0.91 (3H, t, J 7.5 Hz): m/z (EI$^+$, 70V) 571.

EXAMPLE 110

3-[4-(3,5-Dichloropyrid-4-ylcarboxamido)phenyl]-2-(5-chloropyridine-2-amino)propanoic acid The title compound was prepared by lithium hydroxide hydrolysis of the compound of Example 92: $\delta$H (DMSO d$_6$) 12.40 (1H, br. s), 10.71 (1H, s), 8.68 (2H, s), 7.79 (1H, s), 7.40 (2H, d, J 8.4 Hz), 7.28 (1H, m), 7.12 (2H, d, J 8.4 Hz), 6.91 (1H, d, J 8.2 Hz), 6.47 (1H, d, J 8.9 Hz), 4.45 (1H, m), 2.95 (1H, m), 2.77 (1H, m): m/z (EI$^+$, 70V) 465.

EXAMPLE 111

3-[4-(3,5-Dichloropyrid-4-ylcarboxamido)phenyl]-2-(4-propylsulphonylpyridine-2-amino)propanoic acid The title compound was prepared by lithium hydroxide hydrolysis of the compound of Example 94: $\delta$H (DMSO d$^6$) 10.86 (1H, s), 8.78 (2H, s), 8.19 (1H, d, J 5.3 Hz), 7.55 (3H, m) 7.28 (2H, d, J 8.5 Hz), 7.07 (1H, s), 6.88 (1H, m), 4.64 (1H, br. m), 3.27 (2H, t, J 7.7 Hz), 3.12 (1H, m), 2.92 (1H, m), 1.50 (2H, m), 0.91 (3H, t, J 7.4 Hz): m/z (EI$^+$, 70V) 537.

EXAMPLE 112

3-[4-(3,5-Dichloropyrid-4-ylcarboxamido)phenyl]-2-(5-carboxy-4-propylsulphonylpyridine-2-amino)propanoic acid The title compound was prepared by lithium hydroxide hydrolysis of the compound of Example 96: δH (DMSO $d_6$) 13.0 (1H, br. s), 10.85 (1H, s), 8.78 (2H, s), 8.48 (1H, s), 7.55 (2H, d, J 8.6 Hz), 7.26 (3H, m), 4.70 (1H, br, m), 3.66 (2H, t, J 7.7 Hz), 3.40–2.90 (2H, m), 1.58 (2H, m), 0.94 (3H, t, J 7.4 Hz): m/z (EI$^+$, 70V) 581.

EXAMPLE 113

S-3-[4-(3,5-Dichloropyrid-4-ylcarboxamido)phenyl]-2-(5-carboxy-4-trifluormethylpyrimidin-2-ylamino)propanoic acid The title compound was prepared from Intermediate 3 and methyl 2-chloro-4-(trifluoromethyl)pyrimidine 5-carboxylate, followed by hydrolysis: δH (DMSO $d_6$) 10.80 (1H, br s), 8.77 (1H, s), 8.75 (2H, s), 8.51 and 8.38 (together 1H, d, J 8.0 Hz), 7.53 (2H, d, J 8.0 Hz), 7.32 (2H, d, J 8.0 Hz), 4.65–4.50 (1H, br m), 3.21 (1H, dd, J 13.9, 3.9 Hz) and 3.03 (1H, dd, J 13.9, 10.4 Hz); m/z (EI$^+$, 60V) 545.

EXAMPLE 114

S-ethyl-3-[4-(3,5-dichloro-1-oxido-4-pyridiniocarboxamidophenyl]-2-(6-propylsulphonylpyrimidin-4-yl)propanoate and S-ethyl-3-[4-(3,5-dichloro-1-oxido-4-pyridiniocarboxamidophenyl]-2-(6-propylsulphonyl-1-oxido-4-pyrimidinium)propanoate A solution of the compound of Example 6 (14.0 g, 25.2 mmol) and mCPBA (30 g, 105 mmol assuming 60% pure) in dichloromethane (300 ml) were stirred at room temperature for δH. The mixture was then treated with 10% aqueous sodium sulfite solution (200 ml) and stirred for 5 mins. A further 200 ml of DCM was added before washing consecutively with saturated aqueous NaHCO$_3$ (200 ml), brine (200 ml) and water (200 ml) dried (MgSO$_4$) and evaporated in vacuo. The yellow solid obtained was chromatographed (silica; ethyl acetate→ethyl acetate/methanol (10%)) to afford S-ethyl-3-[4-(3,5-dichloro-1-oxido-4-pyridiniocarboxamido) phenyl]-2-(6-propylsulphonylpyrimidin-4-yl)propanoate (3.0 g) and S-ethyl-3-[4-3,5-dichloro-1-oxido-4-pyridiniocarboxamidophenyl]-2-(6-propylsulphonyl-1-oxido-4-pyrimidinio)propanoate (5.5 g). These materials were used without further characterisation in Examples 115 and 116.

EXAMPLE 115

S-3-[4-(3,5-Dichloro-1-oxido-4-pyridiniocarboxamido)phenyl]-2-(6-propylsulphonylpyrimidin-4-ylamino)propanoic acid A solution of the mono-N-oxide from Example 114 (3.0 g, 5.2 mmol) and lithium hydroxide monohydrate (0.32 g, 7.74 mmol) in THF/H$_2$O (1:1, 100 ml) was stirred overnight at room temperature. THF was removed by evaporation in vacuo, and water (1000 ml) added. The reaction mixture as made pH3 with hydrochloric acid (1M) and then filtered and precipitate collected and dried. Purification by recrystallisation (acetonitrile/H$_2$O) gave the title compound as a white powder (500 mg, 17%). δH (DMSO $d_6$) 10.83 (1H, s), 8.72 (2H, s), 8.57 (1H, s), 8.45 (1H, d, J 7.7 Hz), 7.55 (2H, d, J 8.5 Hz), 7.27 (2H, d, J 8.5 Hz), 7.22 (1H, s), 4.78 (1H, dt, J 8.6, 5.0 Hz), 3.2 (m, obscured by H$_2$O), 3.00 (2H, dd, J 13.9, 9.11 Hz), 1.59 (2H, q, J 7.6 Hz), 0.94 (3H, t, J 7.4 Hz); m/z (EI$^+$, 80V) 554.

EXAMPLE 116

S-3-[4-(3,5-Dichloro-1-oxido-4-pyridiniocarboxamido)phenyl]2-6-propylsulphonyl-1-oxido-4-pyrimidinioamino)propanoic acid A solution of the di-N-oxide from Example 114 (5.5 g, 9.2 mmol) and lithium hydroxide monohydrate (0.6 g, 13.8 mmol) in THF/H$_2$O 1:1 (100 ml) was stirred overnight at room temperature. The THF was then removed in vacuo and the remaining solution diluted with H$_2$O (100 ml), before 1 M HCl added to make the pH3. The precipitate was collected by filtration, dried to give the title compound as a pale yellow solid (40 g, 76%). δH (DMSO $d_6$) 10.83 (1H, s), 8.72 (2H, s), 8.57 (1H, s), 8.45 (1H, d, J 7.7 Hz), 7.55 (2H, d, J 8.5 Hz), 7.27 (2H, d, J 8.5 Hz), 7.22 (1H, s), 4.78 (1H, m), 3.2 (m, obscured by H$_2$O), 1.60 (2H, q, J 7.6 Hz), 0.93 (3H, t, J 7.4 Hz); m/z (EI$^+$, 80V) 572.

EXAMPLE 117

3-[4-(3,5-Dichloropyrid-4-ylcarboxamido)phenyl]-2-(6-propylpyrid-2-ylamino)propanoic acid A mixture of Intermediate 25 (150 mg), dirhodiumtetraacetate, (1.8 mg, 5.1 μmols) and 2-amino-6-propylpyridine in anydrous toluene (2.5 mL) was agitated at ambient temperature for 0.5 h then at 80° C. for 6 h. The resin was filtered and then washed with DCM, DMF, methanol, water, methanol, DMF and DCM. The resin was treated with 50% trifluoroacetic acid in DCM (4.0 ml) for 3 h with agitation and filtered. The resin was then washed with a 4.0 ml portion of DCM. The combined filtrate was evaporated in vacuo to give the crude product (48 mg) which was purified by preparative HPLC to afford the title compound (2.7 mg). HPLC-MS Retention time 2.19 min; MH$^+$473.

HPLC-MS

HPLC-MS was performed on a Hewlett Packard 1100/MSD ES Single Quadropole system with diode array detector using a Luna C18(2) 50×2.0 mm (3 μm) column, running a gradient of 95% [0.1% aqueous formic acid], 5% [0.1% formic acid in acetonitrile] to 10% [0.1% aqueous formic acid], 90% [0.1% formic acid in acetonitrile] over 2 min, then maintaining the mobile phase at that ratio for a further 1 min. Flow rate 0.8 ml/min. MS was acquired by API electrospray in positive ion mode, at 70V, scanning from 150 to 750 amu.

The following compounds of Examples 118–168 were prepared in a similar manner to the compound of Example 117, each using the starting material shown in place of 2-amino-6-propylpyridine.

EXAMPLE 118

3-[4-(3,5-Dichloropyrid-4-ylcarboxamido)phenyl]-2-(3-methylisoxazo)-5-ylamino)propanoic acid 5-Amino-3-methylisoxazole gave the title compound (0.7 mg) HPLC-MS Retention time 2.37 min; MH$^+$ 435.

EXAMPLE 119

3-[4-(3,5-Dichloropyrid-4-ylcarboxamido)phenyl]-2-[2-acetyl-5-(4-chlorolohenyl)thien-3-ylamino]propanoic acid 2-Acetyl-3-amino-5-(4-chlorophenyl)thiophene gave the title compound (2.6 mg) HPLC-MS Retention time 2.90 min; MH$^+$ 588

EXAMPLE 120

3-[4-(3,5-Dichloropyrid-4-ylcarboxamido)phenyl]-2-(2-methylquinol-6-ylamino)propanoic acid 6-Amino-2-methylquinoline gave the title compound (5.0 mg) HPLC-MS Retention time 2.17 min; MH$^+$ 495.

EXAMPLE 121

3-[4-(3,5-Dichloropyrid-4-ylcarboxamido phenyl]-2-(quinol-6-ylamino)propanoic acid 6-Aminoquinoline gave the title compound (3.3 mg) HPLC-MS Retention time 2.15 min; MH$^+$ 481

EXAMPLE 122

3-[4-(3,5-Dichloropyrid-4-ylcarboxamido)phenyl]-2-(quinol-2-ylamino)propanoic acid 2-Aminoquinoline gave the title compound (4.3 mg) HPLC-MS Retention time 2.20 min; MH$^+$ 481.

EXAMPLE 123

3-[4-(3,5-Dichloropyrid-4-ylcarboxamido)phenyl]-2-(quinol-3-ylamino)propanoic acid 3-Aminoquinoline gave the title compound (5.1 mg) HPLC-MS Retention time 2.22 min; MH$^+$ 481.

EXAMPLE 124

3-[4-(3,5-Dichloropyrid-4-ylcarboxamido)phenyl]-2-[4-chloro-2-(methylthio)pyrimidin-6-yl amino]propanoic acid 6-Amino-4-chloro-2-(methylthio)pyrimidine gave the title compound (1.4 mg) HPLC-MS Retention time 2.63 min; MH$^+$ 512.

EXAMPLE 125

3-[4-(3,5-Dichloropyrid-4-ylcarboxamido)phenyl]-2-(3,5-dichloro-2,6-difluoropyrid-4-ylamino)propanoic acid 4-Amino-3,5-dichloro-2,6-difluoropyridine gave the title compound (1.1 mg) HPLC-MS Retention time 2.81 min; MH$^+$ 535.

EXAMPLE 126

3-[4-(3,5-Dichloropyrid-4-ylarboxamido)phenyl]-2-(4,6-dimethylpyrid-2-ylamino)propanoic acid 2-Amino-4,6-dimethylpyridine gave the title compound (3.9 mg) HPLC-MS Retention time 2.11 min; MH$^+$ 459.

EXAMPLE 127

3-[4-(3,5-Dichloropyrid-4-ylcarboxamido)phenyl]-2-(4,6-dimethoxypyrimidin-2-ylamino)propanoic acid 2-Amino-4,6-dimethoxypyrimidine gave the title compound (3.0 mg) HPLC-MS Retention time 2.56 min; MH$^+$ 492.

EXAMPLE 128

3-[4-(3,5-Dichlorolpyrid-4-ylcarboxamido)phenyl]-2-(2-methylpyrid-4-ylamino)propanoic acid 4-Amino-2-methylpyridine gave the title compound (1.3 mg) HPLC-MS Retention time 2.09 min; MH$^+$ 445.

EXAMPLE 129

3-[4-(3,5-Dichlopyrid-4-ylcarboxamido)phenyl]-2-(6-chloropyrid-3-ylamino)propanoic acid 3-Amino-6-chloropyridine gave the title compound (2.7 mg) HPLC-MS Retention time 2.52 min; MH$^+$ 465.

EXAMPLE 130

3-[4-(3,5-Dichloropyrid-4-ylcarboxamido)phenyl]-2-(5-bromopyrid-2-ylamino)propanoic acid 2-Amino-5-bromo-2-pyridine gave the title compound (2.6 mg) HPLC-MS Retention time 2.60 min; MH$^+$ 510.

EXAMPLE 131

3-[4-(3,5-Dichloropyrid-4-ylcarboxamido)phenyl]-2-(2,6-dichloropyrid-4-ylamino)propanoic acid 4-Amino-2,6-dichloropyridine gave the title compound (1.6 mg) HPLC-MS Retention time 2.62 min; MH$^+$ 499

EXAMPLE 132

3-[4-(3,5-Dichloropyrid-4-ylcarboxamido)phenyl]-2-(3,5-dibromopyrid-2-ylamino)propanoic acid 2-Amino-3,5-dibromopyridine gave the title compound (0.2 mg) HPLC-MS Retention time 2.83 min; MH$^+$ 589.

EXAMPLE 133

3-[4-(3,5-Dichloropyrid-4-ylcarboxamido)phenyl]-2-(4,6-dimethylpyrimidin-2-ylamino)propanoic acid 2-Amino-4,6-dimethylpyrimidine gave the title compound (2.7 mg) HPLC-MS Retention time 2.23 min; MH$^+$ 460.

EXAMPLE 134

3-[4-(3,5-Dichloropyrid-4-ylcarboxamido)phenyl]-2-(3-ethyl-6-methylpyrid-2-ylamino)propanoic acid 2-Amino-3-ethyl-6-methylpyridine gave the title compound (1.3 mg) HPLC-MS Retention time 2.23 min; MH$^+$ 473.

EXAMPLE 135

3-[4-(3,5-Dichloropyrid-4-ylcarboxamido)phenyl]-2-(4-ethylpyrid-2-ylamino)propanoic acid 2-Amino-4-ethylpyridine gave the title compound (0.8 mg) HPLC-MS Retention time 2.14 min; MH$^+$ 459.

EXAMPLE 136

3-[4-(3,5-Dichloropyrid-4-ylcarboxamido)phenyl]-2-(6-ethylpyrid-2-ylamino)propanoic acid 2-Amino-6-ethylpyridine gave the title compound (2.4 mg) HPLC-MS Retention time 2.14 min; MH$^+$ 459.

EXAMPLE 137

3-[4-(3,5-Dichloropyrid-4ylcarboxamido)phenyl]-2-(2,5-dichloropyrid-3-ylamino)propanoic acid 3-Amino-2,5-dichloropyridine gave the title compound (1.0 mg) HPLC-MS Retention time 2.68 min; MH$^+$ 501.

EXAMPLE 138

3-[4-(3,5-Dichloropyrid-4-ylcarboxamido)phenyl]-2-(4-trifluoromethypyrimidin-2-ylamino)propanoic acid 2-Amino-4-trifluoromethylpyrimidine gave the title compound (1.2 mg) HPLC-MS Retention time 2.62 min; MH$^+$ 500.

EXAMPLE 139

3-[4-(3,5-Dichloropyrid-4-ylcarboxamido)phenyl]-2-(5-bromopyrimidin-2-ylamino)propanoic acid 2-Amino-5-bromopyrimidine gave the title compound (0.6 mg) HPLC-MS Retention time 2.56 min; MH$^+$ 511.

EXAMPLE 140

3-[4-(3,5-Dichloropyrid-4-ylcarboxamido)phenyl]-2-(2-chloropyrid-3-ylamino)propanoic acid 3-Amino-2-chloropyridine gave the title compound (2.5 mg) HPLC-MS Retention time 2.52 min; MH$^+$ 465.

EXAMPLE 141

3-[4-(3,5-Dichloropyrid-4-ylcarboxamido)phenyl]-2-[4-trifluoromethyl-6-methylpyrimidin-2-ylamino)propanoic acid 2-Amino-4-trifluoromethyl-6-methylpyrimidine gave the title compound (3.1 mg) HPLC-MS Retention time 2.65 min; MW$^+$ 514.

EXAMPLE 142

3-[4-(3,5-Dichloropyrid-4-ylcarboxamido)phenyl]-2-(4,6-dichloro-2-methylpyrimidin-5-ylamino)propanoic acid 5-Amino-4,6-dichloro-2-methylpyrimidine gave the title compound (1.7 mg) HPLC-MS Retention time 2.55 min; MH$^+$ 516.

EXAMPLE 143

3-[4-(3,5-Dichloropyrid-4-ylcarboxamido)phenyl]-2-(4,6-dimethoxypyrimidin-5-ylamino)propanoic acid 5-Amino-4,6-Dimethoxypyrimidine gave the title compound (0.9 mg) HPLC-MS Retention time 2.43 min; MH$^+$ 492.

EXAMPLE 144

3-[4-(3,5-Dichloropyrid-4-ylcarboxamido)phenyl]-2-(3-benzyloxypyrid-2-ylamino)propanoic acid 2-Amino-3-benzyloxypyridine gave the title compound (2.8 mg) HPLC-MS Retention time 2.33 min; MH$^+$ 537.

EXAMPLE 145

3-[4-(3,5-Dichloropyrid-4-ylcarboxamido)phenyl]-2-[4-(5-chloropyrid-2-yloxy)phenylamino]propanoic acid 4-(5-Chloropyrid-2-yloxy)aniline gave the title compound (1.7 mg) HPLC-MS Retention time 2.73 min; MH$^+$ 557.

EXAMPLE 146

3-[4-(3,5-Dichloropyrid-4-ylcarboxamido)phenyl]-2-(2-chloro-5-phenylpyrid-6-ylamino)propanoic acid 6-Amino-2-chloro-5-phenylpyridine gave the title compound (0.5 mg) HPLC-MS Retention time 2.87 min MH$^+$ 541

EXAMPLE 147

3-[4-(3,5-Dichloropyrid-4-ylcarboxamido)phenyl]-2-(1-oxidopyrid-3-ylamino)propanoic acid 3-Aminopyridine-1-oxide gave the title compound (1.1 mg) HPLC-MS Retention time 2.16 min; MH$^+$ 447.

EXAMPLE 148

3-[4-3,5-Dichloropyrid-4-ylcarboxamido)phenyl]-2-[4-(4-methylphenyl)pyrimidin-2-ylamino]propanoic acid 2-Amino-4-(4-methylphenyl)pyrimidine gave the title compound (2.2 mg) HPLC-MS Retention time 2.57 min; MH$^+$ 522.

EXAMPLE 149

3-[4-(3,5-Dichloropyrid-4-ylcarboxamido)phenyl]-2-[4-(4-chlorophenyl)pyrimidin-2-ylamino]propanoic acid 2-Amino-4-(4-chlorophenyl)pyrimidine gave the title compound (0.8 mg) HPLC-MS Retention time 2.67 min; MW$^+$ 542.

EXAMPLE 150

3-[4-(3,5-Dichloropyrid-4-ylcarboxamido)phenyl-2-(4-chloro-6-pyrrolidinopyrimidin-2-ylamino)propanoic acid 2-Amino-4-chloro-6-pyrrolidinopyrimidine gave the title compound (3.2 mg) HPLC-MS Retention time 2.59 min; MH$^+$ 537.

EXAMPLE 151

3-[4-(3,5-Dichloropyrid-4-ylcarboxamido)phenyl]-2-(4-(chlorodifluoromethyl)-6-methyl pyrimidin-2-ylamino)propanoic acid 2-Amino-4-(chlorodifluoromethyl)-6-methylpyrimidine gave the title compound (0.6 mg) HPLC-MS Retention time 2.66 min; MH$^+$ 532.

EXAMPLE 152

3-[4-(3,5-Dichloropyrid-4-ylcarboxamido)phenyl]-2-(3,5-difluorophenylamino)propanoic acid 3,5-Difluoroaniline gave the title compound (1 mg) HPLC-MS Retention 2.67 min; MH$^+$ 466.

EXAMPLE 153

3-[4-(3,5-Dichloropyrid-4-ylcarboxamido)phenyl]-2-(2,4,6-trimethylphenylamino)propanoic acid 2,4,6-Trimethylaniline gave the title compound (4 mg) HPLC-MS Retention 2.77 min; MH$^+$ 472.

EXAMPLE 154

3-[4-(3,5-Dichloropyrid-4-ylcarboxamido)phenyl]-2-(2,6-diethylphenylamino)propanoic acid 2,6-Diethylaniline gave the title compound (6 mg) HPLC-MS Retention 2.85 min; MH$^+$ 486

EXAMPLE 155

3-[4-(3,5-Dichloropyrid-4-ylcarboxamido)phenyl]-2-(3-(trifluoromethyl)phenylamino)propanoic acid 3-(Trifluoromethyl)aniline gave the title compound (3 mg) HPLC-MS Retention 2.74 min; MH$^+$ 498.

EXAMPLE 156

3-[4-(3,5-Dichloropyrid-4-ylcarboxamido)phenyl]-2-(2-propylphenylamino)propanoic acid 2-Propylaniline gave the title compound (2 mg) HPLC-MS Retention 2.80 min; MH$^+$ 472.

EXAMPLE 157

3-[4-(3,5-Dichloropyrid-4-ylcarboxamido)phenyl]-2-(4-ethylphenylamino)propanoic acid 4-Ethylaniline gave the title compound (2 mg) HPLC-MS Retention 2.72 min; MH$^+$ 458.

EXAMPLE 158

3-[4-(3,5-Dichloropyrid-4-ylcarboxamido)phenyl]-2-(3,4,5-trichlorophenylamino)propanoic acid 3,4,5-Trichloroaniline gave the title compound (1 mg) HPLC-MS Retention 2.86 min; MH$^+$ 532.

EXAMPLE 159

3-[4-(3,5-Dichloropyrid-4-ylcarboxamido)phenyl]-2-(3,4,5-trifluorophenylamino)propanoic acid 3,4,5-Trifluoroaniline gave the title compound (3 mg) HPLC-MS Retention 2.70 min; MH$^+$ 484

EXAMPLE 160

3-[4-(3,5-Dichloropyrid-4-ylcarboxamido)phenyl]-2-(2-benzylphenylamino)propanoic acid 2-Benzylaniline gave the title compound (1 mg) HPLC-MS Retention 2.84 min; MH$^+$ 520

EXAMPLE 161

3-[4-(3,5-Dichloropyrid-4-ylcarboxamido)phenyl]-2-(3,5-bis(trifluoromethyl)phenylamino)propanoic acid 3,5-Bis(trifluoromethyl)aniline gave the title compound (1 mg) HPLC-MS Retention 2.87 min; MH$^+$ 566.

EXAMPLE 162

3-[4-(3,5-Dichloropyrid-4-ylcarboxamido)phenyl]-2-(4-isopropylphenylamino)propanoic acid 4-Isopropylaniline gave the title compound (2 mg) HPLC-MS Retention 2.80 min; MH$^+$ 472.

EXAMPLE 163

3-[4-(3,5-Dichloropyrid-4-ylcarboxamido)phenyl]-2-(3-trifluoromethoxyphenylamino)propanoic acid 3-Trifluoromethoxyaniline gave the title compound (4 mg) HPLC-MS Retention 2.76 min; MH$^+$ 514.

EXAMPLE 164

3-[4-(3,5-Dichloropyrid-4-ylcarboxamido)phenyl]-2-(2-fluoro-5-(trifluoromethyl)phenylamino)propanoic acid 2-Fluoro-5-(trifluoromethyl)aniline gave the title compound (4 mg) HPLC-MS Retention 2.75 min; MH$^+$ 516.

EXAMPLE 165

3-[4-(3,5-Dichloropyrid-4-ylcarboxamido)phenyl]-2-(3-chloro-4-fluorophenylamino)propanoic acid 3-Chloro-4-fluoroaniline gave the title compound (6 mg) HPLC-MS Retention 2.70 min; MH$^+$ 482.

EXAMPLE 166

3-[4-(3,5-Dichloropyrid-4-ylcarboxamido)phenyl]-2-(3-nitrophenylamino)propanoic acid 3-Nitroaniline gave the title-compound (2 mg) HPLC-MS 2.62 min; MH$^+$ 475.

EXAMPLE 167

3-[4-(3,5-Dichloropyrid-4-ylcarboxamido)phenyl]-2-(2,3,5,6-tetrafluorophenylamino)propanoic acid 2,3,5,6-tetrafluoroaniline gave the title compound (1 mg) HPLC-MS Retention 2.72 min; MH$^+$ 502.

EXAMPLE 168

3-[4-(3,5-Dichloropyrid-4-ylcarboxamido)phenyl]-2-(3-chlorophenylamino)propanoic acid 3-Chloroaniline gave the title compound (1 mg) HPLC-MS Retention 2.70 min; MH$^+$ 464.

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-Iq 96 well NUNC plates were coated with F(ab)$_2$ fragment goat anti-human IgG Fc$\gamma$-specific antibody [Jackson Immuno Research 109-006-098: 100 µl at 2 µg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 µl containing 2.5×10$^5$ Jurkat cells in the presence or absence of titrated test compounds.

Each plate was washed (2×) with medium and the adherent cells were fixed with 100 µl methanol for 10 minutes followed by another wash. 100 µl 0.25% Rose Bengal (Sigma R4507) in PBS was added for 5 minutes at room temperature and the plates washed (3×) in PBS. 100 µl 50% (v/v) ethanol in PBS was added and the plates left for 60 min after which the absorbance (570 nm) was measured.

$\alpha_4\beta_7$ Integrin-dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a sub-line of the β-lymphoblastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 µg/ml in phosphate-buffered saline (PBS) for 2 hr at 37° C. The plates were washed (3× in PBS) and then blocked for 1 h in 100 µl PBS/1% BSA at room temperature on a rocking platform. The blocked plates were washed (3× in PBS) and the assay then performed at 37° C. in a total volume of 200 µl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 µl in the presence of 10 ng/ml phorbol-12-myristate-13-acetate, and in the presence or absence of test compounds, and incubated for 20 min at 37° C. followed by 30 min at room temperature. The plates were washed in medium and 100 µl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 µg/ml TMB (Boehringer Mannheim) in 0.1M sodium acetate/citrate buffer, pH 6.0 and absorbance measured at 630 nm.

$\alpha$IIb/$\beta_3$-dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$. 2H$_2$O 0.065). Aggregation was monitored following addition of 2.5 µM ADP (Sigma) in the presence or absence of inhibitors.

In the above assays the preferred compounds of the invention generally have IC$_{50}$ values in the $\alpha_4\beta_1$ and $\alpha_4\beta_7$ assays of 1 µM and below. In the other assays featuring α integrins of other subgroups the same compounds had IC$_{50}$ values of 50 µM and above thus demonstrating the potency and selectivity of their action against $\alpha_4$ integrins.

What is claimed is:

1. A compound of formula I:

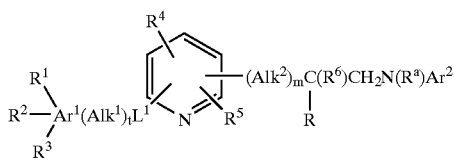

wherein
Ar$^1$ is an aromatic or heteroaromatic group;
each of R$^1$, R$^2$, R$^3$, R$^4$ and R$^5$ are independently selected from the formula:

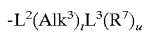

in which L$^2$ and L$^3$ which may be the same or different in each occurrence are selected from the group consisting of a covalent bond or a linker atom or group,
t is zero or 1,
u is 1, 2 or 3,
Alk$^3$ is an aliphatic or heteroaliphatic chain, and
R$^7$ is a hydrogen or halogen atom or a group selected from alkyl, —OR$^8$, where R$^8$ is a hydrogen atom or an optionally substituted alkyl group, —SR$^8$, —NR$^8$R$^9$, where R$^9$ is as defined for R$^8$ and may be the same or different, —NO$_2$, —CN, —CO$_2$R$^8$, —SO$_3$H, —SOR$^8$, —SO$_2$R$^8$, —OCO$_2$R$^8$, —CONR$^8$R$^9$, —OCONR$^8$R$^9$, —CSNR$^8$R$^9$, —COR$^8$, —OCOR$^8$, —N(R$^8$)COR$^9$, —N(R$^8$)CSR$^9$, —SO$_2$N(R$^8$)(R$^9$), —N(R$^8$)SO$_2$R$^9$, —N(R$^8$)CON(R$^9$)(R$^{10}$), where R$^{10}$ is a hydrogen atom or an optionally substituted alkyl group, —N(R$^8$)CSN(R$^9$)(R$^{10}$) or —N(R$^8$)SO$_2$N(R$^9$)(R$^{10}$);
Alk$^1$ is an optionally substituted aliphatic or heteroaliphatic chain;
L$^1$ is a covalent bond or a linker atom or group;
Alk$^2$ is a straight or branched alkylene chain;
m is zero or 1;
R$^6$ is a hydrogen atom or a methyl group;
r is zero or 1;
R is a carboxylic acid group;
R$^a$ is a hydrogen atom or a methyl group; and
Ar$^2$ is an optionally substituted aromatic or heteroaromatic group;
or a pharmaceutically acceptable salt thereof.

2. A compound of formula II:

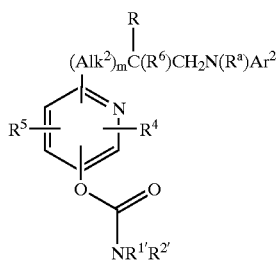

wherein
R is a carboxylic acid group;
R$^a$ is a hydrogen atom or a methyl group;

R$^4$ and R$^5$ are independently selected from the formula:

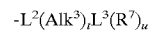

in which L$^2$ and L$^3$ which may be the same or different is each occurrence are selected from the group consisting of a covalent bond or a linker atom or group,
t is zero or 1,
u is 1, 2 or 3,
Alk$^3$ is an aliphatic or heteroaliphatic chain, and
R$^7$ is a hydrogen or halogen atom or a group selected from alkyl, —OR$^8$, where R$^8$ is a hydrogen atom or an optionally substituted alkyl group, —SR$^8$, —NR$^8$R$^9$, where R$^9$ is as defined for R$^8$ and may be the same or different, —NO$_2$, —CN, —CO$_2$R$^8$, —SO$_3$H, —SOR$^8$, —SO$_2$R$^8$, —OCO$_2$R$^8$, —CONR$^8$R$^9$, —OCONR$^8$R$^9$, —CSNR$^8$R$^9$, —COR$^8$, —OCOR$^8$, —N(R$^8$)COR$^9$, —N(R$^8$)CSR$^9$, —SO$_2$N(R$^8$)(R$^9$), —N(R$^8$)SO$_2$R$^9$, —N(R$^8$)CON(R$^9$)(R$^{10}$), where R$^{10}$ is a hydrogen atom or an optionally substituted alkyl group, —N(R$^8$)CSN(R$^9$)(R$^{10}$) or —N(R$^8$)SO$_2$N(R$^9$)(R$^{10}$);
R$^6$ is a hydrogen atom or a methyl group;
R$^{1'}$ and R$^{2'}$ are independently selected from the group consisting of hydrogen, alkyl, substituted alkyl, alkenyl, substituted alkenyl, aryl, cycloalkyl, substituted cycloalkyl, heterocyclic, heteroaryl or R$^{1'}$ and R$^{2'}$, together with the nitrogen atom to which they are attached, are joined to form an optionally substituted heterocyclic ring;
Alk$^2$ is a straight or branched alkylene chain;
m is zero or 1;
Ar$^2$ is an optionally substituted aromatic or heteroaromatic group;
or a pharmaceutically acceptable salt thereof.

3. The compound according to claim 2, wherein R$^{1'}$ and R$^{2'}$ are independently selected from the group consisting of hydrogen, alkyl, substituted alkyl, alkenyl, substituted alkenyl, cycloalkyl, substituted cycloalkyl, or R$^{1'}$ and R$^{2'}$, together with the nitrogen atom to which they are attached, are joined to form an optionally substitute heterocyclic ring provided that said substituted alkyl, substituted alkenyl and substituted cycloalkyl do not carry an aryl, substituted aryl, heteroaryl or substituted heteroaryl group.

4. A compound of formula I:

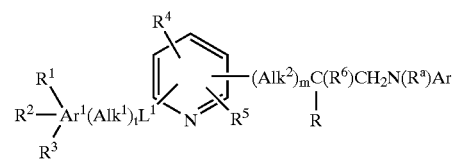

wherein
Ar$^1$ is an aromatic or heteroaromatic group;
each of R$^1$, R$^2$, R$^3$, R$^4$ and R$^5$ are independently selected from the formula:

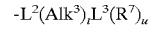

in which L$^2$ and L$^3$ which may be the same or different in each occurrence are selected from the group consisting of a covalent bond or a linker atom or group,
t is zero or 1,
u is 1, 2 or 3,
Alk$^3$ is an aliphatic or heteroaliphatic chain, and
R$^7$ is a hydrogen or halogen atom or a group selected from alkyl, —OR$^8$, where R$^8$ is a hydrogen atom or an optionally substituted alkyl group, —SR$^8$, —NR$^8$R$^9$, where R$^9$ is as defined for R$^8$ and may be the same or different, —NO$_2$, —CN, —CO$_2$R$^8$, —SO$_3$H, —SOR$^8$, —SO$_2$R$^8$, —OCO$_2$R$^8$, —CONR$^8$R$^9$, —OCONR$^8$R$^9$, —CSNR$^8$R$^9$, —COR$^8$, —OCOR$^8$, —N(R$^8$)COR$^9$, —N(R$^8$)CSR$^9$, —SO$_2$N(R$^8$)(R$^9$), —N(R$^8$)SO$_2$R$^9$, —N(R$^8$)CON(R$^9$)(R$^{10}$), where R$^{10}$ is a hydrogen atom or an optionally substituted alkyl group, —N(R$^8$)CSN(R$^9$)(R$^{10}$) or —N(R$^8$)SO$_2$N(R$^9$)(R$^{10}$);

Alk$^1$ is an optionally substituted aliphatic or heteroaliphatic chain;
L$^1$ is a covalent bond or a linker atom or group;
Alk$^2$ is a straight or branched alkylene chain;
m is zero or 1;
R$^6$ is a hydrogen atom or a methyl group;
r is zero or 1;
R is a carboxylic acid group;
R$^a$ is a hydrogen atom or a methyl group; and
Ar$^2$ is selected from group consisting of moieties of formula IIIa, IIIc, IIId, IIIe and IIIf:

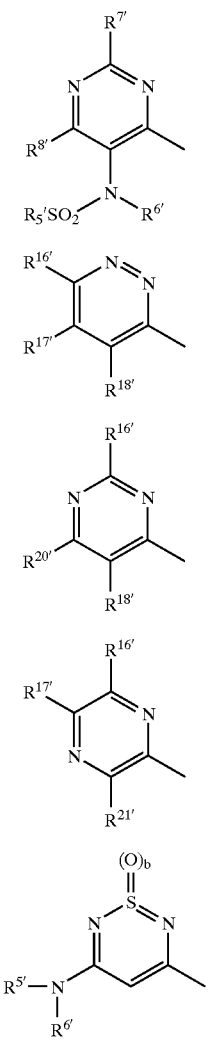

where R$^{5'}$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocyclic, heteroaryl and substituted heteroaryl;

R$^{6'}$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —SO$_2$R$^{10'}$ where R$^{10'}$ is selected from the group consisting of alkyl, substituted alkyl, cycloalkyl, cycloalkenyl, substituted cycloalkenyl, heterocyclic, substituted heterocyclic, aryl, substituted aryl, heteroaryl, substituted heteroaryl;

R$^{7'}$ and R$^{8'}$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

R$^{16'}$ and R$^{17'}$ are independently selected form the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen;

R$^{18'}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

R$^{20'}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

R$^{21'}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic; and b is 1 or 2;
or a pharmaceutically acceptable salt thereof.

5. A pharmaceutical composition comprising a pharmaceutically acceptable excipient and an effective amount of a compound according to any of claims 1–4.

6. A method for binding VLA-4 in a biological sample which method comprises contacting the biological sample with a compound according to any of claim 1–4 under conditions wherein said compound binds to VLA-4.

7. A method for treating an inflammatory condition mediated by VLA-4 in a mammalian patient, which method comprises administering to said patient a therapeutically effective amount of a pharmaceutical composition of claim 5, wherein said inflammatory condition is selected from the group consisting of inflammatory arthritis, multiple sclerosis, allograft rejection, diabetes, inflammatory dermatoses, asthma and inflammatory bowel disease.

8. The method according to claim 7, wherein said inflammatory condition is asthma.

9. A compound according to claim 1, wherein
Ar$^1$ is an aryl or heteroaryl group;
R$^1$ and R$^2$ are the same or different, selected from the group consisting of a halogen atom, a methyl group, a halomethyl group, a methoxy group, and a halomethoxy group;
R$^3$ is a hydrogen atom;
(Alk$^1$)$_r$L$^1$ is —CONH—;
Alk$^2$ is absent or —CH$_2$—;

m is zero or 1;
R is a carboxylic acid group;
$R^6$ and $R^a$ are each a hydrogen atom; and
$Ar^2$ is an optionally substituted monocyclic nitrogen-containing heteroaromatic group selected from the group consisting of pyridyl, pyrimidinyl, pyridazinyl and triazinyl groups.

10. The compound of claim 9, wherein
$Ar^1$ is a pyridyl group; and
$R^1$ and $R^2$ are independently selected from the group consisting of fluorine, chlorine, —$CF_3$, —$CHF_2$, —$CH_2F$, —$OCF_3$, —$OCHF_2$, and —$OCH_2F$.

* * * * *